(12) United States Patent
Kesteleyn et al.

(10) Patent No.: US 7,615,639 B2
(45) Date of Patent: Nov. 10, 2009

(54) 1-PYRIDYL-BENZOFURO[3,2-B]PYRIDIN-2(1H)-ONES

(75) Inventors: Bart Rudolf Romanie Kesteleyn, Berlare (BE); Pierre Jean-Marie Bernard Raboisson, Sterrebeek (BE); Dominique Louis Nestor Surleraux, Braine-le-château (BE); Geerwin Yvonne Paul Haché, Brasschaat (BE); Sandrine Marie Helene Vendeville, Etterbeek (BE); Piet Tom Bert Paul Wigerinck, Terhagen (BE); Annick Ann Peeters, Wilrijk (BE)

(73) Assignee: Tibotec Pharmaceuticals, Ltd. (IE)

( * ) Notice: Subject to any disclaimer, the term of this patent is extended or adjusted under 35 U.S.C. 154(b) by 12 days.

(21) Appl. No.: 11/568,845
(22) PCT Filed: May 17, 2005
(86) PCT No.: PCT/EP2005/052264
§ 371 (c)(1),
(2), (4) Date: Nov. 8, 2006
(87) PCT Pub. No.: WO2005/011647
PCT Pub. Date: Nov. 24, 2005

(65) Prior Publication Data
US 2007/0265295 A1    Nov. 15, 2007

(30) Foreign Application Priority Data
May 17, 2004   (EP) .................. 04102171

(51) Int. Cl.
*C07D 471/00* (2006.01)
(52) U.S. Cl. ........................................ 546/81
(58) Field of Classification Search ............ 546/81
See application file for complete search history.

(56) References Cited
FOREIGN PATENT DOCUMENTS

| EP | 0499299 B1 | 8/1992 |
|---|---|---|
| EP | 0721331 B1 | 7/1996 |
| WO | WO 9405263 A1 | 3/1994 |
| WO | WO 9744014 A1 | 11/1997 |
| WO | WO 9842318 A1 | 10/1998 |
| WO | WO 0208226 A | 1/2002 |
| WO | WO 0255520 A2 | 7/2002 |
| WO | WO 02059123 A2 | 8/2002 |
| WO | WO 03020700 A | 3/2003 |
| WO | WO 2004046143 A1 | 6/2004 |

OTHER PUBLICATIONS

Ryabova, S., et al., Russian Chem. Bull. 2001, 50(8), pp. 1449-1456.
Ryabova, S.Y. et al '1H-Pyrido3, 2-Bindoles. Synthesis and Investigation of Some Their Spectroscopic and Chemical Properties' Chem. of Hetero. Comp. vol. 36 No. 3 2000, pp. 301-306, XP001079898.
Benet, L. at al., "Pharmacokinetics: The Dynamics of Drug Absorption, Distribution, and Elimination.", *Goodman and Gilman's The Pharmacological Basis of Therapeutics*, Eighth Edition, 1992, pp. 13-18, McGraw-Hill Inc.
D'Aquila, et al., Topics in HIV Medicine 2002, 10, pp. 11-15.
Azimov, V.A., et al., Chemistry of Heterocyclic Compounds, 2000, 36, pp. 1272-1275.
Benoit, R. et al., "Facile Synthesis of Annelated NADH Model Precursors", Synthesis 1987, pp. 1124-1126.
Hertogs, K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs.", *Antimicrobial Agents and Chemotherapy*, Feb. 1998, vol. 42, No. 2, pp. 269-276.
Papamicael, C. et al., "A convenient systhesis of 3,4-difunctionalized δ-carbolines", Tetrahedron 2001, 57, pp. 5385-5391.
International Search Report re: PCT/EP2005/052264 dated Oct. 4, 2005.

*Primary Examiner*—D. Margaret Seaman
*Assistant Examiner*—Nizal S Chandrakumar

(57) ABSTRACT

1-heterocyclyl-1,5-dihydro-pyrido[3,2-b]indol-2-ones of formula (I):

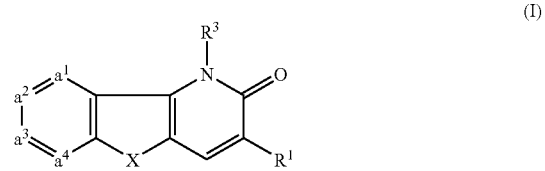

the N-oxides, salts, stereoisomeric forms, racemic mixtures, prodrugs, esters and metabolites thereof, wherein n is 1, 2 or 3;

$R^1$ is hydrogen, cyano, halo, substituted carbonyl, methanimidamidyl, N-hydroxy-methanimidamidyl, mono- or di($C_{1-4}$alkyl)methanimidamidyl, $Het_1$ or $Het_2$;

X is $NR_2$, O, S, SO, $SO_2$;

$R^2$ is hydrogen, $C_{1-10}$alkyl, $C_{2-10}$alkenyl, $C_{3-7}$cycloalkyl, which are optionally substituted; $R^2$ is aryl substituted with —$COOR^4$; or $R^2$ is:

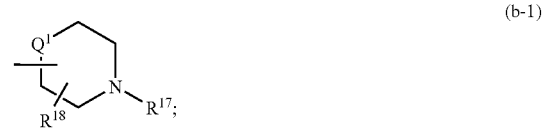

(b-1)

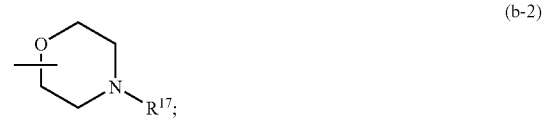

(b-2)

—$C_pH_{2p}$—$CH(OR^{14})$—$C_qH_{2q}$—$R^{15}$ (b-3);

—$CH_2$—$CH_2$—(O—$CH_2$—$CH_2$)$_m$—$OR^{14}$ (b-4);

—$CH_2$—$CH_2$—(O—$CH_2$—$CH_2$)$_m$—$NR^{5a}R^{5b}$ (b-5);

-$a^1$=$a^2$-$a^3$=$a^4$- is —CH=CH—CH=CH—; —N=CH—CH=CH—; —CH=N—CH=CH—; —CH=CH—N=CH—; —CH=CH—CH=N—; wherein hydrogen atoms in (c-1)-(c-5) may be replaced by certain radicals;

$R^3$ is a monocyclic or bicyclic aromatic heterocyclic ring system that can be substituted.

18 Claims, No Drawings

1-PYRIDYL-BENZOFURO[3,2-B]PYRIDIN-2(1H)-ONES

CROSS REFERENCE TO RELATED APPLICATIONS

This application is the national stage of PCT Application No. PCT/EP2005/052264, filed 17 May 2005, which claims priority from European Patent Application No. 04102171.8, filed 17 May 2004, The entire disclosures of which are hereby incorporated in their entirety.

This invention relates to 1-heterocyclyl-1,5-dihydro-pyrido[3,2-b]indol-2-ones, their use as anti-infective agents, , the use of these compounds as HIV inhibitors, to pharmaceutical compositions containing these compounds and to processes for preparing these compounds and compositions.

The virus causing the acquired immunodeficiency syndrome (AIDS) is known by different names, including T-lymphocyte virus III (RTLV-III), lymphadenopathy-associated virus (LAV), AIDS-related virus (ARV) or human immunodeficiency virus (HIV). Up until now, two distinct classes have been identified, i.e. HIV-1 and HIV-2. Hereinafter, the term HIV will be used to generically denote both these classes.

HIV infected patients are currently treated with HIV protease inhibitors (PIs), nucleoside reverse transcriptase inhibitors (NRTIs), non-nucleoside reverse transcriptase inhibitors (NNRTIs) and nucleotide reverse transcriptase inhibitors (NtRTIs). Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever-increasing resistance against any available drugs, which is a major cause of therapy failure. Moreover, it has been shown that resistant virus is carried over to newly infected individuals, resulting in severely limited therapy options for these drug-naive patients.

Current HIV therapy comprises in most cases the administration of drug cocktails comprising two or more active ingredients selected from the above classes of HIV inhibitors. But even when using combination therapy, drug resistance arises resulting in the combination becoming less effective. This often may force the treating physician to boost the plasma levels of the active drugs in order for said antiretrovirals to regain effectivity against the mutated HIV viruses, the consequence of which is an undesirable increase in pill burden. The latter in turn may also lead to an increased risk of non-compliance with the prescribed therapy.

Therefore, there is a continuous general need for new combinations of HIV inhibitors that comprise new types of HIV inhibitory agents. Hence there is a need for new HIV inhibitors that differ from existing inhibitors in terms of chemical structure as well as mode of action or both. There is a particular need for compounds that are active not only against wild type HIV virus, but also against the increasingly more common resistant HIV viruses.

Currently used HIV reverse transcriptase inhibitors belong to three different classes. These include the NRTIs, which are intracellularly converted to nucleoside triphosphates that compete with the natural nucleoside triphosphates for incorporation into elongating viral DNA by reverse transcriptase. Chemical modifications that distinguish these compounds from natural nucleosides result in DNA chain termination events. NRTIs that are currently available include zidovudine (AZT), didanosine (ddI), zalcitabine (ddC), stavudine (d4T), lamivudine (3TC) and abacavir (ABC). A second class comprises the NtRTIs such as tenofovir, which have a similar mode of action as the NRTIs. Emergence of mutations causes the NRTIs and NtRTIs to become ineffective. A third class comprises the NNRTIs, which interact with the NNRTI binding site and thereby block the RT mechanism. Currently available NNRTIs include nevirapine, delavirdine and efavirenz, known to be susceptible to relative rapid emergence of resistance due to mutations at amino acids that surround the NNRTI-binding site.

Thus, there is a medical need for further anti-infective compounds that target HIV reverse transcriptase, in particular anti-retroviral compounds that are able to delay the occurrence of resistance and that combat a broad spectrum of mutants of the HIV virus.

WO02/055520 and WO02/059123 disclose benzoylalkylindolepyridinium compounds as antiviral compounds. Ryabova et al. disclose the synthesis of certain benzoylalkylindolepyridinium compounds (Russian Chem. Bull. 2001, 50(8), 1449-1456; and Chem. Heterocycl. Compd. (Engl. Translat.) 36; 3; 2000; 301-306; Khim. Geterotsikl. Soedin.; RU; 3; 2000; 362-367).

The compounds of this invention differ from these prior art compounds in terms of chemical structure as well as by the fact that they interact via a mechanism that differs from known RT inhibitors. They not only are active against wild type HIV virus but also against mutant HIV viruses, in particular mutant HIV viruses exhibiting resistance against currently available reverse transcriptase (RT) inhibitors.

Thus in one aspect the present invention concerns substituted 1-heterocyclyl-1,5-dihydro-pyrido[3,2-b]indol-2-ones of formula (I):

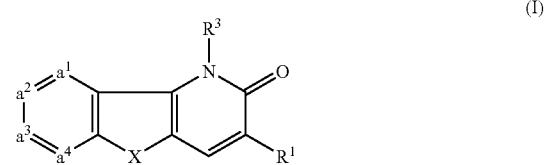

(I)

the N-oxides, salts, quaternary ammonium salts, stereoisomeric forms, prodrugs, esters and metabolites thereof, wherein $R^1$ is hydrogen, cyano, halo, aminocarbonyl, hydroxycarbonyl, $C_{1-4}$alkyloxycarbonyl, $C_{1-4}$alkylcarbonyl, mono- or di($C_{1-4}$alkyl)aminocarbonyl, arylaminocarbonyl, N-(aryl)-N-($C_{1-4}$alkyl)aminocarbonyl, methanimidnnidyl, N-hydroxy-methanimidamidyl, mono- or di($C_{1-4}$alkyl) methanimidamidyl, $Het_1$ or $Het_2$;

X is a bivalent radical $NR_2$, O, S, SO, $SO_2$;

$R^2$ is:

i) hydrogen, $C_{1-10}$alkyl, $C_{2-10}$alkenyl, $C_{3-7}$cycloalkyl, wherein said $C_{1-10}$alkyl, $C_{2-10}$alkenyl and $C_{3-7}$cycloalkyl, each individually and independently, may be optionally substituted with a substituent selected from the group consisting of cyano, $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $N(R^{16a}R^{16b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-yl-carbonyl, thiomorpholin-1-ylcarbonyl, 1-oxothiomorpholin-1-ylcarbonyl and 1,1-dioxo-thiomorpholin-1-ylcarbonyl; or $R^2$ is ii) aryl substituted with a radical —$COOR_4$; or $R^2$ is iii) $C_{1-10}$alkyl, $C_{2-10}$alkenyl $C_{3-7}$cycloalkyl, each of said $C_{1-10}$alkyl, $C_{2-10}$alkenyl, $C_{3-7}$cycloalkyl, each individually and independently, being substituted with aryl wherein said aryl is substituted with a radical —$COOR^4$; or $R^2$ is iv) $C_{1-10}$alkyl, $C_{2-10}$alkenyl, $C_{3-7}$cycloalkyl, each individually and independently, substituted with a radical selected from —$NR^{5a}$—C(=$NR^{5b}$)—$NR^{5c}R^{5d}$, —$NR^{5a}$—C(=$NR^{5e}$)—$R^{5f}$, —O—$NR^{5a}$—C(=$NR^{5b}$)—$NR^{5c}R^{5d}$, —O—$NR^{5a}$—C(=$NR^{5e}$)—$R^{5f}$, -sulfonyl-$R^6$, —$NR^7R^8$, —$NR^9R^{10}$, a radical

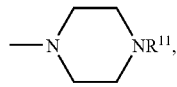  (a-1)

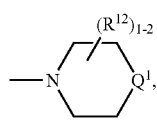  (a-2)

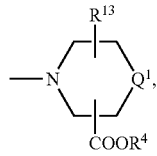  (a-3)

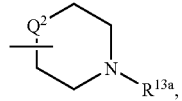  (a-4)

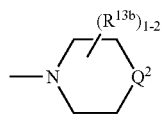  (a-5)

wherein each $Q^1$ independently is a direct bond, —$CH_2$—, or —$CH_2$—$CH_2$—;

each $Q^2$ independently is O, S, SO or $SO_2$;

each $R^4$ independently is hydrogen, $C_{1-4}$alkyl, aryl$C_{1-4}$alkyl;

each $R^{5a}$, $R^{5b}$, $R^{5c}$, $R^{5d}$ independently is hydrogen, $C_{1-4}$alkyl or aryl$C_{1-4}$alkyl;

each $R^{5e}$, $R^{5f}$ independently is hydrogen, $C_{1-4}$alkyl or aryl$C_{1-4}$alkyl, or $R^{5e}$ and $R^{5f}$, taken together may form a bivalent alkanediyl radical of formula —$CH_2$—$CH_2$— or —$CH_2$—$CH_2$—$CH_2$—;

$R^6$ is $C_{1-4}$alkyl, —N($R^{5a}R^{5b}$), $C_{1-4}$alkyloxy, pyrrolidin-1-yl, piperidin-1-yl, homopiperidin-1-yl, piperazin-1-yl, 4-($C_{1-4}$ alkyl)-piperazin-1-yl, morpholin-4-yl-, thiomorpholinyl-4-yl-, 1-oxothiomorpholin-4-yl and 1,1-dioxothiomorpholinyl;

$R^7$ is hydrogen, $C_{1-4}$alkyl, hydroxy$C_{1-4}$alkyl, $C_{1-4}$alkoxy$C_{1-4}$alkyl or $C_{1-4}$alkyl-carbonyloxy$C_{1-4}$alkyl;

$R^8$ is hydroxy$C_{1-4}$alkyl, $C_{1-4}$alkoxy$C_{1-4}$alkyl, $C_{1-4}$alkylcarbonyloxy$C_{1-4}$alkyl, aryl or aryl$C_{1-4}$alkyl;

$R^9$ is hydrogen or $C_{1-4}$alkyl;

$R^{10}$ is $Het_1$, $Het_2$ or a radical

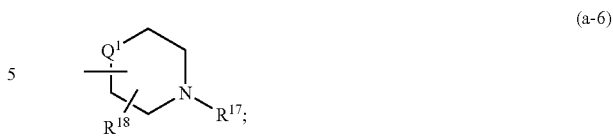  (a-6)

$R^{11}$ is aryl, aryl$C_{1-4}$alkyl, formyl, $C_{1-4}$alkylcarbonyl, arylcarbonyl, aryl$C_{1-4}$alkyl-carbonyl, $C_{1-4}$alkyloxycarbonyl, aryl$C_{1-4}$alkyloxycarbonyl, $R^{5a}R^{5b}$N-carbonyl, hydroxy$C_{1-4}$alkyl, $C_{1-4}$alkyloxy$C_{1-4}$alkyl, aryl$C_{1-4}$alkyloxy$C_{1-4}$alkyl, aryloxy$C_{1-4}$alkyl, $Het_2$;

each $R^{12}$ independently is hydroxy, $C_{1-4}$alkyl, aryl$C_{1-4}$alkyl, $C_{1-4}$alkyloxy, aryl$C_{1-4}$alkyloxy, oxo, spiro($C_{2-4}$alkanedioxy), spiro(di$C_{1-4}$alkyloxy), —$NR^{5a}R^{5b}$;

$R^{13}$ is hydrogen, hydroxy, $C_{1-4}$alkyl, $C_{1-4}$alkyloxy, or aryl$C_{1-4}$ alkyloxy; or $R^{13a}$ is $C_{1-4}$alkyl, aryl$C_{1-4}$alkyl, $C_{1-4}$alkyloxycarbonyl or aryl$C_{1-4}$alkyloxycarbonyl;

each $R^{13b}$ is hydrogen or $C_{1-4}$alkyl; or $R^2$ is v) a radical of formula:

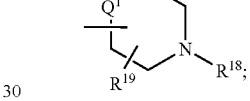  (b-1)

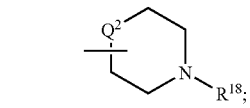  (b-2)

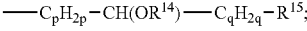  (b-3)

  (b-4)

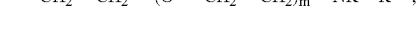  (b-5)

wherein in radical (b-3) one of the hydrogen atoms in —$C_pH_{2p}$— and one of the hydrogen atoms in —CH($OR^{14}$)—$C_qH_{2q}$—, that is not part of $R^{14}$, may be replaced by a direct bond or a $C_{1-4}$alkanediyl group;

p is 1, 2 or 3;

q is 0, 1, 2 or 3;

m is 1 to 10;

each $R^{14}$ independently is hydrogen, $C_{1-4}$alkyl, aryl $C_{1-4}$alkyl, aryl, $C_{1-4}$alkylcarbonyl, —$SO_3H$, —$PO_3H_2$;

$R^{15}$ is a substituent selected from the group consisting of cyano, $NR^{16a}R^{16b}$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxothiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkyl-carbonyl, N($R^{16a}R^{16b}$)carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-yl-carbonyl, thiomorpholin-1-ylcarbonyl, 1-oxothiomorpholin-1-ylcarbonyl and 1,1-dioxo-thiomorpholin-1-ylcarbonyl; and wherein $R^{15}$ may additionally be aryl substituted with a radical —$COOR^4$; or a radical selected from —NR$^{5a}$—C(=NR$^{5b}$)NR$^{5c}$R$^{5d}$, —NR$^{5a}$—C(=NR$^{5e}$)—R$^{5f}$, —O—NR$^{5a}$—C(=NR$^{5b}$)—NR$^{5c}$R$^{5d}$, —O—NR$^{5a}$—C(=NR$^{5e}$)—R$^{5f}$, -sulfonyl-R$^6$, —NR$^7$R$^8$, —NR$^9$R$^{10}$, a radical (a-1), (a-2), (a-3); wherein R$^4$, R$^{5a}$, R$^{5b}$, R$^{5c}$, R$^{5d}$, R$^6$, R$^7$, R$^8$, R$^9$, R$^{10}$, and the radicals (a-1), (a-2), (a-3) independently are as defined above;

R$^{16a}$ is hydrogen, C$_{1-4}$alkyl or C$_{1-4}$alkyl substituted with a substituent selected from the group consisting of amino, mono- or di(C$_{1-4}$alkyl)amino, pyrrolidinyl, piperidinyl, homopiperidinyl, piperazinyl, 4-(C$_{1-4}$alkyl)-piperazinyl, morpholinyl, thiomorpholinyl, 1-oxothiomorpholinyl and 1,1-dioxo-thiomorpholinyl; $^{R16b}$ is hydrogen, C$_{1-4}$alkyl or C$_{1-4}$alkyl substituted with a substituent selected from the group consisting of amino, mono- or di(C$_{1-4}$alkyl)amino, pyrrolidinyl, piperidinyl, homopiperidinyl, piperazinyl, 4-(C$_{1-4}$alkyl)-piperazinyl, morpholinyl, thiomorpholinyl, 1-oxothiomorpholinyl and 1,1-dioxo-thiomorpholinyl;

each R$^{17}$ independently is hydrogen, C$_{1-4}$alkyl or arylC$_{1-4}$alkyl;

R$^{18}$ is hydrogen, hydroxy, C$_{1-4}$alkyl or a radical —COOR$^4$;

-a$^1$=a$^2$-a$^3$=a$^4$- represents a bivalent radical of formula

—CH=CH—CH=CH— (c-1);

—N=CH—CH=CH— (c-2);

—CH=N—CH=CH— (c-3);

—CH=CH—N=CH— (c-4);

—CH=CH—CH=N— (c-5);

wherein one, two, three or four of the hydrogen atoms in (c-1) may be replaced by a radical C$_{1-6}$alkyl, C$_{1-4}$alkoxy, halo, hydroxy, (R$^{5g}$)(R$^{5h}$)N—(C$_{1-4}$alkanediyl)-O—, (R$^7$)(R$^8$)N—(C$_{1-4}$alkanediyl)-O—, (R$^8$)(R$^9$)N—(C$_{1-4}$alkanediyl)-O—, trifluoromethyl, cyano, a radical —COOR$^4$, (R$^{5a}$)(R$^{5b}$)N-carbonyl, (R$^{5a}$)(R$^{5b}$)N-sulfonyl, pyrrolidinylsulfonyl, piperidinylsulfonyl, homopiperidinylsulfonyl, formyl, C$_{1-6}$alkylcarbonyl, nitro, hydroxyC$_{1-6}$alkyl, C$_{1-4}$alkoxyC$_{1-6}$alkyl, (R$^4$OOC)—C$_{1-6}$alkyl, a radical —N(R$^{5a}$)(R$^{5e}$), —N(R$^7$)(R$^8$), —N(R$^9$)(R$^{10}$), a radical

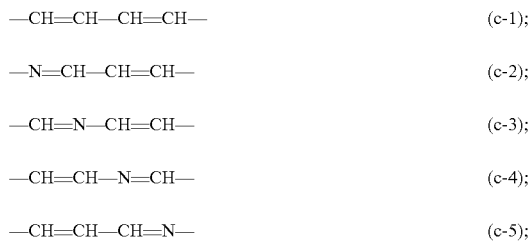

(a-1)

(a-7)

morpholinyl, thiomorpholinyl, 1-oxothiomorpholinyl, 1,1-dioxo-thiomorpholinyl, (R$^{5g}$)(R$^{5h}$)N—(C$_{1-4}$alkanediyl)-N(R$^{5c}$)—, (R$^7$)(R$^8$)N—(C$_{1-4}$alkanediyl)-N(R$^{5c}$)—, (R$^9$)(R$^{10}$)N—(C$_{1-4}$alkanediyl)-N(R$^{5c}$)—, C$_{1-6}$alkylcarbonylamino, C$_{1-6}$alkyloxycarbonylamino, trifluoroacetylamino, C$_{1-6}$alkylsulfonylamino, (R$^{5a}$)(R$^{5b}$)N—C$_{1-4}$alkyl; aryl; Het$_1$ or Het$_2$;

R$^{20}$ is hydrogen, hydroxy, C$_{1-4}$alkyl, arylC$_{1-4}$alkyl, C$_{1-4}$alkyloxy, arylC$_{1-4}$alkyloxy, oxo, spiro(C$_{2-4}$alkylenedioxy), spiro(diC$_{1-4}$alkyloxy), —R$^{5g}$R$^{5h}$;

each R$^{5g}$ or R$^{5h}$ independently is hydrogen, C$_{1-4}$alkyl or arylC$_{1-4}$alkyl, or R$^{5g}$ and R$^{5h}$ together with the nitrogen to which they attached form a pyrrolidinyl, piperidinyl, homopiperidinyl, morpholinyl, piperazinyl or 4-C$_{1-4}$alkylpiperazinyl radical;

wherein each of said pyrrolidinyl, piperidinyl, homopiperidinyl, morpholinyl, piperazinyl or 4-C$_{1-4}$alkylpiperazinyl radical may optionally be substituted with hydroxy or oxo; or wherein one or more of the hydrogen atoms in (c-2), (c-3), (c-4) or (c-5) may be replaced with a radical selected from halo and C$_{1-6}$alkyl;

R$^3$ is a monocyclic or bicyclic aromatic heterocyclic ring system, wherein one, two, three or four ring members are heteroatoms each independently selected from the group consisting of nitrogen, oxygen and sulfur, and wherein the remaining ring members are carbon atoms; and wherein each of said heterocyclic ring systems may optionally be substituted with one, two, three, four or five substituents each independently selected from halo, cyano, nitro, C$_{1-6}$alkyl, hydroxyC$_{1-6}$alkyl, C$_{1-4}$alkoxyC$_{1-6}$alkyl, (R$^{5a}$)(R$^{5b}$)N—C$_{1-6}$alkyl, polyhaloC$_{1-6}$alkyl, C$_{3-7}$cycloalkyl, arylC$_{1-6}$alkyl, formyl, C$_{1-6}$alkylcarbonyl, a radical —COOR$^4$, (R$^{5a}$)(R$^{5b}$)N-carbonyl, (R$^{5a}$)(R$^{5b}$)N-sulfonyl, hydroxy, C$_{1-6}$alkyloxy, arylC$_{1-6}$alkyloxy, polyhaloC$_{1-6}$alkyloxy, formyloxy, C$_{1-6}$alkylcarbonyloxy, aryloxy, (R$^{5a}$)(R$^{5b}$)N—, formylamino, C$_{1-6}$alkylcarbonylamino, C$_{1-6}$alkyloxycarbonylamino C$_{1-6}$alkylsulfonylamino, mercapto, C$_{1-6}$alkylthio, arylthio, arylC$_{1-6}$alkylthio, C$_{1-6}$alkylsulfinyl, C$_{1-6}$alkylsulfonyl, aryl, —CH(=N—O—R$^{5a}$), —C(=NH)—N—R$^{5a}$;

aryl is phenyl optionally substituted with one or more substituents each individually selected from the group consisting of C$_{1-6}$alkyl C$_{1-4}$alkoxy, halo, hydroxy, amino, trifluoromethyl, cyano, nitro, hydroxyC$_{1-6}$alkyl, cyanoC$_{1-6}$alkyl, mono- or di(C$_{1-4}$alkyl)amino, aminoC$_{1-4}$alkyl, mono- or di(C$_{1-4}$alkyl)aminoC$_{1-4}$alkyl;

Het$_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with C$_{1-4}$alkyl; any ring carbon atom may, each individually and independently, optionally be substituted with a substituent selected from the group consisting of C$_{1-4}$alkyl, C$_{2-6}$alkenyl, C$_{3-7}$cycloalkyl, hydroxy, C$_{1-4}$alkoxy, halo, amino, cyano, trifluoromethyl, hydroxyC$_{1-4}$alkyl, cyanoC$_{1-4}$alkyl, mono- or di(C$_{1-4}$alkyl)amino, aminoC$_{1-4}$alkyl, mono- or di(C$_{1-4}$alkyl)aminoC$_{1-4}$alkyl, arylC$_{1-4}$alkyl, aminoC$_{2-6}$alkenyl, mono- or di(C$_{1-4}$alkyl)aminoC$_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, C$_{1-4}$alkyloxycarbonyl, mono- or di(C$_{1-4}$alkyl)aminocarbonyl, C$_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with C$_{1-4}$alkyl;

Het$_2$ is pyridyl, pyrimidinyl, pyrazinyl, pyridazinyl or triazinyl, wherein any ring carbon atom of each of said 6-membered nitrogen containing aromatic rings may optionally be substituted with a substituent selected from the group consisting of C$_{1-4}$alkyl.

As used herein "C$_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "C$_{1-6}$alkyl" encompasses C$_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. The term "$C_{1-10}$alkyl" as a group or part of a group encompasses $C_{1-6}$alkyl radicals and the higher homologues thereof having from 7 to 10 carbon atoms such as, for example, 1-heptyl, 2-heptyl, 2-methyl-1-hexyl, 2-ethyl-1-hexyl, 1-octyl, 2,octyl, 2-methyl-1-heptyl, 2-methyl-2-heptyl, 1-nonyl, 2-nonyl, 2-methyl-1-octyl, 2-methyl-2-octyl, 1-decyl, 2-decyl, 3-decyl, 2-methyl-1-decyl and the like.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, propenyl, buten-1-yl, buten-2-yl, 2-buten-1-yl, 3-buten-1-yl, penten-1-yl, penten-2-yl, 2-penten-2-yl, hexen-1-yl, hexen-2-yl, hexen-3-yl, 2-methylbuten-1-yl, 1-methyl-2-penten-1-yl and the like. The term "$C_{2-10}$alkenyl" as a group or part of a group defines comprises $C_{2-6}$alkenyl groups and the higher homologues thereof having from 7 to 10 carbon atoms and at least one double bond such as, for example, hepten-1-yl, 2-hepten-1-yl, 3-hepten-1-yl, octen-1-yl, 2-octen-1-yl, 3-octen-1-yl, nonen-1-yl, 2-nonen-1-yl, 3-nonen-1-yl, 4-nonen-1-yl, decen-1-yl, 2-decen-1-yl, 3-decen-1-yl, 4-decen-1-yl, 1-methyl-2-hexen-1-yl and the like. Preferred are $C_{2-6}$alkenyl or $C_{2-10}$alkenyl groups having one double bond. Whenever linked to a heteroatom, the $C_{2-6}$alkenyl or $C_{2-10}$alkenyl groups by preference are linked to the hetero atom by a saturated carbon atom. Preferred subgroups amongst $C_{2-6}$alkenyl or $C_{2-10}$alkenyl are $C_{3-6}$alkenyl or $C_{3-10}$alkenyl which are alkenyl groups as specified herein having from 3 to 6 or from 3 to 10 carbon atoms.

The term "$C_{3-7}$cycloalkyl" is generic to cyclopropyl, cyclobutyl, cyclopentyl, cyclohexyl and cycloheptyl.

The term "$C_{1-4}$alkanediyl" defines bivalent straight and branched chain saturated hydrocarbon radicals having from 1 to 4 carbon atoms such as, for example, methylene, 1,2-ethanediyl, 1,3-propanediyl, 1,4-butanediyl, 1,2-propanediyl, 2,3-butanediyl, and the like, refers to bivalent $C_{1-4}$alkyl radicals having from one to four carbon atoms, in particular methylene, 1,2-ethanediyl, 1,1-ethanediyl, 1,2-propanediyl, 1,3-propanediyl, 1,2-butanediyl, 1,3-butanediyl, 1,4-butanediyl. "$C_{2-4}$alkanediyl" similarly refers to bivalent hydrocarbon atoms having 2 to 4 carbon atoms. Of particular interest are the $C_{1-4}$alkanediyl groups in which the carbon atoms bearing the connecting bond are next to one another (in vicinal position), these groups sometimes being referred to as ethylene, propylene and butylene.

"$C_{2-4}$alkanedioxy" refers to straight and branched chain saturated hydrocarbon radicals having 2-4 carbon atoms and two oxy (—O—) groups, e.g. 1,2-ethanedioxy (—O—$CH_2$—$CH_2$—O—), 1,3-propanedioxy (—O—$CH_2CH_2CH_2$—O—), 1,2-propanedioxy (—O—$CH_2$—$CH(CH_3)$—O—), 1,4-butanedioxy (—O—$CH_2CH_2CH_2CH_2$—O—), and the like.

The terms "spiro($C_{2-4}$alkanedioxy)" and "spiro(di$C_{1-4}$alkyloxy)" refer to a linkage of the $C_{2-4}$alkanedioxy and di$C_{1-4}$alkyloxy groups to the same carbon atom, whereby in the former instance a ring is formed.

The term "halo" is generic to fluoro, chloro, bromo or iodo.

A hydroxy$C_{1-6}$alkyl group when substituted on an oxygen atom or a nitrogen atom preferably is a hydroxy$C_{2-6}$alkyl group wherein the hydroxy group and the oxygen or nitrogen are separated by at least two carbon atoms.

As used in the foregoing and hereinafter polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, the groups defined in halomethyl, 1,1-difluoroethyl and the like. A preferred subgroup of polyhalo$C_{1-6}$alkyl is polyhalo$C_{1-4}$alkyl, a particularly preferred subgroup of polyhalo$C_{1-6}$-alkyl or of polyhalo$C_{1-4}$alkyl is polyhalomethyl, wherein the latter as a group or part of a group is defined as mono- or polyhalosubstituted methyl, in particular methyl with one or more fluoro atoms, for example, difluoromethyl or trifluoromethyl. In case more than one halogen atoms are attached to an alkyl group within the definition of polyhalomethyl, polyhalo$C_{1-4}$alkyl or polyhalo$C_{1-6}$alkyl, they may be the same or different.

The term "methanimidamidyl" is used in accordance with the Chemical Abstracts Nomenclature (CAS) and refers to the radical of formula $H_2N$—C(=NH)—, which radical can also be referred to as "amidine". Likewise N-hydroxy-methanimidamidyl is used in accordance with the CAS nomenclature and refers to the radical of formula $H_2N$—C(=N—OH)— or its tautomer HN=C(—NH—OH)—, which radical can also be referred to as "hydroxyamidine".

The term "hydroxycarbonyl" refers to a carboxyl group (—COOH).

The aryl group is phenyl optionally substituted with one or more substituents and in particular is phenyl optionally substituted with one, two, three, four or five substituents, preferably phenyl substituted with one, two or three substituents.

$Het_1$ in particular is a 5-membered ring system as specified above wherein the ring system is aromatic. More particularly, $Het_1$ is a 5-membered ring system as specified above wherein the ring system contains one oxygen, sulfur or nitrogen, and optionally one, two or three further nitrogen atoms and wherein the remaining ring members are carbon atoms. Further in particular, $Het_1$ is an aromatic 5-membered ring system as specified above wherein the ring system contains one oxygen, sulfur or nitrogen atom, and optionally one, two or three further nitrogen atoms and wherein the remaining ring members are carbon atoms. In each of the instances mentioned in this paragraph, $Het_1$ may be optionally substituted with any of substituents specified herein in the definitions of the compounds of formula (I) as well as any of the subgroups of compounds of formula (I).

Examples of $Het_1$ rings are furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, each of which individually and independently may be optionally substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano-$C_{1-4}$alkyl, mono- or di($C_{1-4}$alkyl) amino, amino$C_{1-4}$alkyl, mono- or di($C_{1-4}$alkyl)-amino$C_{1-4}$alkyl, aryl$C_{1-4}$alkyl, amino$C_{2-6}$alkenyl, mono- or di($C_{1-4}$alkyl)amino-$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxylcarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl.

The substituents $R^{12}$, $R^{13}$, $R^{13a}$, —$COOR^4$, $R^{18}$, $R^{19}$, $R^{20}$ on radicals (a-2), (a-3), (a-5), (a-6), (a-7) and (b-1) may be positioned at any ring carbon atom, including the atoms of radicals $Q^1$. Preferably, the substituents $R^{12}$, $R^{13}$, $R^{13a}$, $R^{19}$ or $R^{20}$ are not in α-position from the ring nitrogen atom, in particular where any of said substituents is oxo, spiro($C_{2-4}$alkanediyldioxy), spiroC(di$C_{1-4}$alkyloxy), —$NR^{5a}R^{5b}$, hydroxy or $C_{1-4}$alkyloxy. Of particular interest are radicals (a-2), (a-3), (a-5), (a-6), (a-7) or (b-1) wherein substituents $R^{12}$, $R^{13}$, $R^{13a}$, $R^{18}$ or $R^{19}$ are positioned on a carbon atom of $Q^1$ or where $Q^1$ is a direct bond, on the ring carbon atom to which $Q^1$ is linked.

The connecting bond in radicals (a-4), (a-6) or (b-1) may be positioned at any ring carbon atom, including the atoms of radicals $Q^1$.

$R^3$ is a monocyclic or bicyclic aromatic heterocyclic ring system as specified above. In particular, $R^3$ is a monocyclic or bicyclic aromatic heterocyclic ring system as specified above wherein the ring system contains one oxygen, sulfur or nitrogen, and optionally one, two or three further nitrogen atoms and wherein the remaining ring members are carbon atoms; optionally substituted with the substituents as specified above.

Examples of $R^3$ rings are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl; optionally substituted with the substituents as specified above.

Particular examples of $R^3$ rings are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, carbazolyl, acridinyl, phenothiazinyl, phenoxazinyl; optionally substituted with the substituents as specified above.

Particularly interesting $R^3$ rings are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, imidazopyrimidinyl, purinyl, quinolinyl, isoquinolinyl, phthalazinyl, quinoxalinyl, quinazolinyl; optionally substituted with the substituents as specified above.

It should be noted that different isomers of the various heterocycles may exist within the definitions as used throughout the specification. For example, oxadiazolyl may be 1,2,4-oxadiazolyl or 1,3,4-oxadiazolyl or 1,2,3-oxadiazolyl; likewise for thiadiazolyl which may be 1,2,4-thiadiazolyl or 1,3,4-thiadiazolyl or 1,2,3-thiadiazolyl; pyrrolyl may be 1H-pyrrolyl or 2H-pyrrolyl.

One embodiment concerns those compounds or subgroups of compounds wherein $R^3$ is imidazopyridyl which includes all isomers, in particular imidazo[1,2-a]pyridinyl and 3H-imidazo[4,5-b]pyridinyl. Of interest are those compounds or subgroups of compounds wherein $R^3$ is imidazo[1,2-a]pyridine-6-yl or 3H-imidazo[4,5-b]pyridine-6-yl. Of further interest are those compounds or subgroups of compounds wherein $R^3$ is imidazo[1,2-a]pyridine-6-yl.

In radicals (c-1) to (c-5) a number of the hydrogen atoms in said radicals (c-1)-(c-5) may be replaced by certain radicals, this meaning that none or one or several of the hydrogen atoms may be replaced by certain radicals.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl, morpholinyl includes 4-morpholinyl, 3-morpholinyl and 2-morpholinyl.

When any variable (e.g. halogen or $C_{1-4}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, $8^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl groups. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The compounds of formula (I) containing an acidic proton may also be converted into their non-toxic metal or amine addition base salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

The term "quaternary ammonium salt" as used herein defines the quaternary ammonium salts which the compounds of formula (I) are able to form by reaction between a basic nitrogen of a compound of formula (I) and an appropriate quaternizing agent, such as, for example, an optionally substituted alkyl halide, aryl halide or arylalkyl halide, e.g. methyliodide or benzyliodide. Other reactants with good leaving groups may also be used, such as alkyl trifluoromethane sulfonates, alkyl methane sulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Particular quaternary ammonium salts are those derived from the groups —$NR^7R^8$, —$NR^9R^{10}$, —$N(R^{5a}R^{5b})$, pyrrolidin-1-yl, piperidin-1-yl, homopiperidin-1-yl, 4-($C_{1-4}$alkyl)piperazin-1-yl, morpholin-4-yl-, $NR^{16a}R^{16b}$; or $NR^{17a}R^{17b}$. These quaternized groups can be represented by the formulae

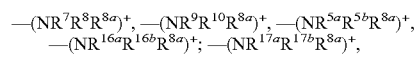

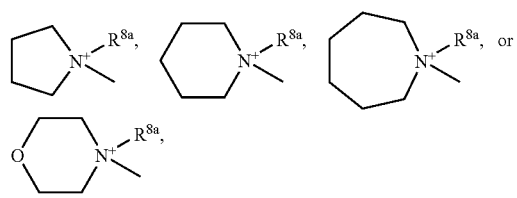

wherein each $R^{8a}$ independently is $C_{1-6}$alkyl, aryl$C_{1-6}$alkyl or hydroxy$C_{1-6}$alkyl, in particular each $R^{8a}$ independently is $C_{1-6}$alkyl or aryl$C_{1-6}$alkyl.

The N-oxide forms of the present compounds are meant to comprise the compounds of formula (I) wherein one or several nitrogen atoms are oxidized to the so-called N-oxide.

Some of the present compounds may also exist in tautomeric forms. Such forms, although not explicitly indicated in the above formula are intended to be included within the scope of the present invention. For example, within the definition of Het, a 5 membered aromatic heterocycle such as for example an 1,2,4-oxadiazole may be substituted with a hydroxy or a thio group in the 5-position, thus being in equilibrium with its respective tautomeric form as depicted below.

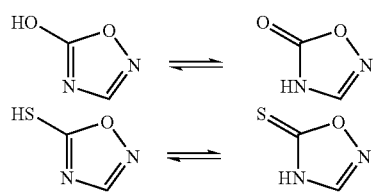

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound may be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues. One embodiment of the invention are the subgroups comprising the N-oxides of the compounds of formula (I) or of any subgroup of the compounds of formula (I) specified herein, including any salts or stereoisomeric forms thereof.

It is to be understood that any of the subgroups of compounds of formulae (I) is meant to also comprise any prodrugs, N-oxides, addition salts, quaternary amines and stereochemically isomeric forms of such compounds.

Embodiments of the present invention are those compounds of formula (I) or any of the subgroups of compounds of formula (I) specified herein, wherein:

(1) $R^1$ is hydrogen, cyano, halo, aminocarbonyl, $C_{1-4}$alkylaminocarbonyl, hydroxycarbonyl, $C_{1-4}$alkyloxycarbonyl, arylaminocarbonyl, N-hydroxy-methanimidamidyl, mono- or di($C_{1-4}$alkyl)methanimidamidyl, $Het_1$ or $Het_2$;

(1-a) $R^1$ is hydrogen, cyano, halo, aminocarbonyl, $C_{1-4}$alkylaminocarbonyl, arylaminocarbonyl, $C_{1-4}$alkyloxycarbonyl, N-hydroxy-methanimidamidyl, $Het_1$ or pyridinyl;

(1-b) $R^1$ is hydrogen, cyano, halo, aminocarbonyl, $C_{1-4}$alkylaminocarbonyl, arylaminocarbonyl, $C_{1-4}$alkyloxycarbonyl, N-hydroxy-methanimidamidyl, pyridinyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, each of which individually and independently may be optionally substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl;

(1-c) $R^1$ is hydrogen, cyano, halo, aminocarbonyl, $C_{1-4}$alkylaminocarbonyl, arylaminocarbonyl, $C_{1-4}$alkyloxycarbonyl, N-hydroxy-methanimidamidyl, pyridinyl, furanyl, thienyl, oxadiazolyl, tetrazolyl, wherein the latter four may be optionally substituted with $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio;

(1-d) $R^1$ is hydrogen, cyano, bromo, tetrazolyl or oxadiazolyl optionally substituted with a substituent selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxyl-$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio;

(1-e) $R^1$ is hydrogen, cyano, halo, aminocarbonyl, $C_{1-4}$alkylaminocarbonyl, arylaminocarbonyl, $C_{1-4}$-alkyloxycarbonyl, N-hydroxy-methanimidamidyl, pyridinyl, furanyl, tetrazolyl, oxadiazolyl, wherein the latter may be optionally substituted with $C_{1-4}$alkyl, halo, amino, cyano, trifluoromethyl, hydroxy$C_{1-4}$alkyl, cyano-$C_{1-4}$alkyl, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, oxo, thio;

(1-f) $R^1$ is hydrogen, cyano, halo, aminocarbonyl, $C_{1-4}$alkylaminocarbonyl, arylaminocarbonyl, $C_{1-4}$alkyloxycarbonyl, N-hydroxy-methanimidamidyl, pyridinyl, furanyl, tetrazolyl, oxadiazolyl, wherein the latter may be optionally substituted with $C_{1-4}$alkyl, trifluoromethyl, amino$C_{2-6}$alkenyl, mono- or di($C_{1-4}$alkyl)amino$C_{2-6}$alkenyl, oxo, thio;

(1-g) $R^1$ is cyano, aminocarbonyl, $C_{1-4}$alkylaminocarbonyl;
(1-h) $R^1$ is cyano, methyloxycarbonyl, methylaminocarbonyl, ethyloxycarbonyl or ethylaminocarbonyl; or
(1-i) $R^1$ is cyano and ethylaminocarbonyl; or
(1-j) $R^1$ is cyano.

Further embodiments of the present invention are those compounds of formula (I) or any of the subgroups of compounds of formula (I) specified herein, wherein:
(2) X is O or S; or
(2-a) X is O;

Further embodiments of the present invention are those compounds of formula (I) or any of the subgroups of compounds of formula (I) specified herein, wherein:
(3) X is $NR^2$, wherein $R^2$ is hydrogen, $C_{1-10}$alkyl, $C_{2-10}$alkenyl, $C_{3-7}$cycloalkyl, wherein said $C_{1-10}$alkyl $C_{2-10}$alkenyl and $C_{3-7}$cycloalkyl, each individually and independently, may be optionally substituted with a substituent selected from the group consisting of cyano, $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $N(R^{16a}R^{16b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-ylcarbonyl, thiomorpholin-1-ylcarbonyl, 1-oxothiomorpholin-1-ylcarbonyl and 1,1-dioxo-thiomorpholin-1-ylcarbonyl; or
$R^2$ is aryl substituted with a radical —COOR$^4$; or
$R^2$ is $C_{1-10}$alkyl, $C_{2-10}$alkenyl, $C_{3-7}$cycloalkyl, wherein said $C_{1-10}$alkyl, $C_{2-10}$alkenyl, $C_{3-7}$cycloalkyl, each individually and independently, is substituted with aryl wherein said aryl is substituted with a radical —COOR$^4$; or
wherein said $C_{1-10}$alkyl, $C_{2-10}$alkenyl, $C_{3-7}$cycloalkyl, each individually and independently, is substituted with a radical selected from —$NR^{5a}$—C(=$NR^{5b}$)—$NR^{5c}R^{5d}$, —$NR^{5a}$—C(=$NR^{5e}$)—$R^{5f}$, —O—$NR^{5a}$—C(=$NR^{5b}$)—$NR^{5c}R^{5d}$, —O—$NR^{5a}$—C(=$NR^{5e}$)—$R^{5f}$, -sulfonyl-$R^6$, —$NR^7R^8$, —$NR^9R^{10}$, a radical

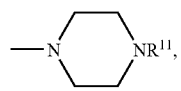
(a-1)

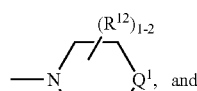
(a-2)
and

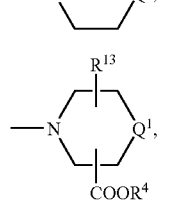
(a-3)

wherein
each $Q^1$ independently is a direct bond, —CH$_2$—, or —CH$_2$H$_2$—;
each $R^4$ independently is hydrogen, $C_{1-4}$alkyl, aryl$C_{1-4}$alkyl;

each $R^{5a}$, $R^{5b}$, $R^{5c}$, $R^{5d}$ independently is hydrogen, $C_{1-4}$alkyl or aryl$C_{1-4}$alkyl;
each $R^{5e}$, $R^{5f}$ independently is hydrogen, $C_{1-4}$alkyl or aryl$C_{1-4}$alkyl, or $R^{5e}$ and $R^{5f}$, taken together may form a bivalent alkylene radical of formula —CH$_2$—CH$_2$— or —CH$_2$—CH$_2$—CH$_2$—;
$R^6$ is $C_{1-4}$alkyl, —N($R^{5a}R^{5b}$), $C_{1-4}$alkyloxy, pyrrolidin-1-yl, piperidin-1-yl, homopiperidin-1-yl, piperazin-1-yl, 4-($C_{1-4}$alkyl)-piperazin-1-yl, morpholin-4-yl-, thiomorpholin-4yl-, 1-oxothiomorpholin-4-yl and 1,1-dioxothiomorpholinyl-4-yl;
$R^7$ is hydrogen or hydroxy$C_{1-4}$alkyl;
$R^8$ is hydroxy$C_{1-4}$alkyl;
$R^9$ is hydrogen or $C_{1-4}$alkyl;
$R^{10}$ is Het$_1$, Het$_2$ or a radical

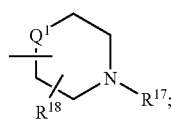
(a-6)

$R^{11}$ is aryl, aryl$C_{1-4}$alkyl, formyl, $C_{1-4}$alkylcarbonyl, arylcarbonyl, aryl$C_{1-4}$alkylcarbonyl, $C_{1-4}$alkyloxycarbonyl, aryl$C_{1-4}$alkyloxycarbonyl, $R^{5a}R^{5b}$N-carbonyl, hydroxy$C_{1-4}$alkyl, $C_{1-4}$alkyloxy$C_{1-4}$alkyl, aryl$C_{1-4}$alkyloxy$C_{1-4}$alkyl, aryloxy$C_{1-4}$alkyl, Het$_2$;
$R^{12}$ is hydroxy, $C_{1-4}$alkyl, aryl$C_{1-4}$alkyl, $C_{1-4}$alkyloxy, aryl$C_{1-4}$alkyloxy, oxo, spiro($C_{2-4}$alkylenedioxy), spiro(di$C_{1-4}$alkyloxy), —$NR^{5a}R^{5b}$;
$R^{13}$ is hydrogen, hydroxy, $C_{1-4}$alkyl, $C_{1-4}$alkyloxy, or aryl$C_{1-4}$alkyloxy; or
$R^2$ is a radical of formula:

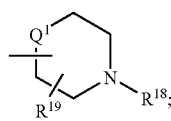
(b-1)

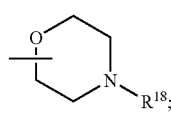
(b-2)

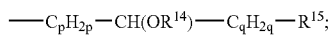
(b-3)
—$C_pH_{2p}$—CH(OR$^{14}$)—$C_qH_{2q}$—$R^{15}$;

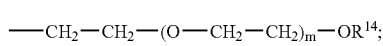
(b-4)
—CH$_2$—CH$_2$—(O—CH$_2$—CH$_2$)$_m$—OR$^{14}$;

(b-5)
—CH$_2$—CH$_2$—(O—CH$_2$—CH$_2$)$_m$—NR$^{5a}$R$^{5b}$;

wherein in radical (b-3) one of the hydrogen atoms in (-13 $C_pH_{2p}$— and one of the hydrogen atoms in —CH(OR$^{14}$)-13 $C_qH_{2q}$—, that is not part of $R^{14}$, may be replaced by a direct bond or a $C_{1-4}$alkanediyl group;
p is 1, 2 or 3;
q is 0, 1, 2 or 3;
m is 1 to 10;
each $R^{14}$ independently is hydrogen, $C_{1-4}$alkyl, aryl $C_{1-4}$alkyl, aryl, $C_{1-4}$alkylcarbonyl, —SO$_3$H, —PO$_3$H$_2$;
$R^{15}$ is a substituent selected from the group consisting of cyano, $NR^{16a}R^{16b}$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furayl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxy-carbonyl, $C_{1-4}$alkylcarbonyl, $N(R^{16a}R^{16b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-yl-carbonyl, thiomorpholin-1-yl-carbonyl, 1-oxothiomorpholin-1-ylcarbonyl and 1,1-dioxo-thiomorpholin-1-ylcarbonyl; and wherein $R^{15}$ may additionally be aryl substituted with a radical —$COOR^4$; or a radical selected from —$NR^{5a}$—$C(=NR^{5b})$—$NR^{5c}R^{5d}$, —$NR^{5a}$—$C(=NR^{5e})$—$R^{5f}$, —O—$NR^{5a}$—$C(=NR^{5b})$—$NR^{5c}R^{5d}$, —O—$NR^{5a}$—$C(=NR^{5e})$—$R^{5f}$, -sulfonyl-$R^6$, —$NR^7R^8$, —$NR^9R^{10}$, a radical (a-1), (a-2), (a-3); wherein $R^4$, $R^{5a}$, $R^{5b}$, $R^{5c}$, $R^{5d}$, $R^6$, $R^7$, $R^8$, $R^9$, $R^{10}$, and the radicals (a-1), (a-2), (a-3) independently are as defined above;

$R^{16a}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

$R^{16b}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

each $R^{18}$ independently is hydrogen, $C_{1-4}$alkyl or aryl$C_{1-4}$alkyl;

$R^{19}$ is hydrogen, hydroxy, $C_{1-4}$alkyl or a radical —$COOR^4$; or wherein Further embodiments of the present invention are those compounds of formula (I) or any of the subgroups of compounds of formula (I) specified herein, wherein:

(4-a) X is $NR^2$ wherein $R^2$ is $C_{1-10}$alkyl, $C_{2-10}$alkenyl, $C_{3-7}$cycloalkyl, each of the former three radicals being independently substituted with aryl, wherein said aryl is substituted with a radical —$COOR^4$; or (4-a-1) X is $NR^2$ wherein $R^2$ is $C_{1-10}$alkyl being substituted with aryl, wherein said aryl is substituted with a radical —$COOR^4$; or (4-a-2) X is $NR^2$ wherein $R^2$ is $C_{1-10}$alkyl being substituted with phenyl substituted with a radical —$COOR^4$; or (4-a-3) X is $NR^2$ wherein $R^2$ is $C_{1-10}$alkyl being substituted with phenyl substituted in para position with a radical —$COOR^4$; or wherein (4-b) X is $NR^2$ wherein $R^2$ is $C_{1-10}$alkyl, $C_{2-10}$alkenyl, $C_{3-7}$cycloalkyl, each of the former three radicals being independently substituted with a radical selected from —$NR^{5a}$—$C(=NR^{5b})$—$NR^{5c}R^{5d}$, —O—$NR^{5a}$—$C(=NR^{5b})$—$NR^{5c}R^{5d}$, -sulfonyl-$R^6$, —$NR^7R^8$, —$NR^9R^{10}$, a radical (a-1), (a-2), (a-3), (a-4) and (a-5);

(4-b-1) X is $NR^2$ wherein $R^2$ is $C_{1-10}$alkyl substituted with a radical selected from —$NR^{5a}$—$C(=NR^{5b})$—$NR^{5c}R^{5d}$, —O—$NR^{5a}$—$C(=NR^{5b}NR^{5c}R^{5d}$, -sulfonyl-$R^6$, —$NR^7R^8$, —$NR^9R^{10}$, a radical (a-1), (a-2), (a-3), (a-4) and (a-5);

(4-b-2) X is $NR^2$ wherein $R^2$ is $C_{1-10}$alkyl substituted with a radical selected from —$NR^{5a}$—$C(=NR^{5b})$—$NR^{5c}R^{5d}$, —O—$NR^{5a}$—$C(=NR^{5b})$—$NR^{5c}R^{5d}$, -sulfonyl-$R^6$, —$NR^7R^8$, —$NR^9R^{10}$, a radical (a-1), (a-2) and (a-3);

(4-b-3) X is $NR^2$ wherein $R^2$ is $C_{1-6}$alkyl substituted with the radicals mentioned in (4-b-1) or in (4-b-2)

(4-b-4) X is $NR^2$, wherein $R^2$ is $C_{1-6}$alkyl substituted with a radical selected from —$NR^{5a}$—$C(=NR^{5b})$—$NR^{5c}R^{5d}$, —$NR^7R^8$, —$NR^9R^{10}$, a radical (a-1), (a-2), (a-3), (a-4) and (a-5);

(4-b-5) X is $NR^2$, wherein $R^2$ is $C_{1-6}$alkyl substituted with a radical selected from —$NR^{5a}$—$C(=NR^{5b})$—$NR^{5c}R^{5d}$, —$NR^7R^8$, —$NR^9R^{10}$, a radical (a-1), (a-2), (a-3);

(4-c) X is $NR^2$ wherein $R^2$ is a radical (b-1);

(4-c-1) X is $NR^2$ wherein $R^2$ is a radical (b-1), wherein $R^{19}$ is hydrogen or —$COOR^4$ and wherein $Q^1$ in radical (b-1) is a direct bond or —$CH_2$—;

(4-d) X is $NR^2$ wherein $R^2$ is a radical (b-2);

(4-d-1) X is $NR^2$ wherein $R^2$ is a radical (b-2), wherein $Q^2$ is O;

(4-e) X is $NR^2$ wherein $R^2$ is a radical (b-3) wherein q is 1, 2 or 3;

(4-e-1) X is $NR^2$ wherein $R^2$ is a radical (b-3) wherein p is 1 and q is 1;

(4-e-2) X is $NR^2$ wherein $R^2$ is a radical (b-3) wherein $R^{15}$ is cyano, $NR^{16a}R^{16b}$, pyrrolidinyl, piperidinyl, 4-($C_{1-4}$alkyl)-piperazinyl, morpholinyl, aryl, imidazolyl, pyridyl, hydroxycarbonyl, $N(R^{16a}R^{16b})$carbonyl, $C_{1-4}$alkyloxycarbonyl 4-($C_{1-4}$alkyl)-piperazin-1-ylcarbonyl, —$NR^7R^8$, —$NR^9R^{10}$, a radical (a-1), (a-2), (a-3), (a-4) or (a-5);

(4-e-3) X is $NR^2$ wherein $R^2$ is a radical (b-3) wherein $R^{14}$ is hydrogen and $R^{15}$ is cyano, $NR^{16a}R^{16b}$, pyrrolidinyl, piperidinyl, 4-($C_{1-4}$alkyl)-piperazinyl, morpholinyl, aryl, imidazolyl, pyridyl, hydroxycarbonyl, $N(R^{16a}R^{16b})$carbonyl, $C_{1-4}$alkyloxycarbonyl or 4-($C_{1-4}$alkyl)-piperazin-1-ylcarbonyl;

(4-e-4) X is $NR^2$ wherein $R^2$ is a radical (b-3) wherein p is 1 and q is 1, and $R^{15}$ is cyano, $NR^{16a}R^{16b}$, pyrrolidinyl, piperidinyl, 4-morpholinyl, aryl, imidazolyl, pyridyl, hydroxycarbonyl or $N(R^{16a}R^{16b})$carbonyl;

(4-e-5) X is $NR^2$ wherein $R^2$ is a radical (b-3) $R^{15}$ is $NR^{16a}R^{16b}$, pyrrolidinyl, piperidinyl, 4-morpholinyl;

(4-e-6) X is $NR^2$ wherein $R^2$ is a radical (b-3) wherein $R^{15}$ is pyrrolidinyl, piperidinyl, 4-morpholinyl;

(4-e-6) X is $NR^2$ wherein $R^2$ is a radical (b-3) wherein $R^{15}$ is pyrrolidinyl;

(4-f) X is $NR^2$ wherein $R^2$ is a radical (b-4) wherein m is 1-6;

(4-f-1) X is $NR^2$ wherein $R^2$ is a radical (b-4) wherein $R^{14}$ is hydrogen or $C_{1-4}$alkyl;

(4-f-2) X is $NR^2$ wherein $R^2$ is a radical (b-4) wherein m is 1-5 and $R^{14}$ is hydrogen or $C_{1-4}$alkyl;

(4-g) X is $NR^2$ wherein $R^2$ is a radical (b-5);

(4-g-1) X is $NR^2$ wherein $R^2$ is a radical (b-5) wherein m is 1-5;

(4-h) X is $NR^2$, wherein $R^2$ is hydrogen, $C_{1-10}$alkyl, which may be optionally substituted with a substituent selected from the group consisting of cyano, $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $N(R^{16a}R^{16b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-ylcarbonyl, thiomorpholin-1-ylcarbonyl, 1-oxothiomorpholin-1-ylcarbonyl and 1,1-dioxo-thiomorpholin-1-ylcarbonyl;

(4-h-1) X is $NR^2$, wherein $R^2$ is hydrogen, $C_{1-10}$alkyl, which may be optionally substituted with cyano, $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, pyridyl, pyrimidinyl, hydroxycarbonyl, $C_{1-4}$alkylcarbonyl, $N(R^{16a}R^{16b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-yl-carbonyl, thiomorpholin-1-ylcarbonyl;

(4-h-2) X is $NR^2$, wherein $R^2$ is hydrogen, $C_{1-10}$alkyl, which may be optionally substituted with cyano, $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, pyridyl, pyrimidinyl, hydroxycarbonyl, $C_{1-4}$alkylcarbonyl, $N(R^{16a}R^{16b})$carbonyl, $C_{1-4}$alkyloxycarbonyl;

(4-h-3) X is $NR^2$, wherein $R^2$ is hydrogen, $C_{1-6}$alkyl, which may be optionally substituted with cyano, $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl, aryl, hydroxycarbonyl, $C_{1-4}$alkylcarbonyl;

(4-h-4) X is $NR^2$, wherein $R^2$ is hydrogen, $C_{1-6}$alkyl, which may be optionally substituted with $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl;

(4-h-5) X is $NR^2$, wherein $R^2$ is $C_{1-6}$alkyl, which may be optionally substituted with $N(R^{16a}R^{16b})$, pyrrolidinyl, piperidinyl;

(4-h-6) X is $NR^2$, wherein $R^2$ is $C_{1-6}$alkyl, which may be optionally substituted with $N(R^{16a}R^{16b})$, pyrrolidinyl.

Further embodiments of the present invention are those compounds of formula (I) or any of the subgroups of compounds of formula (I) specified herein, wherein (5) $R^3$ is a monocyclic or bicyclic aromatic heterocyclic aromatic ring system wherein the ring system contains one oxygen, sulfur or nitrogen, and optionally one, two or three further nitrogen atoms and wherein the remaining ring members are carbon atoms; optionally substituted with one, two, three, or four substituents each independently selected from halo, cyano, nitro, $C_{1-6}$alkyl, hydroxy$C_{1-6}$alkyl, $C_{1-4}$alkoxy$C_{1-6}$alkyl, $(R^{5a})(R^{5b})$N—$C_{1-4}$alkyl, $CF_3$, $C_{3-7}$cycloalkyl, formyl, $C_{1-6}$alkylcarbonyl, a radical —$COOR^4$, $(R^{5a})(R^{5b})$N-carbonyl, hydroxy, $C_{1-6}$alkyloxy, $(R^{5a})(R^{5b})$N-mercapto, $C_{1-6}$alkylthio, $C_{1-6}$alkylsulfonyl, aryl, —CH(=N—O—$R^{5a}$), —C(=NH)—NH—$R^{5a}$.

(5-a) $R^3$ is pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl; optionally substituted with one, two, three, or four substituents each independently selected from the substituents listed above in the definition of $R^3$;

(5-b) $R^3$ is pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, carbazolyl, acridinyl, phenothiazinyl, phenoxazinyl; optionally substituted with one, two, or three substituents each independently selected from halo, cyano, nitro, $C_{1-6}$alkyl, hydroxy$C_{1-6}$alkyl, $C_{1-4}$alkoxy$C_{1-6}$alkyl, $(R^{5a})(R^{5b})$N—$C_{1-4}$alkyl, polyhalo$C_{1-6}$alkyl, $C_{3-7}$cycloalkyl, formyl, $C_{1-6}$alkylcarbonyl, a radical —$COOR^4$, $(R^{5a})(R^{5b})$N-carbonyl, hydroxy, $C_{1-6}$alkyloxy, $(R^{5a})(R^{5b})$N-,mercapto, $C_{1-6}$alkylthio, $C_{1-6}$alkylsulfonyl, $C_{1-6}$alkylsulfinyl, aryl, —CH(=N—O—$R^{5a}$), —C(=NH)—NH—$R^{5a}$;

(5-c) $R^3$ is pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, imidazopyridyl, quinolinyl, isoquinolinyl, phthalazinyl, quinoxalinyl, quinazolinyl; optionally substituted with one, two, or three substituents each independently selected from halo, cyano, nitro, $C_{1-6}$alkyl, hydroxy$C_{1-6}$alkyl, $C_{1-4}$alkoxy$C_{1-6}$alkyl, $CF_3$, $C_{3-7}$cycloalkyl, $C_{1-6}$alkylcarbonyl, —$COOR^4$, $(R^{5a})(R^{5b})$N-carbonyl, hydroxy, $C_{1-6}$alkyloxy, $(R^{5a})(R^{5b})$N—, mercapto, $C_{1-6}$alkylthio, $C_{1-6}$alkylsulfonyl;

(5-d) $R^3$ is furyl, thienyl, imidazolyl, oxazolyl, thiazolyl, pyrazolyl, triazolyl, pyridyl, pyrimidinyl, benzofuryl, isobenzofuryl, benzothienyl, isobenzothienyl, indolyl, benzoxazolyl, benzimidazolyl, benzisoxazolyl, imidazopyridyl, purinyl, quinolinyl, isoquinolyl; optionally substituted with one, two, or three substituents each independently selected from halo, cyano, nitro, $C_{1-6}$alkyl, $CF_3$, —COOR$^4$, (R$^{5a}$)(R$^{5b}$)(N-carbonyl, hydroxy, $C_{1-6}$alkyloxy, (R$^{5a}$)(R$^{5b}$)N-, $C_{1-6}$alkylthio, $C_{1-6}$alkylsulfonyl;

(5-e) R$^3$ is furyl, thienyl, pyridyl, pyrimidinyl, benzofuryl, benzothienyl, indolyl, imidazopyridyl, purinyl, optionally substituted with one or two substituents selected from halo, cyano, $C_{1-6}$alkyl, $CF_3$, —COOR$^4$, (R$^{5a}$)(R$^{5b}$)N-carbonyl, hydroxy, $C_{1-6}$alkyloxy, $C_{1-6}$alkylthio, $C_{1-6}$alkylsulfonyl;

(5-f) R$^3$ is furyl, thienyl, pyridyl, indolyl, imidazopyridyl, optionally substituted with one or two substituents selected from halo, cyano, $C_{1-6}$alkyl, $CF_3$, —COOR$^4$, (R$^{5a}$)(R$^{5b}$)N-carbonyl, $C_{1-6}$alkyloxy, $C_{1-6}$alkylthio, $C_{1-6}$alkylsulfonyl.

Further embodiments of the present invention are those compounds of formula (I) or any of the subgroups of compounds of formula (I) specified herein, wherein:

(6) R$^4$ is hydrogen or $C_{1-4}$alkyl; or wherein (6-a) R$^4$ is hydrogen.

Further embodiments of the present invention are those compounds of formula (I) or any of the subgroups of compounds of formula (I) specified herein, wherein:

(7) each R$^{5a}$, R$^{5b}$, R$^{5c}$, R$^{5d}$, R$^{5e}$ and R$^{5f}$ independently is hydrogen or $C_{1-4}$alkyl; or R$^{5e}$ and R$^{5f}$, taken together may form a bivalent alkanediyl radical of formula —CH$_2$—CH$_2$— or —CH$_2$—CH$_2$—CH$_2$—;

(7-a) each R$^{5a}$, R$^{5b}$, R$^{5c}$, R$^{5d}$, R$^{5e}$ and R$^{5f}$ independently is hydrogen or $C_{1-4}$alkyl;

(7-b) each R$^{5a}$, R$^{5b}$, R$^{5c}$, R$^{5d}$, R$^{5e}$ and R$^{5f}$ independently is hydrogen.

Further embodiments of the present invention are those compounds of formula (I) or any of the subgroups of compounds of formula (I) specified herein, wherein:

(8) R$^6$ is $C_{1-4}$alkyl, —N(R$^{5a}$R$^{5b}$), $C_{1-4}$alkyloxy, pyrrolidin-1-yl, piperidin-1-yl, homopiperidin-1-yl, piperazin-1-yl, 4$C_{1-4}$alkyl)-piperazin-1-yl, morpholin-4-yl-;

(8-a) R$^6$ is $C_{1-4}$alkyl, —N(R$^{5a}$R$^{5b}$), $C_{1-4}$alkyloxy, pyrrolidin-1-yl, piperidin-1-yl, morpholin-4-yl-;

(8-b) R$^6$ is $C_{1-4}$alkyl, —N(R$^{5a}$R$^{5b}$), pyrrolidin-1-yl, piperidin-1-yl, morpholin-4-yl-; wherein R$^{5a}$ and R$^{5b}$ independently are hydrogen or $C_{1-4}$alkyl.

Other embodiments of the present invention are those compounds of formula (I) or any of the subgroups of compounds of formula (I) specified herein, wherein one or more of the following restrictions apply:

(9-a) R$^7$ is hydrogen or hydroxy$C_{1-4}$alkyl;

(9-b) R$^8$ is hydroxy$C_{1-4}$alkyl;

(9-c) R$^9$ is hydrogen.

Still other embodiments of the present invention are those compounds of formula (I) or any of the subgroups of compounds of formula (I) specified herein, wherein:

(10) R$^{10}$ is Het$_1$, pyridyl, pyrimidinyl or a radical (a-6);

(10-a) R$^{10}$ is imidazolyl, isoxazolyl, pyrazolyl, triazolyl, each of which may be optionally substituted with $C_{1-4}$alkyl; or R$^{10}$ is pyrimidyl or pyrimidinyl or a radical (a-6);

(10-b) R$^{10}$ is pyrimidyl, pyrimidinyl or a radical (a-6);

(10-c) R$^{10}$ is a radical (a-6).

Still other embodiments of the present invention are those compounds of formula (I) or any of the subgroups of compounds of formula (I) specified herein, wherein:

(11) R$^{11}$ is aryl, aryl$C_{1-4}$alkyl, formyl, $C_{1-4}$alkylcarbonyl, arylcarbonyl, $C_{1-4}$alkyloxycarbonyl, aryl$C_{1-4}$alkyloxycarbonyl, mono- and di$C_{1-4}$alkylaminocarbonyl, $C_{1-4}$alkyloxy$C_{1-4}$alkyl, aryl$C_{1-4}$alkyloxy$C_{1-4}$alkyl, pyridyl or pyrimidinyl;

(11-a) R$^{11}$ is aryl, aryl$C_{1-4}$alkyl, formyl, $C_{1-4}$alkylcarbonyl, arylcarbonyl, $C_{1-4}$alkyloxycarbonyl, $C_{1-4}$alkyloxy$C_{1-4}$alkyl, aryl$C_{1-4}$alkyloxy$C_{1-4}$alkyl, pyridyl or pyrimidinyl.

(11-b) R$^{11}$ is aryl, $C_{1-4}$alkylcarbonyl, $C_{1-4}$alkyloxycarbonyl, hydroxy$C_{1-4}$alkyl or pyridyl.

Still other embodiments of the present invention are those compounds of formula (I) or any of the subgroups of compounds of formula (I) specified herein, wherein:

(12) R$^{12}$ is hydroxy, $C_{1-4}$alkyl, $C_{1-4}$alkyloxy, oxo, spiro($C_{2-4}$alkanediyldioxy), spiro(di$C_{1-4}$alkyloxy), —NR$^{5a}$R$^{5b}$;

(12-a) when in radical (a-2) one R$^{12}$ radical is present, R$^{12}$ is hydroxy, $C_{1-4}$alkyl, $C_{1-4}$alkyloxy, oxo, —NR$^{5a}$R$^{5b}$; or when in radical (a-2) two R$^{12}$ radicals are present both independently are $C_{1-4}$alkyl, spiro($C_{2-4}$alkanediyldioxy) or spiro(di$C_{1-4}$alkyloxy); and (12-b) R$^{12}$ is hydroxy or $C_{1-4}$alkyl.

Still other embodiments of the present invention are those compounds of formula (I) or any of the subgroups of compounds of formula (I) specified herein, wherein one or more of the following restrictions apply:

(13-a) Q$^1$ is a direct bond or —CH$_2$—; or (13-b) Q$^2$ is O or S; or (13-b-1) Q$^2$ is O.

Still other embodiments of the present invention are those compounds of formula (I) or any of the subgroups of compounds of formula (I) specified herein, wherein one or more of the following restrictions apply:

(14-a) R$^{13}$ is hydrogen or hydroxy;

(14-b) R$^{13a}$ is $C_{1-4}$alkyl;

(14-c) R$^{13b}$ is hydrogen;

Still other embodiments of the present invention are those compounds of formula (I) or any of the subgroups of compounds of formula (I) specified herein, wherein:

(15) R$^{14}$ is hydrogen, $C_{1-4}$alkyl or aryl$C_{1-4}$alkyl;

(15-a) R$^{14}$ is hydrogen or $C_{1-4}$alkyl;

(15-b) R$^{14}$ is hydrogen.

Still further embodiments of the present invention are those compounds of formula (I) or any of the subgroups of compounds of formula (I) specified herein, wherein:

(16) R$^{15}$ is selected from the group consisting of cyano, NR$^{16a}$R$^{16b}$, pyrrolidinyl, piperidinyl, homopiperidinyl, piperazinyl, 4-($C_{1-4}$alkyl)-piperazinyl, 4-($C_{1-4}$alkylcarbonyl)-piperazinyl, 4-($C_{1-4}$alkyloxycarbonyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxy-carbonyl, $C_{1-4}$alkylcarbonyl, N(R$^{16a}$R$^{16b}$)carbonyl, $C_{1-4}$alkyloxycarbonyl, pyrrolidin-1-ylcarbonyl, piperidin-1-ylcarbonyl, homopiperidin-1-ylcarbonyl, piperazin-1-yl-carbonyl, 4-($C_{1-4}$alkyl)-piperazin-1-ylcarbonyl, morpholin-1-yl-carbonyl, thiomorpholin-1-yl-carbonyl, 1-oxothiomorpholin-1-ylcarbonyl and 1,1-dioxo-thiomorpholin-1-ylcarbonyl; or R$^{15}$ may additionally be aryl substituted with a radical —COOR$^4$; or a radical selected from —NR$^{5a}$—C(=NR$^{5b}$)—NR$^{5c}$R$^{5d}$, —NR$^{5a}$—C(=NR$^{5c}$)—R$^{5f}$, —O—NR$^{5a}$—C(=NR$^{5b}$)—NR$^{5c}$R$^{5d}$, —O—NR$^{5a}$—C(=NR$^{5e}$)—R$^{5f}$, -sulfonyl-R$^6$, —NR$^7$R$^8$, —NR$^9$R$^{10}$, a radical (a-1), (a-2), (a-3);

(16-a) R$^{15}$ is selected from the group consisting of cyano, NR$^{16a}$R$^{16b}$, pyrrolidinyl, piperidinyl, homopiperidinyl, piperazinyl, 4-($C_{1-4}$alkyl)-piperazinyl, 4-($C_{1-4}$alkylcarbonyl)-piperazinyl, 4-($C_{1-4}$alkyloxycarbonyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, N(R$^{16a}$R$^{16b}$)carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-ylcarbonyl, thiomorpholin-1-yl-carbonyl, 1-oxothiomorpholin-1-ylcarbonyl and 1,1-dioxo-thiomorpholin-1-ylcarbonyl;

(16-b) $R^{15}$ is selected from the group consisting of cyano, $NR^{16a}R^{16b}$, pyrrolidinyl, piperidinyl, homopiperidinyl, piperazinyl, 4-($C_{1-4}$alkyl)-piperazinyl, 4-($C_{1-4}$alkylcarbonyl)-piperazinyl, 4-($C_{1-4}$alkyloxycarbonyl)-piperazinyl, morpholinyl, thiomorpholinyl, 1-oxothiomorpholinyl, 1,1-dioxo-thiomorpholinyl, aryl, hydroxy-carbonyl, $C_{1-4}$alkylcarbonyl, $N(R^{16a}R^{16b})$carbonyl, $C_{1-4}$alkyloxycarbonyl;

(16-c) $R^{15}$ is selected from the group consisting of $NR^{16a}R^{16b}$, pyrrolidinyl, piperidinyl, homopiperidinyl, piperazinyl, 4-($C_{1-4}$alkyl)-piperazinyl, 4-($C_{1-4}$alkylcarbonyl)-piperazinyl, morpholinyl, thiomorpholinyl, 1-oxothiomorpholinyl, 1,1-dioxo-thiomorpholinyl;

(16-d) $R^{15}$ is selected from the group consisting of $NR^{16a}R^{16b}$, pyrrolidinyl, piperidinyl, piperazinyl, 4-($C_{1-4}$alkyl)-piperazinyl, morpholinyl, thiomorpholinyl, 1,1-dioxo-thiomorpholinyl;

(16-e) $R^{15}$ is selected from the group consisting of pyrrolidinyl, piperidinyl.

Further embodiments of the present invention are those compounds of formula (I) or any of the subgroups of compounds of formula (I) specified herein, wherein:

(17) $R^{16a}$ and $R^{16b}$ independently from one another are hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxothiomorpholinyl and aryl;

(17-a) $R^{16a}$ and $R^{16b}$ independently from one another are hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl;

(17-b) $R^{16a}$ and $R^{16b}$ independently from one another are hydrogen or $C_{1-4}$alkyl.

Further embodiments of the present invention are those compounds of formula (I) or any of the subgroups of compounds of formula (I) specified herein, wherein:

(18) $R^{17a}$ and $R^{17b}$ independently from one another are hydrogen, $C_{1-4}$alkyl or aryl$C_{1-4}$alkyl; or $R^{17a}$ and $R^{17b}$ together with the nitrogen atom to which they are attached form a pyrrolidinyl, piperidinyl, homopiperidinyl, morpholinyl, thiomorpholinyl, 1,1-dioxo-thiomorpholinyl, piperazinyl or 4-$C_{1-4}$alkyl-piperazinyl ring;

(18-a) $R^{17a}$ and $R^{17b}$ independently from one another are hydrogen, $C_{1-4}$alkyl or aryl-$C_{1-4}$alkyl;

(18-b) $R^{17a}$ and $R^{17b}$ independently from one another are hydrogen, $C_{1-4}$alkyl or aryl-$C_{1-4}$alkyl.

Further embodiments of the present invention are those compounds of formula (I) or any of the subgroups of compounds of formula (I) specified herein, wherein:

(19) each $R^{18}$ independently is hydrogen, $C_{1-4}$alkyl or aryl$C_{1-4}$ alkyl;

(19-a) each $R^{18}$ independently is hydrogen.

Further embodiments of the present invention are those compounds of formula (I) or any of the subgroups of compounds of formula (I) specified herein, wherein:

(20) $R^{19}$ is hydrogen, $C_{1-4}$alkyl or a radical —$COOR^4$;

(20-a) $R^{19}$ is hydrogen.

Further embodiments of the present invention are those compounds of formula (I) or any of the subgroups of compounds of formula (I) specified herein, wherein:

(21) aryl is phenyl optionally substituted with one or more substituents each individually selected from the group consisting of $C_{1-6}$alkyl, $C_{1-4}$alkoxy, cyano, nitro;

(21-a) aryl is phenyl optionally substituted with one, two or three substituents each independently selected from $C_{1-6}$alkyl, $C_{1-4}$alkoxy, cyano and nitro;

Further embodiments of the present invention are those compounds of formula (I) or any of the subgroups of compounds of formula (I) specified herein, wherein:

(22) $Het_1$ is an aromatic 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{3-7}$cycloalkyl, halo, cyano, trifluoromethyl, cyano$C_{1-4}$alkyl, mono- or di($C_{1-4}$alkyl)amino, mono- or di($C_{1-4}$alkyl)amino$C_{2-6}$alkenyl, isoxazolyl, aryl, hydroxycarbonyl, $C_{1-4}$alkyloxycarbonyl, oxo, thio; and wherein the foregoing isoxazolyl may optionally be substituted with $C_{1-4}$alkyl;

(22-a) $Het_1$ is furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, each of which individually and independently may be optionally substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl.

Further embodiments of the present invention are those compounds of formula (I) or any of the subgroups of compounds of formula (I) specified herein, wherein:

(23) $Het_2$ is pyridyl or pyrimidinyl both optionally substituted with $C_{1-4}$-alkyl.

(23-a) $Het_2$ is pyridyl or pyrimidinyl;

(23-b) $Het_2$ is pyridyl.

Further embodiments of the present invention are those compounds of formula (I) or any of the subgroups of compounds of formula (I) specified herein, wherein:

(24) p is 1, 2;

(24-a) p is 1.

Further embodiments of the present invention are those compounds of formula (I) or any of the subgroups of compounds of formula (I) specified herein, wherein:

(25) p is 1, 2, 3;

(25-a) q is 1, 2;

(25-b) q is 1.

Further embodiments of the present invention are those compounds of formula (I) or any of the subgroups of compounds of formula (I) specified herein, wherein:
(26) m is 1-8;
(26-a) m is 1-6;
(26-b) m is 1-4;
(26-c) m is 1-3;
(26-d) m is 1-2.

Further embodiments of the present invention are those compounds of formula (I) or any of the subgroups of compounds of formula (I) specified herein, wherein:
(27) -a¹=a²-a³=a⁴- represents a bivalent radical of formula —CH=CH—CH=CH— (c-1);

—N=CH—CH=CH— (c-2);

—CH=N—CH=CH— (c-3);

—CH=CH—N=CH— (c-4);

—CH=CH—CH=N— (c-5);

wherein one of the hydrogen atoms in (c-1) may be replaced by a radical $C_{1-6}$-alkyl, $C_{1-4}$alkoxy, halo, hydroxy, $(R^{5g})(R^{5h})N—(C_{1-4}$alkanediyl)-O—, $(R^7)(R^8)N—(C_{1-4}$alkanediyl)-O—, $(R^8)(R^9)N—(C_{1-4}$alkanediyl)-O—, trifluoromethyl, cyano, a radical —COOR⁴, $(R^{5a})(R^{5b})N$-carbonyl, $(R^{5a})(R^{5b})N$-sulfonyl, formyl, $C_{1-6}$alkylcarbonyl, nitro, hydroxy$C_{1-6}$alkyl, $C_{1-4}$alkoxy$C_{1-6}$alkyl, (R⁴OOC)—$C_{1-6}$alkyl, a radical —N($R^{5a}$)($R^{5b}$), —N(R⁷)(R⁸), —N(R⁹)(R¹⁰), a radical (a-1), a radical

(a-7)

morpholinyl, thiomorpholinyl, 1-oxothiomorpholinyl, 1,1-dioxo-thiomorpholinyl, $(R^{5g})(R^{5h})N—(C_{1-4}$alkanediyl)-N($R^{5c}$)—, (R⁷)(R⁸)N—($C_{1-4}$alkanediyl)-N($R^{5c}$)—, (R⁹)(R¹⁰)N—($C_{1-4}$alkanediyl)-N($R^{5c}$)—, $C_{1-6}$alkylcarbonylamino, $C_{1-6}$alkyloxycarbonylamino, $(R^{5a})(R^{5b})N—C_{1-4}$alkyl; aryl; Het₁ or Het₂;

R²⁰ is hydrogen, hydroxy, $C_{1-4}$alkyl, aryl$C_{1-4}$alkyl, $C_{1-4}$alkyloxy, aryl$C_{1-4}$alkyloxy, oxo, spiro($C_{2-4}$alkylenedioxy), spiro(di$C_{1-4}$alkyloxy), —NR$^{5g}$R$^{5h}$;

each R$^{5g}$ or R$^{5h}$ independently is hydrogen, $C_{1-4}$alkyl or aryl$C_{1-4}$alkyl, or R$^{5g}$ and R$^{5h}$ together with the nitrogen to which they attached form a pyrrolidinyl, piperidinyl, homopiperidinyl, morfolinyl, piperazinyl or 4-$C_{1-4}$alkylpiperazinyl radical;

wherein each of said pyrrolidinyl, piperidinyl, homopiperidinyl, morfolinyl, piperazinyl or 4-$C_{1-4}$alkylpiperazinyl radical may optionally be substituted with hydroxy or oxo; or wherein one or more of the hydrogen atoms in (c-2), (c-3), (c-4) or (c-5) may be replaced with a radical selected from halo and $C_{1-6}$alkyl;

(27-a) -a¹=a²-a³=a⁴- represents a bivalent radical of formula (c-1) wherein one, two or three (or one or two; or one) of the hydrogen atoms in (c-1) may be replaced by a radical $C_{1-6}$alkyl, $C_{1-4}$alkoxy, halo, hydroxy, $(R^{5a})(R^{5b})N—(C_{1-4}$alkanediyl)oxy, trifluoromethyl, cyano, a radical —COOR⁴, $(R^{5a})(R^{5b})N$-carbonyl, $C_{1-6}$-alkylcarbonyl, nitro, hydroxy$C_{1-6}$alkyl, $C_{1-4}$alkoxy$C_{1-6}$alkyl, (R⁴OOC)—$C_{1-6}$alkyl, a radical N($R^{5a}$)($R^{5b}$), a radical (a-1), a radical (a-7), morpholinyl, $(R^{5a})(R^{5b})N—(C_{1-4}$alkanediyl)amino, $(R^{5a})(R^{5b})N—(C_{1-4}$alkanediyl)-($C_{1-4}$alkylamino), $C_{1-6}$alkylcarbonylamino, $C_{1-6}$alkyloxycarbonylamino, $(R^{5a})(R^{5b})N—C_{1-4}$alkyl; or wherein one of the hydrogen atoms in (c-2), (c-3), (c-4) or (c-5) may be replaced with a radical selected from halo and $C_{1-6}$alkyl;

(27-b) -a¹=a²-a³=a⁴- represents a bivalent radical of formula (c-1);

wherein one of the hydrogen atoms in (c-1) may be replaced by a radical $C_{1-6}$-alkyl, halo, a radical —COOR⁴, a radical —N($R^{5a}$)($R^{5b}$), $(R^{5a})(R^{5b})N—(C_{1-4}$ alkanediyl)amino, $C_{1-6}$alkyloxycarbonylamino, a radical (a-1) wherein R¹⁹ is hydrogen or $C_{1-4}$alkyl, a radical (a-7) wherein R¹⁹ is hydrogen; or -a¹=a²-a³=a⁴- represents a bivalent radical of formula (c-2), (c-3,) (c-4) or (c-5) that is unsubstituted;

(27-c) -a¹=a²-a³=a⁴- represents a bivalent radical of formula (c-1); (c-2); (c-3); (c-4); (c-5); wherein one, two or three (or one or two; or one) of the hydrogen atoms in (c-1) may be replaced by $C_{1-6}$alkyl, $C_{1-4}$alkoxy, halo, hydroxy, $(R^{5g})(R^{5h})N—(C_{1-4}$alkanediyl)-O—, cyano, —COOR⁴, $(R^{5a})(R^{5b})N$-carbonyl, $(R^{5a})(R^{5b})N$-sulfonyl, formyl, $C_{1-6}$alkylcarbonyl, nitro, hydroxy$C_{1-6}$alkyl, $C_{1-4}$alkoxy$C_{1-6}$alkyl, (R⁴OOC)—$C_{1-6}$alkyl, —N($R^{5a}$)($R^{5b}$), —N(R⁷)(R⁸), —N(R⁹)(R¹⁰), a radical (a-1), a radical (a-7), morpholinyl, thiomorpholinyl, $(R^{5g})(R^{5h})N—(C_{1-4}$alkanediyl)-N($R^{5c}$)—, $C_{1-6}$alkylcarbonylamino, $C_{1-6}$alkyloxycarbonylamino, trifluoroacetylamino, $(R^{5a})(R^{5b})N—C_{1-4}$alkyl;

wherein one of the hydrogen atoms in (c-2), (c-3), (c-4) or (c-5) may be replaced with a radical selected from halo and $C_{1-6}$alkyl;

(27-d) -a¹=a²-a³=a⁴- represents a bivalent radical of formula (c-1); wherein one, two or three (or one or two; or one) of the hydrogen atoms may be replaced by $C_{1-6}$alkyl, $C_{1-4}$alkoxy, halo, hydroxy, $(R^{5g})(R^{5h})N—(C_{1-4}$alkanediyl)-O—, a radical —COOR⁴, $(R^{5a})(R^{5b})N$-sulfonyl, —N($R^{5a}$)($R^{5b}$), —N(R⁷)(R⁸), a radical (a-1), a radical (a-7), morpholinyl, $(R^{5g})(R^{5h})N—(C_{1-4}$alkanediyl)-N($R^{5c}$)—, $C_{1-6}$alkyloxycarbonylamino, trifluoroacetylamino, $(R^{5a}(R^{5b})N—C_{1-4}$alkyl; or -a¹=a²-a³=a⁴- represents a bivalent radical of formula (c-2), (c-3), (c-4) or (c-5) that is unsubstituted;

(27-e) -a¹=a²-a³=a⁴- represents a bivalent radical of formula (c-1); wherein one or two of the hydrogen atoms may be replaced by $C_{1-6}$alkyl, $C_{1-4}$alkoxy, halo, hydroxy, $(R^{5g})(R^{5h})N—(C_{1-4}$alkanediyl)-O—, —COOR⁴, —N($R^{5a}$)($R^{5b}$), —N(R⁷)(R⁸), a radical (a-1), a radical (a-7), morpholinyl $(R^{5g})(R^{5h})N—(C_{1-4}$alkanediyl)-N($R^{5c}$)—, $C_{1-6}$alkyloxycarbonylamino, trifluoroacetylamino or -a¹=a²-a³=a⁴- represents a bivalent radical of formula (c-2), (c-3), (c-4) or (c-5) that is unsubstituted;

(27-f) -a¹=a²-a³=a⁴- represents a bivalent radical of formula (c-1); wherein one or two of the hydrogen atoms may be replaced by $C_{1-6}$alkyl $C_{1-4}$alkoxy, halo, hydroxy, $(R^{5g})(R^{5h})N—(C_{1-4}$alkanediyl)-O—, —COOR⁴, —N($R^{5a}$)($R^{5b}$), a radical (a-1), a radical (a-7), morpholinyl, $(R^{5g})(R^{5h})N—(C_{1-4}$alkanediyl)-N($R^{5c}$)—;

(27-g) -a¹=a²-a³=a⁴- represents a bivalent radical of formula (c-1); wherein one or two of the hydrogen atoms may be replaced by hydroxy, $(R^{5g})(R^{5h})N—(C_{1-4}$alkanediyl)-O—, —N($R^{5a}$)($R^{5b}$), a radical (a-1), $(R^{5g})(R^{5h})N—(C_{1-4}$ alkanediyl)-N($R^{5c}$)—;

(27-h) -a¹=a²-a³=a⁴- represents a bivalent radical of formula (c-1); wherein one or two of the hydrogen atoms may be replaced by hydroxy, $(R^{5g})(R^{5h})N$—$(C_{1-4}alkanediyl)$—$O$—, $(R^{5g})(R^{5h})N$—$(C_{1-4}alkanediyl)$-$N(R^{5c})$—;

(27-i) -$a^1$=$a^2$-$a^3$=$a^4$- represents a bivalent radical of formula (c-1); wherein one (or two) of the hydrogen atoms may be replaced by hydroxy, $(R^{5g})(R^{5h})N$—$(C_{1-4}alkanediyl)$-$N(R^{5c})$—;

(27-j) -$a^1$=$a^2$-$a^3$=$a^4$- represents a bivalent radical of formula —CH=CH—CH=CH— (i.e. a radical (c-1) wherein none of the hydrogen atoms is replaced).

Further embodiments of the present invention are those compounds of formula (I) or any of the subgroups of compounds of formula (I) specified herein, wherein:

(28) $R^{20}$ is hydrogen, hydroxy, $C_{1-4}$alkyl, spiro($C_{2-4}$alkylenedioxy), spiro(di$C_{1-4}$alkyloxy), —$NR^{5g}R^{5h}$;

(28-a) $R^{20}$ is hydrogen, hydroxy, $C_{1-4}$alkyl, spiro($C_{2-4}$alkylenedioxy), —$NR^{5g}R^{5h}$;

(28-a) $R^{20}$ is hydrogen, hydroxy, $C_{1-4}$alkyl; or (28-a) $R^{20}$ is hydrogen.

Further embodiments of the present invention are those compounds of formula (I) or any of the subgroups of compounds of formula (I) specified herein, wherein:

(29) $R^{5g}$ or $R^{5h}$ independently is hydrogen, $C_{1-4}$alkyl or aryl$C_{1-4}$alkyl, or $R^{5g}$ and $R^{5h}$ together with the nitrogen to which they attached form a pyrrolidinyl, piperidinyl, homopiperidinyl, morfolinyl, piperazinyl or 4-$C_{1-4}$alkylpiperazinyl radical; wherein each of said pyrrolidinyl, piperidinyl, homopiperidinyl, morfolinyl, piperazinyl or 4-$C_{1-4}$alkylpiperazinyl radical may optionally be substituted with hydroxy or oxo; or (29-a) $R^{5g}$ or $R^{5h}$ independently is hydrogen or $C_{1-4}$alkyl, or $R^{5g}$ and $R^{5h}$ together with the nitrogen to which they attached form a pyrrolidinyl, piperidinyl, homopiperidinyl, morfolinyl, piperazinyl or 4-$C_{1-4}$alkylpiperazinyl radical;

(29-b) $R^{5g}$ or $R^{5h}$ independently is hydrogen or $C_{1-4}$alkyl.

It is to be understood that subgroups of compounds of formula (I) comprise those groups of compounds of formula (I) wherein one or more of the above restrictions apply in whatever combination. If within a definition of a restriction one or more variables are present, each of these variables can have any of the meanings given in the restrictions relating to these variables. For example if within the restrictions for $R^2$ a radical $NR^{5a}R^{5b}$ is mentioned the radicals $R^{5a}$ and $R^{5b}$ can have any of the meanings listed in the restrictions relating to $R^{5a}$ and $R^{5b}$.

A particular group of compounds of formula (I) is this wherein $R^1$, $R^3$ and n are as specified in the definition of the compounds of formula (I); and $R^2$ is as in restriction (3); and/or -$a^1$=$a^2$-$a^3$=$a^4$- is as in restriction (27), which compounds hereafter are referred to as "compounds of formula (I-a)".

Another subgroup of compounds comprises those compounds of formula (I) as a salt, wherein the salt is selected from trifluoroacetate, fumarate, chloroacetate, methanesulfonate, oxalate, acetate and citrate.

Preferred compounds are any of the compounds listed in tables 1 and 2, more in particular the compounds having numbers 7, 9, 10, 12, 17, 20, 25-28, 30, 32, 33-37, 43.

Compounds of particular interest are;
8-Methoxy-5-methyl-1-(6-methyl-pyridin-3-yl)-2-oxo-2,5-dihydro-1H-pyrido-[3,2-b]indole-3-carbonitrile,
1-(2,8-Dimethyl-imidazo[1,2-a]pyridin-6-yl)-5-methyl-2-oxo-2,5-dihydro-1H-pyrido[3,2-b]indole-3-carbonitrile,
1-(6-Chloro-5-methyl-pyridin-3-yl)-5-methyl-2-oxo-2,5-dihydro-1H-pyrido[3,2-b]-indole-3-carbonitrile,
1-(6-Chloro-pyridin-3-yl)-8-hydroxy-5-methyl-2-oxo-2,5-dihydro-1H-pyrido[3,2-b]-indole-3-carbonitrile.

Particularly preferred compounds are:
1-(6-Chloropyridin-3-yl)-5-methyl-2-oxo-2,5-dihydro-1H-pyrido[3,2-b]indole-3-carbonitrile
5-Methyl-1-(2-methyl-imidazo[1,2-a]pyridin-6-yl)-2-oxo-2,5-dihydro-1H-pyrido-[3,2-b]indole-3-carbonitrile
5-Methyl-1-(6-methyl-pyridin-3-yl)-2-oxo-2,5-dihydro-1H-pyrido[3,2-b]indole-3-carbonitrile.

Other compounds of interest comprise the above compounds of particular interest or particularly preferred compounds and the salts and possible stereoisomers thereof; or the above compounds of interest or particularly preferred compounds and the N-oxides, salts and possible stereoisomers thereof.

The compounds of the present invention inhibit HIV reverse transcriptase and may also inhibit reverse transcriptases having similarity to HIV reverse transcriptase. Such similarity may be determined using programs known in the art including BLAST. In one embodiment, the similarity at the amino acid level is at least 25%, interestingly at least 50%, more interestingly at least 75%. In another embodiment, the similarity at the amino acid level at the binding pocket, for the compounds of the present invention, is at least 75%, in particular at least 90% as compared to HIV reverse transcriptase.

Compounds of the present invention can be tested in other lentiviruses besides HIV-1, such as, for example, SIV and HIV-2.

The compounds of the present invention may have a good selectivity as measured by the ratio between $EC_{50}$ and $CC_{50}$ as described and exemplified in the antiviral analysis example. The compounds of the present invention have also a favorable specificity. There exists a high dissociation between the activity on lentiviruses versus other retroviridae, such as MLV, and versus non-viral pathogens.

The standard of "sensitivity" or alternatively "resistance" of a HIV reverse transcriptase enzyme to a drug is set by the commercially available HIV reverse transcriptase inhibitors. Existing commercial HIV reverse transcriptase inhibitors including efavirenz, nevirapine and delavirdine may loose effectivity over time against a population of HIV virus in a patient. The reason being that under pressure of the presence of a particular HIV reverse transcriptase inhibitor, the existing population of HIV virus, usually mainly wild type HIV reverse transcriptase enzyme, mutates into different mutants which are far less sensitive to that same HIV reverse transcriptase inhibitor. If this phenomenon occurs, one talks about resistant mutants. If those mutants are not only resistant to that one particular HIV reverse transcriptase inhibitor, but also to multiple other commercially available HIV reverse transcriptase inhibitors, one talks about multi-drug resistant HIV reverse transcriptase. One way of expressing the resistance of a mutant to a particular HIV reverse transcriptase inhibitor is making the ratio between the $EC_{50}$ of said HIV reverse transcriptase inhibitor against mutant HIV reverse transcriptase over $EC_{50}$ of said HIV reverse transcriptase inhibitor against wild type HIV reverse transcriptase. Said ratio is also called fold change in resistance (FR). The $EC_{50}$ value represents the amount of the compound required to protect 50% of the cells from the cytopathogenic effect of the virus.

Many of the mutants occurring in the clinic have a fold resistance of 100 or more against the commercially available HIV reverse transcriptase inhibitors, like nevirapine, efavirenz, delavirdine. Clinically relevant mutants of the HIV reverse transcriptase enzyme may be characterized by a mutation at codon position 100, 103 and 181. As used herein a codon position means a position of an amino acid in a protein sequence. Mutations at positions 100, 103 and 181 relate to non-nucleoside RT inhibitors (D'Aquila et al. Topics in HIV medicine, 2002, 10, 11-15). Examples of such clinical relevant mutant HIV reverse transcriptases are listed in Table 1.

Table 1 List of Mutations Present in Reverse Transcriptase of the HIV Strains Used.

TABLE 1

List of mutations present in reverse transcriptase of the HIV strains used.

| | |
|---|---|
| A | Y181C |
| B | K103N |
| C | L100I; K103N |
| D | L100I; K103N |
| E | F227C |
| F | Y188L |
| G | V106A, F227L |
| H | K103N, Y181C |
| I | K101E, K103N |
| J | I31L, L100I, K103N, E138G, Y181C, L214F |
| K | K20R, E28K, M41L, E44A, D67N, L74I, K103N, V118I, D123N, S162C, Y181C, G196K, Q207E, L210W, L214F, T215Y, K219N, P225H, D250E, P272A, R277K, I293V, P297K, K311R, R358K, T376A, E399D, T400L |

An interesting group of compounds are those compounds of formula (I) having a fold resistance ranging between 0.01 and 100 against at least one mutant HIV reverse transcriptase, suitably ranging between 0.1 and 100, more suitably ranging between 0.1 and 50, and even more suitably ranging between 0.1 and 30. Of particular interest are the compounds of formula (I) showing a fold resistance against at least one mutant HIV reverse transcriptase ranging between 0.1 and 20, and even more interesting are those compounds of formula (I) showing a fold resistance against at least one mutant HIV reverse transcriptase ranging between 0.1 and 10.

An interesting group of compounds are those compounds of formula (I) having a fold resistance, determined according to the methods herein described, in the range of 0.01 to 100 against HIV species having at least one mutation in the amino acid sequence of HIV reverse transcriptase as compared to the wild type sequence (genbank accession e.g. M38432, K03455, gi 327742) at a position selected from 100, 103 and 181; in particular at least two mutations selected from the positions 100, 103 and 181. Even more interesting are those compounds within said interesting group of compounds having a fold resistance in the range of 0.1 to 100, in particular in the range 0.1 to 50, more in particular in the range 0.1 to 30. Most interesting are those compounds within said interesting group of compounds having a fold resistance in the range of 0.1 and 20, especially ranging between 0.1 and 10.

One embodiment relates to compounds of the present invention showing a fold resistance in the ranges mentioned hereinabove against at least one clinically relevant mutant HIV reverse transcriptase.

A particular subgroup of compounds are those compounds of formula (I) having an $IC_{50}$ of 1 μM or lower, suitably an $IC_{50}$ of 100 nM or lower vis-à-vis the wild type virus upon in vitro screening according to the methods described herein.

The ability of the present compounds to inhibit HIV-1, HIV-2, SIV and HIV viruses with reverse transcriptase (RT) enzymes having mutated under pressure of the currently known RT inhibitors, together with the absence of cross resistance with currently known RT inhibitors, indicate that the present compounds bind differently to the RT enzyme when compared to the known NNRTIs and NRTIs. Other indicators of a different mode of action are the ribonucleotide sensitivity of the compounds of this invention as can be shown by their increased activity when administered in the presence of ATP and by their nucleoside competitive behaviour. The compounds of this invention therefore can be classified as nucleoside competitive reverse transcriptase inhibitors.

The compounds of the present invention show antiretroviral properties, in particular against Human Immunodeficiency Virus (HIV), which is the aetiological agent of Acquired Immune Deficiency Syndrome (AIDS) in humans. The HIV virus preferably infects CD4 receptor containing cells such as human T4 cells and destroys them or changes their normal function, particularly the coordination of the immune system. As a result, an infected patient has an ever-decreasing number of T4 cells, which moreover behave abnormally. Hence, the immunological defence system is unable to combat infections and/or neoplasms and the HIV infected subject usually dies by opportunistic infections such as pneumonia, or by cancers. Other diseases associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC). The HIV virus also infects CD8-receptor containing cells. Other target cells for HIV virus include microglia, dendritic cells, B-cells and macrophages.

Due to these favourable pharmacological properties, the compounds of the present invention or any subgroup thereof may be used as a medicine against the above-mentioned diseases or in the prophylaxis thereof, or used in a method of treatment of the above-mentioned diseases or in the prophylaxis thereof. Said use as a medicine or method of treatment comprises the systemic administration to HIV-infected subjects, in particular human patients, of an amount of a compound of formula (I) or of a compound of a subgroup of compounds of formula (I), effective in the prophylaxis or treatment of the conditions associated with HIV infection.

In a further aspect, the present invention concerns the use of a compound of formula (I) or any subgroup thereof in the manufacture of a medicament useful for preventing, treating or combating infection or disease associated with HIV infection.

In another aspect, the present invention concerns the use of a compound of formula (I) or any subgroup thereof in the manufacture of a medicament useful for inhibiting replication of a HIV virus, in particular a HIV virus having a mutant HIV reverse transcriptase, more in particular having a multi-drug resistant mutant HIV reverse transcriptase.

In yet another aspect, the present invention relates to the use of a compound of formula (I) or any subgroup thereof in the manufacture of a medicament useful for preventing, treating or combating a disease associated with HIV viral infection wherein the reverse transcriptase of the HIV virus is mutant, in particular a multi-drug resistant mutant HIV reverse transcriptase.

The compounds of formula (I) or any subgroup thereof are also useful in a method for preventing, treating or combating infection or disease associated with HIV infection in a mammal, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a mutant HIV virus, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a multi drug-resistant HIV virus, comprising administering to said mammal an effective amount of a compound of formula (I) or any subgroup thereof.

In yet another aspect, the compounds of formula (I) or any subgroup thereof are useful in a method for inhibiting replication of a HIV virus, in particular a HIV virus having a mutant HIV reverse transcriptase, more in particular a multi-drug resistant mutant HIV reverse transcriptase, comprising administering to a mammal in need thereof an effective amount of a compound of formula (I) or any subgroup thereof.

Preferably, a mammal as mentioned in the methods of this invention is a human being.

The compounds of the present invention may also find use in inhibiting ex vivo samples containing HIV or expected to be exposed to HIV. Hence, the present compounds may be used to inhibit HIV present in a body fluid sample that contains or is suspected to contain or be exposed to HIV.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

In the following reaction schemes each W independently represents a leaving group such as halo, e.g. chloro or bromo, tosylate, mesylate, and the like.

The compounds of formula (I) wherein X is a group NH, which compounds may be represented by formula (I-b), can be prepared by a cyclization procedure, as outlined in the following reaction scheme.

The synthesis of intermediates (I-b) starts from a 1-$C_{1-6}$alkylcarbonyl-3-hydroxy-indole (II-1), which is condensed with a substituted aniline yielding 3-(phenylamino)indoles (II-2). This condensation reaction may be conducted at elevated temperatures and in acidic circumstances e.g. by using an acidic solvent such as acetic acid, or using a solvent such as toluene, benzene, an alcohol and the like, with a suitable acid such as toluene sulfonic acid. Intermediate (II-2) subsequently is deacylated with a base, such as for example triethylamine, sodium or potassium hydroxide, sodium acetate, potassium acetate or potassium carbonate and the like, in a suitable solvent, such as for example methanol or ethanol, preferably at elevated temperature, yielding intermediates (II-3). Formylation of intermediates (II-3), for instance by applying a Vilsmeier reaction, results in indole aldehydes (II-4). Condensation of intermediates (II-4) with an acetic acid ester results in intermediate (II-5). In one embodiment, this condensation may be performed with an substituted acetic acid ester of formula $R^1$—$CH_2$—$COOR^{4a}$, wherein $R^{4a}$ is $C_{1-6}$alkyl or aryl$C_{1-6}$alkyl, using a base such as for example triethylamine, sodium acetate, potassium acetate, piperidine and the like, in a wide variety of solvents. Alternatively use may be made of a Wittig reaction or a Wittig-Horner reaction. In the former instance a Wittig type reagent, such as a triphenylphosphoniumylide is used. The Wittig conversion is conducted in a suitable reaction-inert solvent such as an ether, starting from triphenylphosphine and a halo acitic acid ester of formula $R^1$—CH(Halo)-$COOR^{4a}$. The Wittig-Horner reaction is performed using a phosphonate, such as e.g. a reagent of formula di($C_{1-6}$alkyloxy)-P(=O)—CH($R^1$)—$COOR^{4a}$ in the presence of a base, preferably a strong base, in an aprotic organic solvent.

Subsequent cyclisation of intermediates (II-5) at elevated temperature and in a solvent like ethyleneglycol, dioxane,

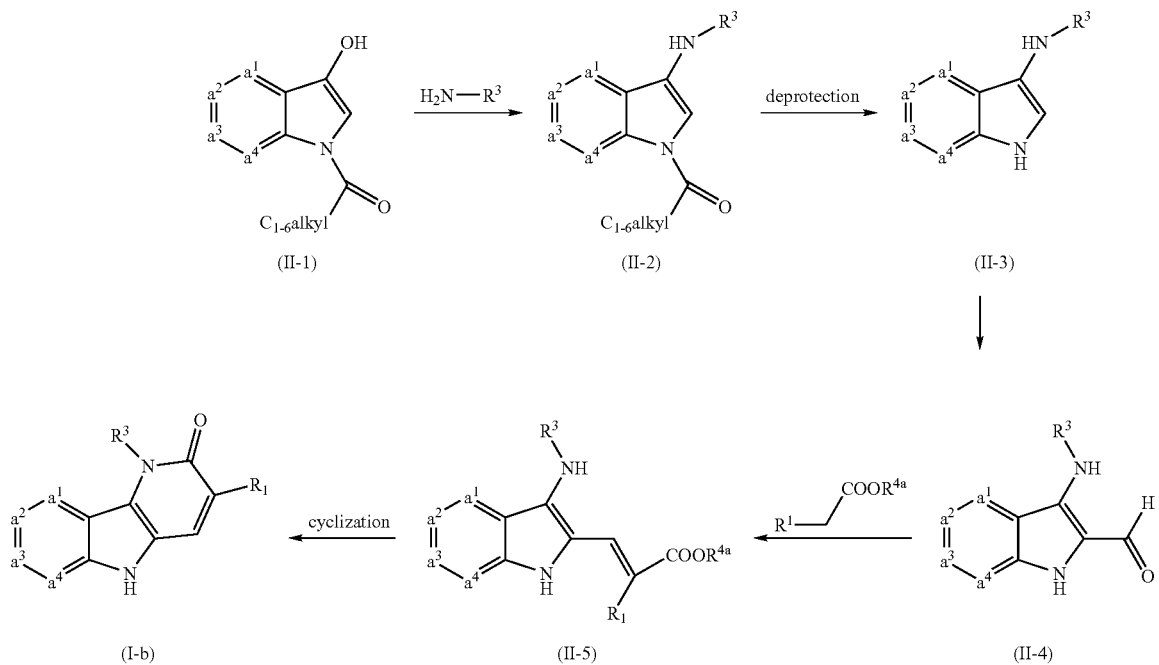

N,N-dimethylformamide, dimethylsulfoxide, glyme, diglyme and the like, yields compounds (I-b).

The order of the reaction steps in the process set out in the route 1 scheme may be different. For instance the formylation may be performed prior to deacylation.

The order of the reaction steps in the process set out in the above reaction scheme may be different. For instance the formylation may be performed prior to deacylation.

This synthesis pathway is particularly useful for preparing compounds of formula (I-b) wherein $R^3$ is nitro or cyano. In one embodiment, $R^3$ is para-nitro and the process starts from para-nitroaniline. It may also be used to prepare intermediates wherein $R^1$ is aminocarbonyl, $C_{1-4}$alkyloxycarbonyl, mono- or di($C_{1-4}$alkyl)aminocarbonyl, aryl-aminocarbonyl, N-(aryl)-N—($C_{1-4}$alkyl)aminocarbonyl, $Het_1$ or $Het_2$. The intermediates of formula (II) obtained through this reaction pathway may be converted to analogous intermediates of formula (II) wherein $R^1$ has the other meanings by functional group transformation reactions such as cyano to carboxyl hydrolysis, carboxyl to amide conversion, etc.

This synthesis pathway moreover is particularly useful to prepare intermediates of formula (II) wherein $R^3$ is nitro or cyano. In one embodiment, $R^3$ is para-nitro and the process starts from para-nitroaniline.

The compounds of formula (I-c), which are compounds of formula (I-b) wherein $R^1$ is cyano, may alternatively be prepared as outlined in the following reaction scheme.

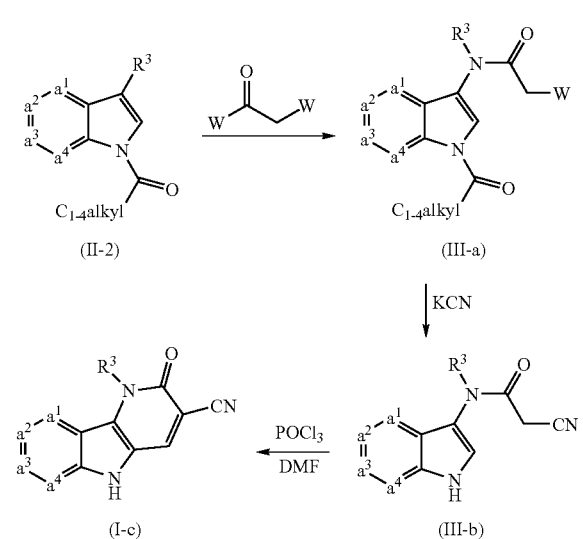

Intermediate (II-2), which is prepared as described in the previous reaction scheme, is reacted with chloroacetyl chloride or a functional derivative thereof, suitably at elevated temperature, to yield an intermediate of formula (III-a). The latter intermediate of formula (III-a) is deprotected using a suitable base such as triethylamine, sodium acetate, potassium acetate, sodium hydroxide, potassium hydroxide, potassium carbonate and the like, in a solvent like methanol or ethanol. The thus formed intermediate (III-b) is converted to the corresponding cyano derivative (III-b) using potassium cyanide or tetrabutylammoniumcyanide. The cyano derivative (III-b) is cyclized in a two step procedure comprising first a Vilsmeier formylation using $POCl_3$ in N,N-dimethylformamide and subsequent cyclization to form compound (I-c).

Compounds of formula (I-d), which are compounds of formula (I-b) wherein $R^1$ is hydrogen, can be prepared as outlined in the following reaction scheme.

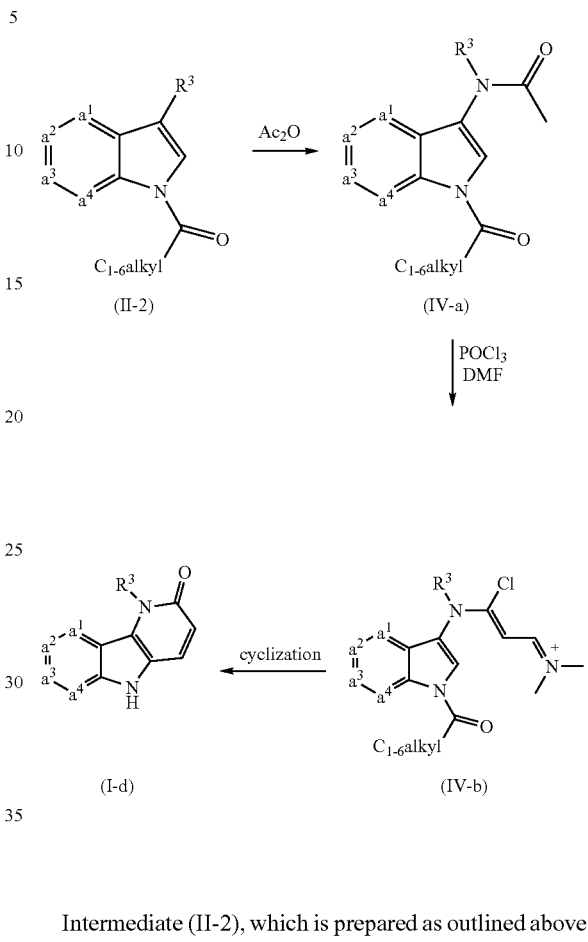

Intermediate (II-2), which is prepared as outlined above, is reacted with acetic anhydride in the presence of a catalyst such as for example pyridine or dimethylamino-pyridine or the like, suitably at elevated temperature, to yield an intermediate of formula (IV-a). The thus formed intermediate of formula (IV-a) is formylated using a Vilsmeier reaction with $POCl_3$ in N,N-dimethylformamide, to form intermediate (IV-b) which in turn can be further cyclized to a compound (II-b), e.g. in an aqueous acidic environment, e.g. in aqueous HCl.

Compounds of formula (I-b), (I-c) or (I-d) may be transformed into other compounds of formula (I) using art-known functional group transformation reactions. For example where $R^3$ is Br, Br may be transformed into a heterocyclic ring using heterocyclic borates and palladium. Or where $R^3$ is $C_{1-6}$alkyloxycarbonyl this radical may be transformed to the equivalent carboxylic acid or amide using a hydrolysis reaction, or respectively, an ester or carboxylic acid to amide reaction. Also $R^3$ being cyano may be transformed to a heterocycle such as a tetrazolyl, oxadiazolyl, thiazolyl etc. using art-known cyclization procedures.

The compounds of formula (I) wherein X is a group $NR^2$, which compounds may be represented by formula (I-e), can be prepared by N-alkylating intermediates of formula (I-b), (I-c) or (I-d) with a suitable N-alkylating agent, the reaction starting from (I-b) being outlined in the following reaction scheme.

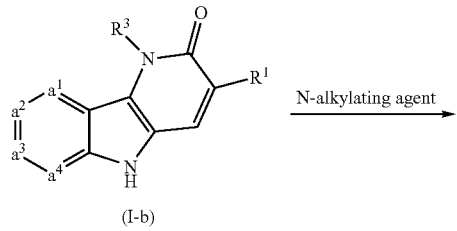

(I-b)

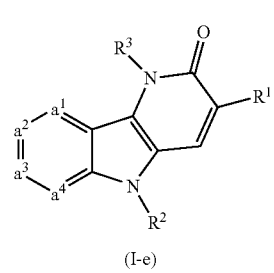

(I-e)

In one embodiment, the N-alkylating reagent is a reagent, which can be represented by formula $R^2$—W (V-a), wherein W is a leaving group. Suitable leaving groups are halo, in particular chloro, bromo and iodo, or other leaving groups such as for example sulfonates, e.g. tosylates, mesylates and the like. This type of N-alkylation reaction may be performed in an appropriate solvent in the presence of a suitable base such as a alkali metal hydride, e.g. sodium or potassium hydride, or an alkali or each alkaline metal hydroxide, carbonate or hydrogencarbonate, e.g. sodium or potassium carbonate, sodium or potassium hydroxide, calcium hydroxide, sodium or potassium hydrogencarbonate and the like.

Some of the compounds of formula (I-e) may also, where appropriate, be prepared by a reductive amination reaction which comprises reacting intermediates (II-a) with an intermediate $R^{2-a}$=O (V-b), wherein $R^{2-a}$ has the same meanings of $R^2$ provided that it has a carbon atom that can form an aldehyde of ketone functionality. This reaction may be conducted in the presence of hydrogen and a suitable catalyst, in particular a noble metal catalyst such as Pd or Pt, usually in a suitable solvent such as an ether or alcohol.

Some of the $R^2$ groups may also be introduced using $R^2$ groups derived from an epoxide. This type of reaction is particularly suited for introducing $R^2$ groups wherein $R^2$ is a radical (b-3), (b-4) or (b-5).

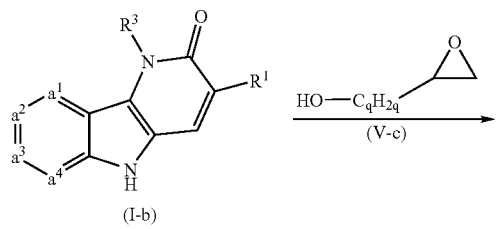

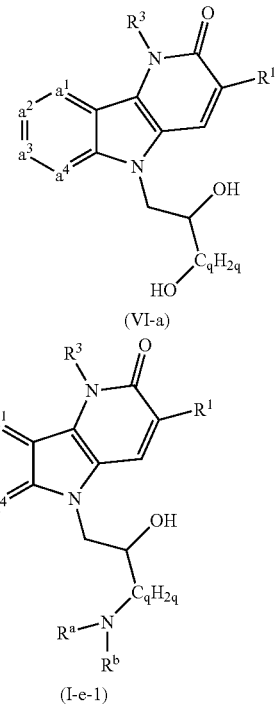

For example, compounds of formula (I-e), wherein $R^2$ is a radical (b-3) wherein p is 1 and wherein the group —$NR^aR^b$ are certain radicals amongst $R^{15}$ such as —$NR^{16a}R^{16b}$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, pyrrolyl, oxazolyl, thiazolyl, imidazolyl, isoxazolyl, isothiazolyl, pyrazolyl, oxadiazolyl, thiadiazolyl, triazolyl, tetrazolyl, a radical (a-1), (a-2), (a-3), or (a-5); wherein any of the foregoing heterocycles such as pyrrolidinyl, piperidinyl, homopiperidinyl, etc. is substituted on the $C_qH_{2q}$ moiety via a nitrogen atom; which compounds can be represented by formula (I-e-1); can be prepared by reacting a compound of formula (I-b) with an epoxide of formula (V-c). The resulting intermediates of formula (VI-a) can be converted into compounds of formula (I-e-1) wherein —$NR^aR^b$ is as specified above by an appropriate alcohol (C—OH) to amine (C—N) conversion reaction. The alcohol group may be converted into a suitable leaving group and subsequently reacted with an amine H—$NR^aR^b$. In an alternative execution, the alcohol group may be converted to an amine bond by a Mitsonobu-type reaction using an azodicarboxylate/triphenyl phosphine reagent, for example diisopropyl-azodicarboxylate (DIAD), and subsequent reaction with the appropriate amine. The thus obtained compounds of formula (I-e-1) can be O-alkylated or O-acylated in order to obtain the analogs of the compounds (I-e-1) wherein $R^{14}$ is other than hydrogen.

In a similar process, intermediates (I-b) are reacted with a epoxide (V-d) using a hydroxyl to amino conversion reaction such as the above described Mitsonobu reaction to obtain an epoxide (VI-b). The latter is reacted with an amine to yield compounds of formula (I-e-2) as outlined in the following reaction scheme. The compounds of formula (I-e-2) can also be O-alkylated or O-acylated as described in the previous paragraph.

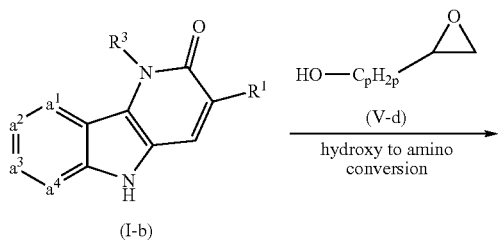

(I-b)

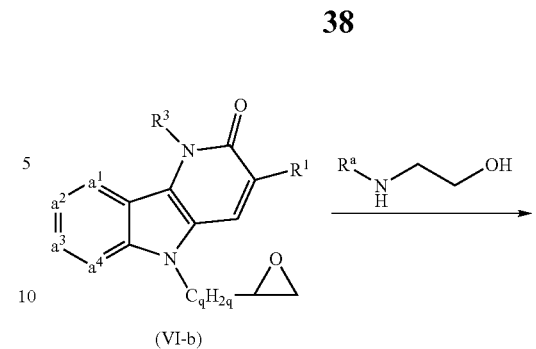

(VI-b)

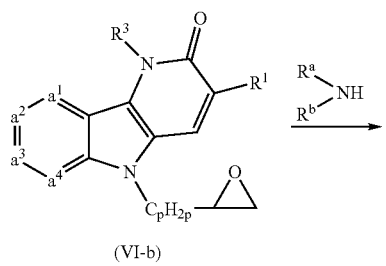

(VI-b)

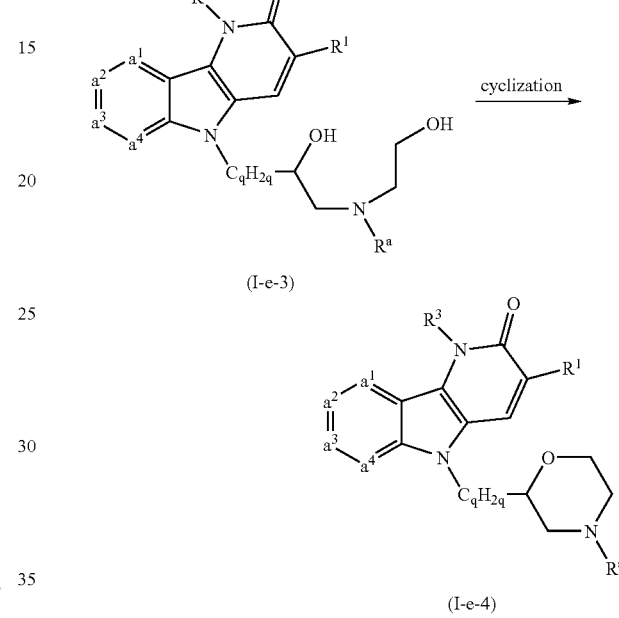

(I-e-3)

(I-e-4)

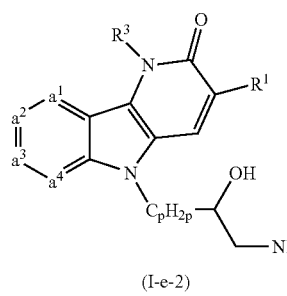

(I-e-2)

In an alternative procedure, compound (I-b) can be reacted with an epoxide having formula

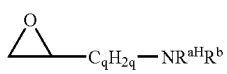
(V-e)

to directly obtain compounds of formula (I) wherein $R^2$ is a radical (b-3) wherein $R^{15}$ is an amino substituent —$NR^aR^b$.

The intermediates of formula (VI-b) can also be reacted with an alkanolamine to obtain compounds of formula (I-e-3), which are cyclized to obtain compounds (I-e-4), which are compounds of formula (I) wherein $R^2$ is alkyl substituted with a radical of formula (a-4). The cyclization may be conducted in the presence an acid such as hydrochloric acid with removal of water or in the presence of a suitable dehydrating agent for example sulfonyl amide such as an arylsulfonyl imidazole. These reactions are represented in the following reaction scheme wherein $R^a$ has the meanings of $R^{13a}$, provided that it is other than hydrogen. $R^a$ can also be a N-protecting group, which is removed afterwards, thus giving access to compounds wherein $R^{13a}$ is hydrogen.

Compounds wherein $R^2$ is a group (b-4) can be prepared starting from ethylene oxide followed by controlled addition of further ethylene oxide moieties. The resulting compounds may be alkylated to yield compounds of formula (I) having a (b-4) group with a $R^{14}$ radical that is other than hydrogen or converted into the corresponding amines (b-5) using a suitable alcohol to amine conversion reaction.

Compounds of formula (I) wherein is a phenyl group substituted with a —$COOR^4$ group can be obtained by suitable N-arylation reactions.

Compounds wherein $R^2$ is a group (b-1) can be prepared starting from a pyrrolidine, piperidine or homopiperidine derivative having a suitable leaving group. Similarly compounds wherein $R^2$ is a group (b-2) can be prepared starting from a morpholine having a suitable leaving group.

Compounds wherein $R^2$ is $C_{1-10}$alkyl, $C_{2-10}$alkenyl, $C_{3-7}$cycloalkyl, substituted with a radical selected from —$NR^{5a}$—$C(=NR^{5b})$—$NR^{5c}R^{5d}$, —O—$NR^{5a}$—$C(=NR^{5b})$—$NR^{5c}R^{5d}$, -sulfonyl-$R^6$, —$NR^7R^8$, —$NR^9R^{10}$, a radical (a-1), (a-2), or (a-3), as defined above, can be prepared starting from a $C_{1-10}$alkyl, $C_{2-10}$alkenyl, $C_{3-7}$cycloalkyl bearing two leaving groups which is reacted with a compound (I-b) in a controlled manner such that only one of the leaving groups is substituted. Subsequently the thus obtained intermediate is reacted with an appropriate amine or amineoxide thus substituting the second leaving group. For example compound of formula (I-b) may be reacted with a $C_{1-10}$alkylene dihalide and subsequently reacted with an amine H—$NR^7R^8$, H—$NR^9R^{10}$ or another amine. Other similar process variants may be used in which some or several functionalities are protected and subsequently deprotected.

The compounds of formula (I) wherein X is O, wherein $R^2$ is cyano, which compounds are represented by formula (I-f), can be prepared as outlined in the following reaction scheme.

The compounds of formula (I) wherein $-a^1=a^2-a^3=a^4-$ is a radical (c-1), which is substituted with amino groups, said compounds being represented by formula (I-h), can be prepared as outlined in the following reaction scheme.

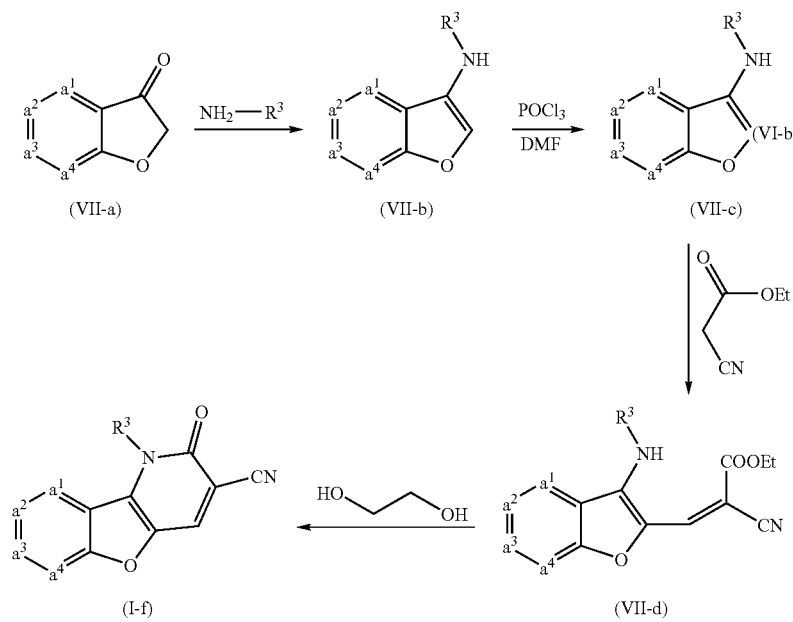

3-Hydroxybenzofuran (VII-a) is condensed with a suitable amine derivative to result in a 3-phenylaminobenzofuran (VII-b) [see V. A. Azimov, S. Yu. Ryabova, L. M. Alekseeva and V. G. Granik, *Chemistry of heterocyclic compounds* 2000, 36, 1272-1275]. The conversion from (VII-a) to (VII-b) may be conducted in a suitable solvent such as a hydrocarbon, for example toluene, typically in the presence of a catalytic amount of acid such as e.g. p-toluenesulfonic acid. The 3-phenylaminobenzofuran (VII-b) is formylated, for example by using phosphorus oxychloride in DMF followed by hydrolysis. The formylated derivative (VII-c) may be converted to a compound (VII-d) by using a cyano acetate derivative, typically in a suitable solvent such as an alcohol, e.g. iso-propanol, in the presence of a base, preferably a tertiary amine base such as triethylamine. Intermediate (VII-d) subsequently is cyclized at elevated temperature to yield compound (I-f). A suitable solvent for this cyclization reaction is a glycol such as, e.g., ethylene glycol.

This synthesis route may also be used to prepare analogs of the compounds (I-e) wherein $R^1$ is other than cyano, in particular compounds of formula (I-e) wherein $R^1$ is $C_{1-4}$alkyloxycarbonyl, by reacting (VI-c) with a di($C_{1-4}$alkyl)malonic acid ester.

The compounds of formula (I) wherein X is S can be prepared from the sulfur analogs of intermediate (VII-a), i.e. 3-hydroxybenzothiene, following the same procedures outlined above yielding the sulfur analogs of compounds (I-f). The latter can be converted to the corresponding sulfoxides (X is SO) or sulfones (X is $SO_2$) using art known oxidation procedures, e.g. by treatment with a suitable peroxide.

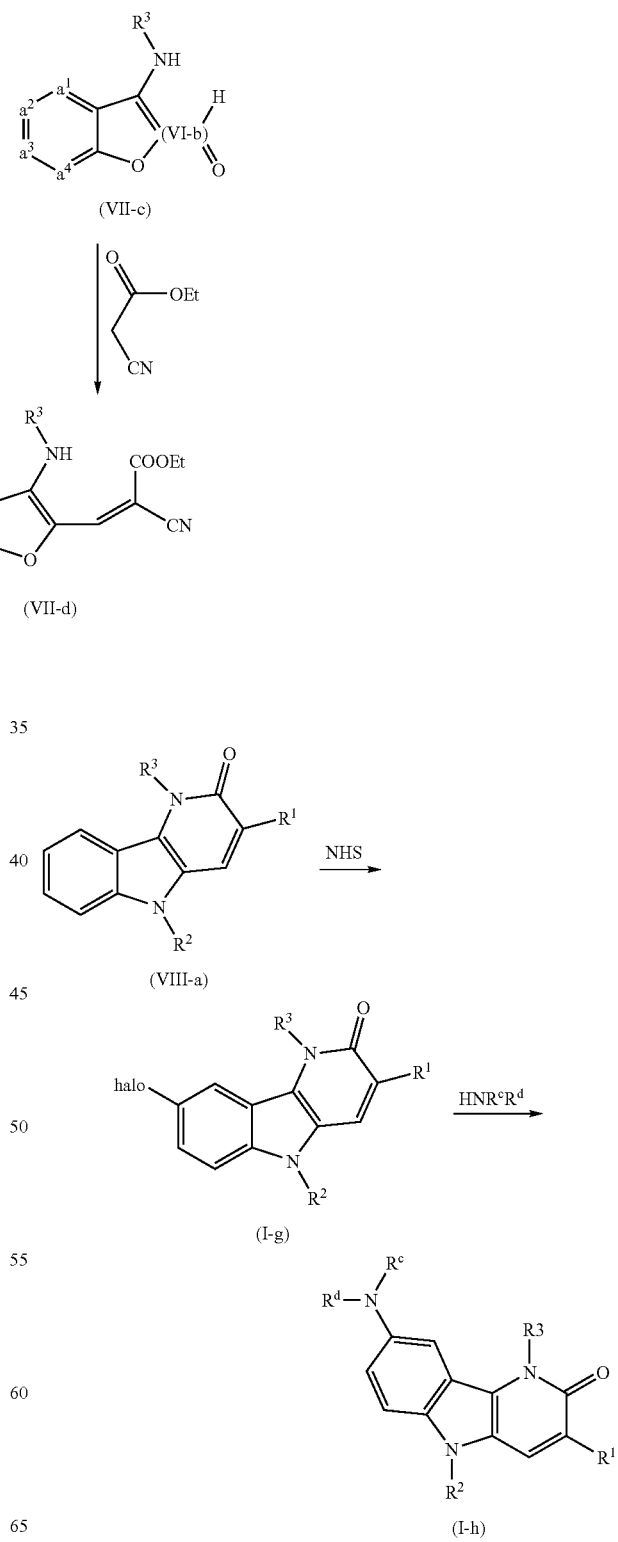

Starting intermediate (VIII-a) can be prepared following procedures described above for the preparation of compounds (I-b), starting from intermediates wherein -$a^1$=$a^2$-$a^3$=$a^4$- (c-1) is an unsubstituted CH=CH—CH=CH radical, followed by an N-alkylation reaction to introduce substituent $R^2$. Intermediates (VIII-a) are halogenated using a suitable halogenating agent such as N-halosuccinimide (NHS), e.g. N-bromosuccininide, to a compound (I-g).

The resulting compound (I-g) may be converted to analogs wherein radical (c-1) is substituted with a group —$NR^cR^d$, wherein —$NR^cR^d$ is an amino substituent on radical -$a^1$=$a^2$-$a^3$=$a^4$- (c-1), by a suitable substitution reaction replacing the halogen atom by the desired amino group. In preferred execution use can be made of suitable catalyst such as a bis(diphenylphosphino) palladium complex e.g. 2,2'-bis(diphenylphosphino)-1,1'-binaphtyl palladium complex. This reaction is typically conducted in a suitable solvent such as 1,4-dioxane in the presence of a base such as potassium t.butoxide or cesium carbonate. An unsubstituted amino group (—$NH_2$) can be obtained using benzophenon imine and subsequent removal of the benzophenon group.

The compounds of formula (I) wherein -$a^1$=$a^2$-$a^3$=$a^4$- is a radical (c-1), which is substituted with alkoxycarbonyl groups, said compounds being represented by formulae (I-i), can be prepared by reacting compounds of formula (I-g) with CO gas in the presence of a suitable catalyst e.g. [1,1'-bis (diphenylphosphino)ferrocene]dichloropalladium(II) in a suitable solvent, e.g. dimethylformamide, in the presence of $C_{1-4}$alkyl alcohol, e.g. methanol or ethanol. This reaction may be conducted under pressure e.g. in a Parr reactor at higher temperature.

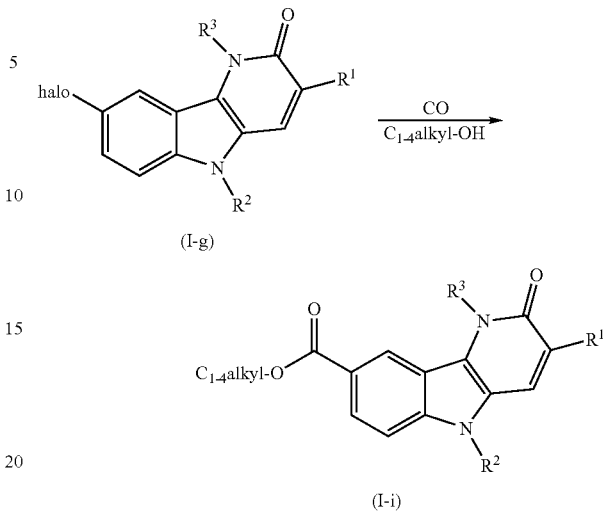

When using this reaction procedure with compounds wherein $R^3$ is a nitrophenyl group, the nitro group is reduced during the CO addition reaction to the corresponding amino group. The latter can be converted into a nitro group by using a suitable oxidant such as a perborate, e.g. sodium perborate monohydrate.

The compounds of formula (I) can also be used by introducing a heterocycle on a starting material which is a compound of formula (I) wherein $R^3$ is hydrogen. Said starting material can be prepared as outlined in the two following reaction schemes.

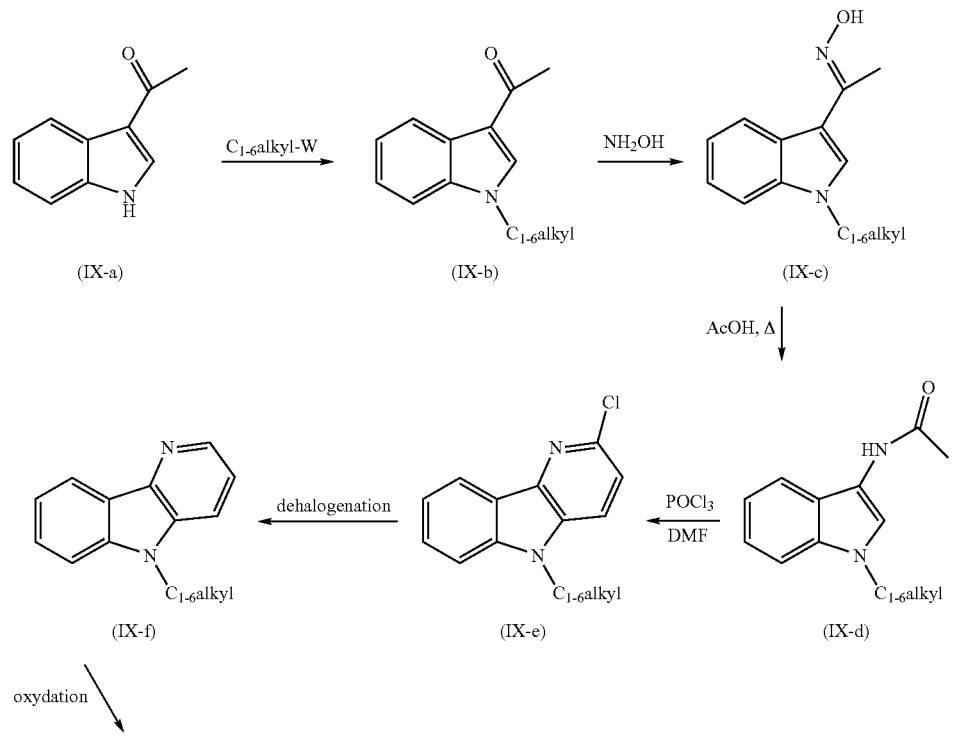

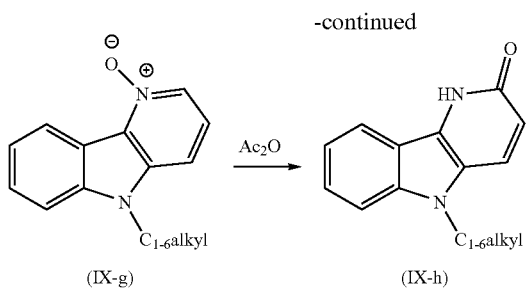

The above synthesis procedure allows the preparation of intermediates wherein $R^1$ and $R^3$ are hydrogen. This reaction procedure can also be applied to analogs of these compounds having an $a^1=a^2-a^3=a^4$- group other than CH=CH—CH=CH. Intermediate (IX-a) is reacted with a reagent $C_{1-6}$alkyl-W, wherein W is a leaving group, e.g. a $C_{1-6}$alkyliodide or $C_{1-6}$alkylsulfate, in the presence of a base such as for example potassium carbonate, potassium hydroxide, sodium hydroxide and the like, preferably in a reaction-inert solvent such as for example N,N-dimethylformamide, acetonitrile, acetone, ethanol, and the like. By using alkylating agents other than a $C_{1-6}$alkyliodide, analogous intermediates with various $R^2$ groups can be obtained. The thus formed intermediate of formula (IX-b) is then reacted with hydroxylamine in a solvent like water, ethanol or a mixture thereof and in the presence of a base like sodium or potassium acetate, potassium carbonate, and the like, to form an intermediate of formula (IX-c). Upon heating and bringing the intermediate of formula (IX-c) in an acidic aqueous environment e.g. in acetic acid, an intermediate of formula (IX-d) is formed. The latter intermediate is subjected to an intramolecular cyclisation in the presence of $POCl_3$ in N,N-dimethylformamide. The thus formed intermediate of formula (IX-e) is dehalogenated e.g. by treatment with zinc in an acidic aqueous environment such as HCl, to form an intermediate of formula (IX-f). The N-oxide can be prepared using metachloroperbenzoic acid, hydrogen peroxide, tert-butyl hydroperoxide and the like, or a functional equivalent thereof in a solvent such as, for example, dichloromethane, chloroform, an alcohol, toluene or the like, at elevated temperatures. The N-oxide of formula (IX-g) can be further reacted, suitably at elevated temperature, with acetic anhydride to form the intermediate of formula (IX-h).

The following synthesis procedure can be used to prepare intermediates wherein $R^3$ is hydrogen and $R^1$ is cyano.

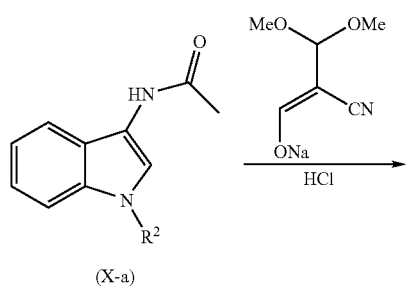

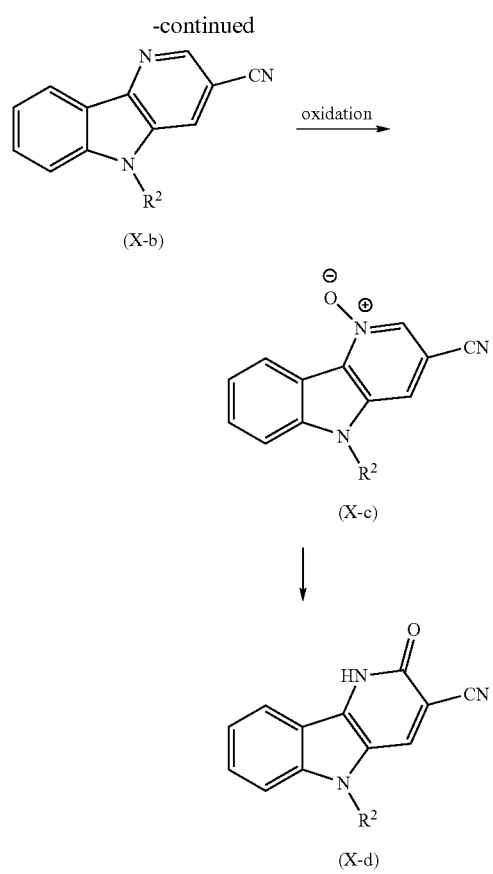

Intermediate (X-a), which can be an intermediate (IX-d) as outlined in the previous reaction scheme, or an analog thereof wherein $R^2$ is other than a $C_{1-6}$alkyl, and 3,3-dimethoxy-2-formyl-propionitrile sodium salt [see e.g. R. B. G. Dupas, J. Bourguignon, G. Quéguiner Synthesis 1987, 1124] are mixed in a suitable solvent, e.g. in methanol, to which a strong acid, e.g. concentrated hydrochloric acid is added. The latter mixture is heated at reflux and upon cooling an acid salt of compound (X-b) is formed which subsequently is neutralized to the free base. Intermediate (X-b) is oxidized e.g. with a peroxy acid such m-chloroperbenzoic acid to product (X-c). The latter is reacted with acetic anhydride. The resulting product is treated with a strong base, e.g. sodium hydroxide, and subsequently acidified with strong acid, e.g. hydrochloric acid. The resulting product is refluxed in methanol yielding intermediate (X-d).

The intermediates (IX-g) or (X-d) as obtained in the previously described synthesis, or analogs, can be converted to end products (I-k) as outlined in the following reaction scheme.

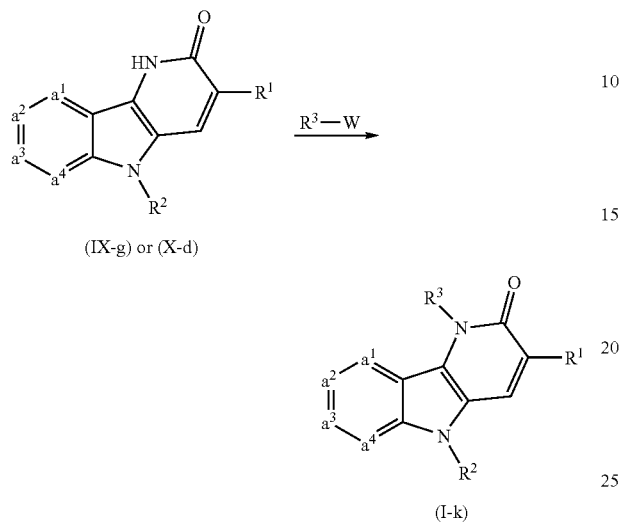

(IX-g) or (X-d)

(I-k)

Intermediates of formula (IX-g) or (X-d) or analogs thereof are converted into end products of formula (I-k) by a suitable N-arylation reaction using a heterocyclic reagent of formula $R^3$—W, wherein W is an appropriate leaving group, in particular W is halo such as chloro and bromo. In the latter case, a catalyst such as copper(I)iodide may be added. Usually the reaction is conducted in a suitable solvent, e.g. DMF, DMA, dichloromethane, in the presence of a base. In particular instances heterocycles with special groups such as boronic acid (i.e. —B(OH)$_2$) or borate esters (i.e. —B(OR)$_2$ wherein R is alkyl or alkylene, e.g. R is methyl, ethyl or ethylene) can be used, the reaction being typically conducted in the presence of a copper salt, in particular copper(II) acetate, and a suitable quencher like pyridine may be added to the reaction mixture.

Compounds of formula (I) wherein $R^3$ is halo substituted heterocycle, i.e. compounds (I-1) can be converted to the corresponding alkylthio compounds (I-m) by treatment with a $C_{1-6}$alkylthiol R—SH, which in turn can be oxidized, e.g. with a peroxide such as 3-chloroperoxybenzoic acid, to the corresponding sulfones of formula (I-n).

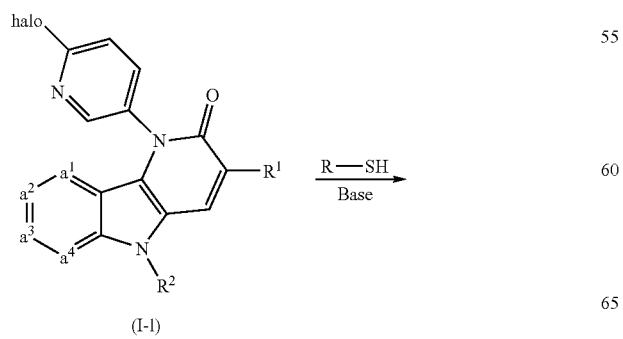

(I-l)

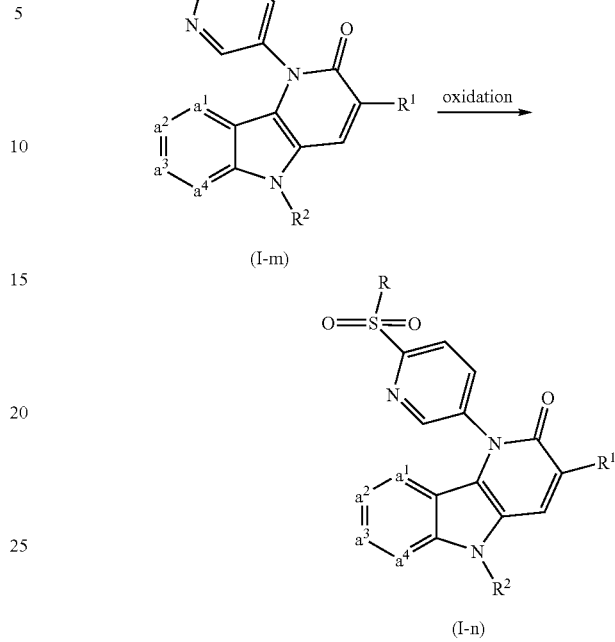

(I-m)

(I-n)

The compounds (I-l) can also be converted to the corresponding cyano compounds (I-o) by reacting the starting materials with a suitable cyano nucleophile, e.g. copper(I) cyanide, preferably in a suitable solvent.

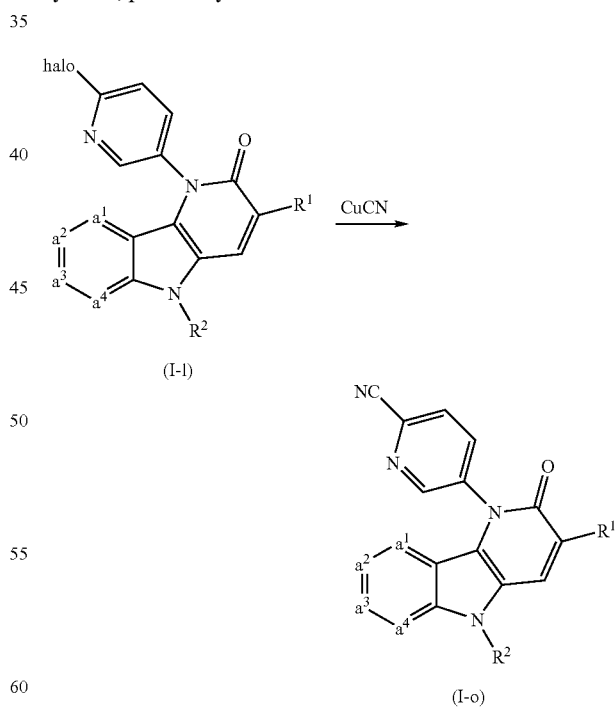

(I-l)

(I-o)

The compounds of formula (I) may be transferred into other compounds of formula (I) with different substitution using art-known transformation techniques. For instance, the compounds of formula (I) wherein $R^3$ having a nitro group may be reduced to the corresponding amino analogs, and may then be further derivatized. Further examples of transformation reactions are given in the experimental part.

The compounds of formula (I) wherein $R^1$ is cyano may be hydrolysed to the corresponding compounds of formula (I) wherein $R^1$ is hydroxycarbonyl, which in turn may be esterified to obtain compounds of formula (I) wherein $R^1$ is $C_{1-4}$alkyloxycarbonyl. The latter or the hydroxycarbonyl derivatives may be converted to the corresponding amides using art-known carboxyl to amide or alkylester to amide transformation reactions.

Compounds of formula (I) having a —COOR$^4$ group wherein $R^4$ is hydrogen may be converted to the corresponding esters using art-known esterification procedures. Vice versa, the esters can be converted to the free acid by suitable hydrolysis procedures, e.g. by hydrolysis in acidic or basic media.

Compounds of formula (I) having a thiomorpholinyl group can be oxidized to the corresponding 1-oxothiomorpholinyl or 1,1-dioxothiomorpholinyl containing compounds using a suitable organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. The 1-oxothiomorpholinyl analogs are preferably obtained using controlled oxidation procedures.

The compounds of formula (I) may also be converted to the corresponding N-oxide forms following art-known procedures for converting a tri-substituted nitrogen into its N-oxide form. Said N-oxidation reaction may generally be carried out by reacting the starting material of formula (I) with a suitable organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A basic nitrogen occurring in the present compounds can be quaternized with any agent known to those of ordinary skill in the art including, for instance, lower alkyl halides, dialkyl sulfates, long chain halides and aralkyl halides according to art-known procedures.

The compounds of the present invention may be used in animals, preferably in mammals, and in particular in humans as pharmaceuticals per se, in mixtures with one another or in the form of pharmaceutical preparations.

Consequently, the present invention relates to pharmaceutical formulations containing as active ingredients an effective dose of at least one of the compounds of formula (I) in addition to customary pharmaceutically innocuous excipients and auxiliaries. The pharmaceutical preparations may contain 0.1 to 90% by weight of a compound of formula (I). The pharmaceutical preparations can be prepared in a manner known per se to one of skill in the art. For this purpose, a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical product in human medicine or veterinary medicine.

Pharmaceuticals which contain a compound according to the invention can be administered orally, parenterally, e.g., intravenously, rectally, by inhalation, or topically, the preferred route of administration being dependent on the individual case, e.g., the particular course of the disorder to be treated. Oral administration is preferred.

The person skilled in the art is familiar on the basis of his expert knowledge with the auxiliaries that are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Also, the combination of an antiretroviral compound and a compound of the present invention can be used. Thus, to prevent, combat or treat HIV infections and the diseases associated with HIV infection, such as Acquired Immunodeficiency Syndrome (AIDS) or AIDS Related Complex (ARC), the compounds of this invention may be co-administered in combination with for instance, binding inhibitors, fusion inhibitors, co-receptor binding inhibitors; RT inhibitors; nucleoside RTIs; nucleotide RTIs; NNRTIs; RNAse H inhibitors; TAT inhibitors; integrase inhibitors; protease inhibitors; glycosylation inhibitors; entry inhibitors.

Any of these combinations may provide a synergistic effect, whereby viral infectivity and its associated symptoms may be prevented, substantially reduced, or eliminated completely.

Thus in a further aspect, the present invention also relates to combinations containing:
(a) a compound of the present invention, in particular a compound of formula (I) as defined herein, or a compound of formula (I) of any of the subgroups specified herein; an N-oxide, salt, stereoisomeric form, prodrug, ester or metabolite thereof, and
(b) another anti-retroviral compound, in particular another HIV inhibitor.

The present invention additionally relates to combinations containing
(a) (a) a compound of the present invention, in particular a compound of formula (I) as defined herein, or a compound of formula (I) of any of the subgroups specified herein, an N-oxide, salt, stereoisomeric form, prodrug, ester or metabolite thereof, and
(b) any of the agents selected from binding inhibitors, such as, for example, dextran sulfate, suramine, polyanions, soluble CD4, PRO-542, BMS-806; fusion inhibitors, such as, for example, T20, T1249, RPR 103611, YK-FH312, IC 9564, 5-helix, D-peptide ADS-J1; co-receptor binding inhibitors, such as, for example, AMD 3100, AMD-3465, AMD7049, AMD3451 (Bicyclams), TAK 779, T-22, ALX40-4C; SHC-C (SCH351125), SHC-D, PRO-140, RPR103611; RT inhibitors, such as, for example, foscarnet and prodrugs; nucleoside RTIs, such as, for example, AZT, 3TC, DDC, DDI, D4T, Abacavir, FTC, DAPD (Amdoxovir), dOTC (BCH-10652), fozivudine, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, QM96521, GW420867X, DPC 961, DPC963, DPC082, DPC083, calanolide A, SJ-3366, TSAO, 4"-deaminated TSAO, MV150, MV026048, PNU-142721; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and fosamprenavir, ritonavir, nelfinavir, saquinavir, indinavir, lopinavir, palinavir, BMS 186316, atazanavir, DPC 681, DPC 684, tipranavir, AG1776, mozenavir, DMP-323, GS3333, KNI-413, KNI-272, L754394, L756425, LG-71350, PD161374, PD173606, PD177298, PD178390, PD178392, PNU 140135, TMC-114, maslinic acid, U-140690; glycosylation inhibitors, such as, for example, castanospermine, deoxynojirimycine; entry inhibitors CGP64222; hereafter referred to as agents belonging to group (b).

In one embodiment there are provided combinations containing ingredients (a) and (b), as specified above, wherein the compound of the present invention is a compound (I-a), an N-oxide, salt, stereoisomeric form, prodrug, ester or metabolite thereof.

In another embodiment there are provided combinations containing ingredients (a) and (b), as specified above, wherein the compound of the present invention is selected from the group consisting of:

8-Methoxy-5-methyl-1-(6-methyl-pyridin-3-yl)-2-oxo-2,5-dihydro-1H-pyrido-[3,2-b]indole-3-carbonitrile, 1-(2,8-Dimethyl-imidazo[1,2-a]pyridin-6-yl)-5-methyl-2-oxo-2,5-dihydro-1H-pyrido-[3,2-b]indole-3-carbonitrile, 1-(6-Chloro-5-methyl-pyridin-3-yl)-5-methyl-2-oxo-2,5-dihydro-1H-pyrido[3,2-b]-indole-3-carbonitrile, 1-(6-Chloro-pyridin-3-yl)-8-hydroxy-5-methyl-2-oxo-2,5-dihydro-1H-pyrido[3,2-b]-indole-3-carbonitrile, 1-(6-Chloropyridin-3-yl)-5-methyl-2-oxo-2,5-dihydro-1H-pyrido[3,2-b]indole-3-carbonitrile, 5-Methyl-1-(2-methyl-imidazo[1,2-a]pyridin-6-yl)-2-oxo-2,5-dihydro-1H-pyrido-[3,2-b]indole-3-carbonitrile, 5-Methyl-1-(6-methyl-pyridin-3-yl)-2-oxo-2,5-dihydro-1H-pyrido[3,2-b]indole-3-carbonitrile, and their N-oxides, salts and possible stereoisomers, said group hereafter being referred to as "group of compounds (I-p)".

Embodiments of this invention are combinations comprising (a) one or more compounds of formula (I), or compounds of any of the subgroups of compounds of formula (I), as specified herein, in particular of the subgroups of compounds of formula (I-a), or the group of compounds (I-p), including the N-oxides, salts, stereoisomeric forms, prodrugs, esters and metabolites thereof; and (b) one or more HIV inhibitors selected from:

(i) one or more fusion inhibitors, such as, for example, T20, T1249, RPR 103611, YK-FH312, IC 9564, 5-helix, D-peptide ADS-J1, enfuvirtide (ENF), GSK-873,140, PRO-542, SCH-417,690. TNX-355, maraviroc (UK-427,857); preferably one or more fusion inhibitors, such as, for example, enfavirtide (ENF), GSK-873,140, PRO-542, SCH-417, 690. TNX-355, maraviroc (UK-427,857);

(ii) one or more nucleoside RTIs, such as for example AZT, 3TC, zalcitabine (ddC), ddI, d4T, Abacavir (ABC), FTC, DAPD (Amdoxovir), dOTC (BCH-10652), fozivudine, D-D4FC (DPC 817 or Reverset™), alovudine (MIV-310 or FLT), elvucitabine (ACH-126,443); preferably one or more nucleoside RTIs, such as for example, AZT, 3TC, zalcitabine (ddC), ddI, d4T, Abacavir (ABC), FTC, DAPD (Amdoxovir), D-D4FC (DPC 817 or Reverset™), alovudine (MIV-310 or FLT), elvucitabine (ACH-126,443);

(iii) nucleotide RTIs, such as, for example, PMEA, PMPA (TDF or tenofovir) or tenofovir disoproxil fumarate; preferably tenofovir or tenofovir disoproxil fumarate;

(iv) one or more NNRTIs such as, for example, nevirapine, delavirdine, efavirenz, 8 and 9-Cl TIBO (tivirapine), loviride, TMC125, 4-[[4-[[4-(2-cyanoethenyl)-2,6-diphenyl]amino]-2-pyrimidinyl]amino]-benzonitrile (TMC278 or R278474), dapivirine (R147681 or TMC120), MKC-442, UC 781, UC 782, Capravirine, QM96521, GW420867X, DPC 961, DPC963, DPC082, DPC083 (or BMS-561390), calanolide A, SJ-3366, TSAO, 4"-deaminated TSAO, MV150, MV026048, PNU-14272; or preferably one or more NNRTIs such as for example nevirapine, delavirdine, efavirenz, TMC125, TMC278, TMC120, capravirine, DPCO83, calanolide A;

(v) one or more protease inhibitors, such as, for example, amprenavir and fosamprenavir, lopinavir, ritonavir (as well as combinations of ritonavir and lopinavir such as Kaletra™), nelfinavir, saquinavir, indinavir, palinavir, BMS 186316, atazanavir, DPC 681, DPC 684, tipranavir, AG1776, mozenavir, DMP-323, GS3333, KNI-413, KNI-272, L754394, L756425, LG-71350, PD161374, PD173606, PD177298, PD178390, PD178392, PNU 140135, TMC-114, maslinic acid, U-140690; in particular one or more protease inhibitors, such as, for example, amprenavir and fosamprenavir, lopinavir, ritonavir (as well as combinations of ritonavir and lopinavir), nelfinavir, saquinavir, indinavir, atazanavir, tipranavir, TMC-114.

In a further aspect the present invention provides combinations comprising at least one compound of formula (I) or compounds of any of the subgroups of compounds of formula (I), as specified herein, in particular of the subgroups of compounds of formula (I-a), or the group of compounds (I-P), including the N-oxides, salts, stereoisomeric forms, prodrugs, esters and metabolites thereof, and at least two different other antiretroviral agents.

One embodiment are combinations as specified in the previous paragraph wherein said two different other antiretroviral agents are (i) two nucleoside transcriptase inhibitors (NRTIs);

(ii) a nucleoside (NRTIs) and a nucleotide reverse transcriptase inhibitor (NtRTI);

(iii) an NRTI and an NNRTI;

(iv) an NRTI and a protease inhibitor (PI);

(v) two NRTIs and a PI;

(vi) an NRTI and a fusion inhibitor.

The NRTIs, NtRTs, NNRTIs, PIs and fusion inhibitors in the combinations mentioned in the previous paragraph may be selected from the groups of NRTIs, NtRTIs, NNRTIs, PIs and fusion inhibitors (i), (ii), (iii), (iv) or (v) mentioned above in relation to embodiments which are combinations comprising ingredients (a) and (b).

Of particular interest among the combinations mentioned above are those comprising a compound of the present invention having the formula (I) or (I-a), or belonging to or the group of compounds (I-P), as specified above, and:

(1) a fusion inhibitor selected from enfuvirtide (ENF), GSK-873,140, PRO-542, SCH-417,690. TNX-355, maraviroc (LJK-427,857);

(2) an NNRTI selected from nevirapine, delavirdine, efavirenz, TMC125, TMC278, TMC120, capravirine, DPC083, calanolide A;

(3) an NRTI selected from AZT, 3TC, zalcitabine (ddC), ddI, d4T, Abacavir (ABC), FTC, DAPD (Amdoxovir), D-D4FC (DPC 817 or Reverset™), alovudine (MIV-310 or FLT), elvucitabine (ACH-126,443).

(4) an NtRTI selected from tenofovir or tenofovir disoproxil fumarate;
(5) a PI selected from amprenavir and fosamprenavir, lopinavir, ritonavir (as well as combinations of ritonavir and lopinavir), nelfinavir, saquinavir, indinavir, atazanavir, tipranavir, TMC-114;
(6) a NRTI as in (3) and a PI as in (5);
(7) two different NRTIs as in (3);
(8) an NRTI as in (3) and an NNRTI as in (2);
(9) two different NRTIs as in (3) and an NNRTI as in (2);
(10) two different NRTIs as in (3) and a PI as in (5);
(11) a NRTI as in (3) and an NtRTI as in (4); or
(12) a NRTI and a fusion inhibitor as in (1).

One type of embodiments of this invention are those combinations as outlined herein that do not contain 3TC.

The present invention also relates to a product containing (a) a compound of the present invention, in particular a compound of formula (I) as defined herein, or a compound of formula (I) of any of the subgroups defined herein, its N-oxides, salts, stereoisomeric forms, prodrugs, esters and metabolites, or any compound of a subgroup as specified herein, and (b) another antiretroviral compound, as a combined preparation for simultaneous, separate or sequential use in treatment of retroviral infections such as HIV infection, in particular, in the treatment of infections with multi-drug resistant retroviruses.

Any of the above combinations may provide a synergistic effect, whereby viral infectivity and its associated symptoms may be prevented, substantially reduced, or eliminated completely.

Any of the above mentioned combinations or products may be used to prevent, combat or treat HIV infections and the disease associated with HIV infections, such as Acquired Immunodeficiency Syndrome (AIDS) or AIDS Related Complex (ARC). Therefore in a further aspect there are provided methods of treating mammals, in particular humans, being infected with HIV or at risk of being infected with HIV, said method comprising administering to said mammals, or in particular to said humans, a combination or a product as specified herein.

The compounds of the present invention may also be administered in combination with immunomodulators (e.g., bropirimine, anti-human alpha interferon antibody, IL-2, methionine enkephalin, interferon alpha, and naltrexone) with antibiotics (e.g., pentamidine isothiorate) cytokines (e.g. Th2), modulators of cytokines, chemokines or modulators of chemokines, chemokine receptors (e.g. CCR5, CXCR4), modulators chemokine receptors, or hormones (e.g. growth hormone) to ameliorate, combat, or eliminate HIV infection and its symptoms. Such combination therapy in different formulations, may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations, may be administered simultaneously, sequentially or independently of each other. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefore such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxy-propyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavours.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions, which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those that physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable, and have appropriate dimensions and firmness. Examples of such materials are polymers, inorganic substances, organic substances, and saccharides and derivatives thereof.

The route of administration may depend on the condition of the subject, co-medication and the like.

Another aspect of the present invention concerns a kit or container comprising a compound of formula (I) in an amount effective for use as a standard or reagent in a test or assay for determining the ability of a potential pharmaceutical to inhibit HIV reverse transcriptase, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram®. The Antivirogram® is a highly automated, high throughput, second generation, recombinant assay that can measure susceptibility, especially viral susceptibility, to the compounds of the present invention. (Hertogs K et al. *Antimicrob Agents Chemother,* 1998; 42(2):269-276, incorporated by reference).

The compounds of the present invention may comprise chemically reactive moieties capable of forming covalent bonds to localized sites such that said compound have increased tissue retention and half-lives. The term "chemically reactive group" as used herein refers to chemical groups capable of forming a covalent bond. Reactive groups will generally be stable in an aqueous environment and will usually be carboxy, phosphoryl, or convenient acyl group, either as an ester or a mixed anhydride, or an imidate, or a maleimidate thereby capable of forming a covalent bond with functionalities such as an amino group, a hydroxy or a thiol at the target site on for example blood components such as albumine. The compounds of the present invention may be linked to maleimide or derivatives thereof to form conjugates.

In still a further aspect, the present invention provides a method of treating patients who are infected by the HIV virus or at risk of becoming infected by the HIV virus, said method comprising the administration of an effective amount of a combination of a compound of formula (I) or a compound of a subgroup of compounds of formula (I), as specified herein, and another HIV-inhibitor, which can be any of the HIV-inhibitors mentioned herein.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight co-medication and individual responsiveness of the human or animal to be treated and on whether the therapy is acute or prophylactic. Customarily, the daily dose of a compound of formula (I) in the case of administration to a patient approximately 75 kg in weight is 1 mg to 3 g, preferably 3 mg to 1 g, more preferably, 5 mg to 0.5 g. The dose can be administered in the form of an individual dose, or divided into several, e.g. two, three, or four, individual doses.

EXAMPLES

The following examples illustrate the preparation of the compounds of formula (I) and their intermediates as well as their pharmacological properties. These should not be construed as a limitation of the scope of the present invention.

Example 1

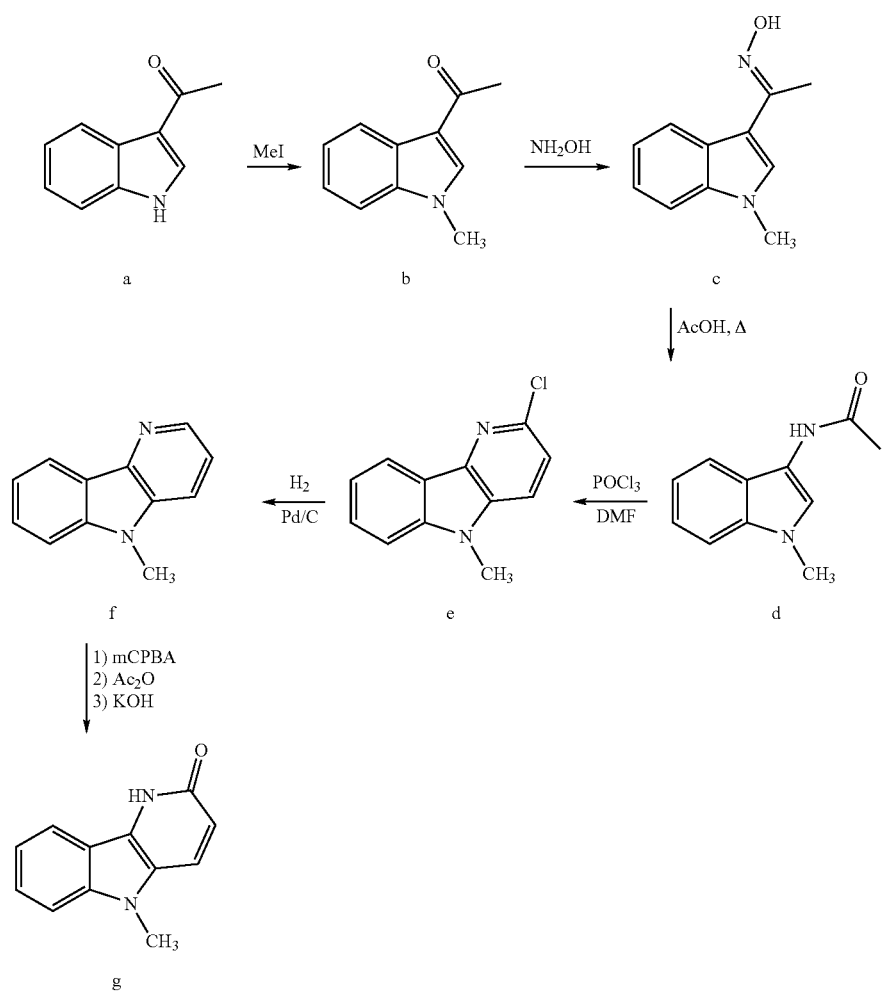

To a mixture of 3-acetylindole a (0.157 mol, 25.0 g) in DMF (200 ml) was added potassium carbonate (1.05 equiv., 0.165 mol, 22.8 g) and methyl iodide (1.1 equiv., 0.173 mol, 24.5 g). The mixture was stirred at room temperature overnight. A second portion of both potassium carbonate (2.1 equiv., 0.330 mol, 45.6 g) and methyl iodide (2.2 equiv., 0.346 mol, 49.0 g) were added and the mixture was stirred at room temperature for an additional 3 hours. The mixture was concentrated under reduced pressure to $\frac{1}{5}^{th}$ of the original volume. The residue was dissolved in dichloromethane and washed with water. The organic phase was dried with MgSO$_4$ and concentrated in vacuo, affording intermediate b (24.8 g, yield=92%, purity (LC)=90%). The crude product was used without further purification in the next step.

To a mixture of intermediate b (0.312 mol, 54.0g) in ethanol (150 ml) and water (100 ml) was added acetic acid, sodium salt (2.4 equiv., 0.748 mol, 61.0 g) and hydroxylamine hydrochloride (3 equiv., 0.935 mol, 65.0 g). The mixture was stirred and heated at reflux for 2.5 hours and subsequently cooled to room temperature. The reaction mixture was poured into water (750 ml). The precipitate was isolated by filtration and washed with water. The crude precipitate was dissolved in THF (200 ml) and toluene (50 ml) and the mixture was evaporated, affording intermediate c (purity (LC) =80%). The crude product was used as such in the next reaction.

Intermediate c (0.312 mol, 58.7 g) was dissolved in acetic acid (300 ml). The mixture was heated at reflux for 2 hours and subsequently concentrated in vacuo. The residue was mixed with toluene (100 ml) and evaporated to a dry residue. Crystallization from ethanol (400 ml) gave crude intermediate d (31.0 g, purity (LC)=90%). Recrystallization in ethanol (300 ml) afforded d [C. Papamicael, G. Quéguiner, J. Bourguignon, G. Dupas *Tetrahedron* 2001, 57, 5385-5391] as brown crystals (29.4 g, yield=50%, purity (LC)>98%).

To cooled (0° C.) dry DMF (40 ml) was added dropwise phosphorus oxychloride (2.5 equiv., 0.199 mol, 30.6 g) and the reaction mixture was stirred for 30 min at 0° C. Then, a solution of d (0.080 mol, 15.0 g) in DMF (160 ml) was added and the reaction mixture was allowed to warm to room temperature overnight. The reaction mixture was poured into ice-water (2 liter) and stirred for 30 min. A brown precipitate was isolated by filtration and washed with water. The precipitate was dried for 24 hours in open air, affording intermediate e as a brown powder (6.10 g, yield=35%, purity (LC)=95%).

A mixture of intermediate e (0.005 mol, 1.13 g), Pd/C-catalyst (10%, 0.50 g) and triethylamine (6.8 equiv., 0.036 mol, 3.60 g) in THF (200 ml) was hydrogenated at atmospheric pressure for 2 hours. The catalyst was removed by filtration. The filtrate was evaporated to give f as a brown powder (0.88g, yield=92%, purity (LC)>95%).

To a mixture of intermediate f (0.005 mol, 0.880 g) and ethanol (5 ml) was added 3-chloroperoxybenzoic acid (1.2 equiv., 0.006 mol, 1.43 g of 70% mCPBA). The reaction mixture was heated at reflux for 2 hours. Pyridine (0.5 equiv., 0.002 mol, 0.190 g) was added and the mixture was heated at reflux for 30 min. The reaction mixture was cooled to room temperature and evaporated in vacuo. The residue was mixed with acetic anhydride (10 ml) and heated at reflux for 4 h and evaporated. The residue was dissolved in 2N potassium hydroxide (50 ml) and stirred for 1 h at room temperature. The pH of the reaction mixture was adjusted to pH=1 by the addition of concentrated hydrochloric acid. A brown precipitate was isolated by filtration. The precipitate was washed with a saturated sodium bicarbonate solution (2×10 ml), water, isopropanol and diisopropyl ether, affording intermediate g as a brown powder (0.680 g, yield=71%, purity (LC) >95%).

Example 2

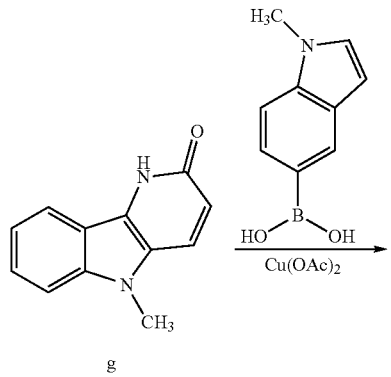

g

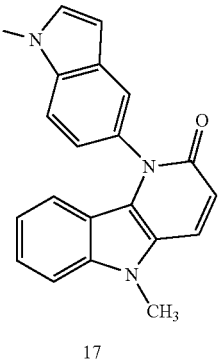

17

A mixture of intermediate g, prepared as outlined in example 1, (0.5045 mmol, 0.100 g), copper(I) acetate (1.50 equiv., 0.757 mmol, 0.137 g), N-methylindole-5-boronic acid (2.00 equiv., 1.01 mmol, 0.177 g), triethylamine (2.00 equiv., 1.01 mmol, 0.102 g), pyridine (2.0 equiv., 1.0 mmol, 0.080 g) and 300 mg powdered molecular sieves (4 Å) in dichloromethane (5 ml) was stirred overnight at room temperature, in a reaction vial provided with a calcium chloride tube. The reaction mixture was filtered over decalite. The decalite was washed with dichloromethane (100 ml) and the filtrate was washed with a saturated sodium bicarbonate solution (3×100 ml) and water (100 ml). The organic phase was evaporated under reduced pressure and the crude dark brown mixture was purified by reversed phase preparative HPLC affording compound 17 (0.092 g, yield=56%, purity (LC)>95%).

Example 3

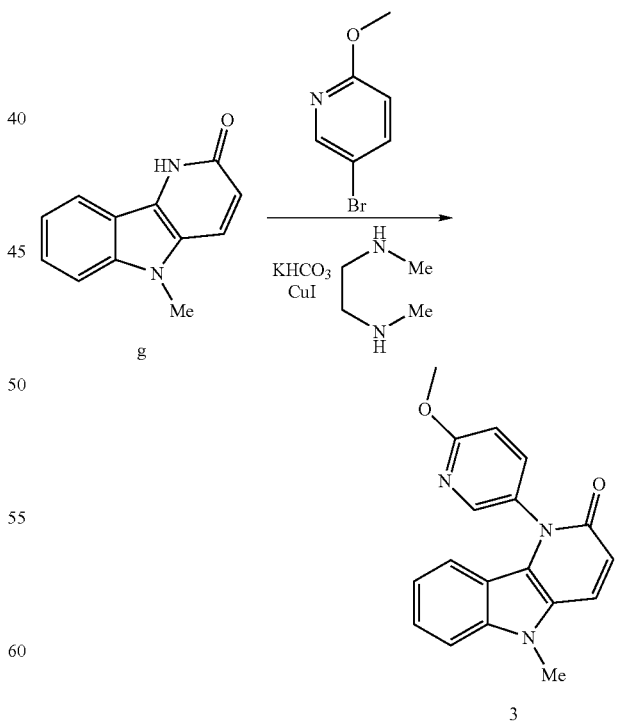

To a stirred suspension of compound g (0.25 mmol, 0.050 g) in 1,4-dioxane (1 ml) was added potassium hydrogen carbonate (2 equiv., 0.50 mmol, 0.050 g), copper(I) iodide (0.05 equiv., 0.01 mmol, 0.002 g), N,N'-dimethyl-ethane-1,2-diamine (0.1 equiv., 0.025 mmol, 0.002 g) and 5-bromo-2-methoxy-pyridine (1.2 equiv., 0.30 mmol, 0.057 g). The mixture was heated to reflux in a closed vial for 3 days. During this period, additional portions of copper(I) iodide, potassium hydrogen carbonate and N,N'-dimethyl-ethane-1,2-diamine were added twice to the reaction mixture. The mixture was filtered trough a pad of silica using a dichloromethane/methanol (9/1) mixture and was further purified by reversed phase preparative HPLC affording compound 3 (0.006 g, Yield: 8%, Purity (LC)=87%).

Example 4

The product was isolated by filtration. The crude product i was used as such in the next step.

The crude compound i was mixed with acetic anhydride (200 ml) and heated to reflux for 4 h. The mixture was evaporated to dryness under vacuum and the residual oil was mixed with 2N sodium hydroxide (10 equiv., 800 mmol, 400 ml of 2N NaOH) and heated to 50° C. for 1 h. Under cooling (ice bath), the solution was acidified by the slow addition of concentrated hydrochloric acid (100 ml), causing reaction product j to precipitate as a yellow powder. The powder was isolated by filtration and washed with water. The powder was mixed with methanol (300 ml) and heated to reflux for 30 min. After cooling to room temperature, the product was isolated

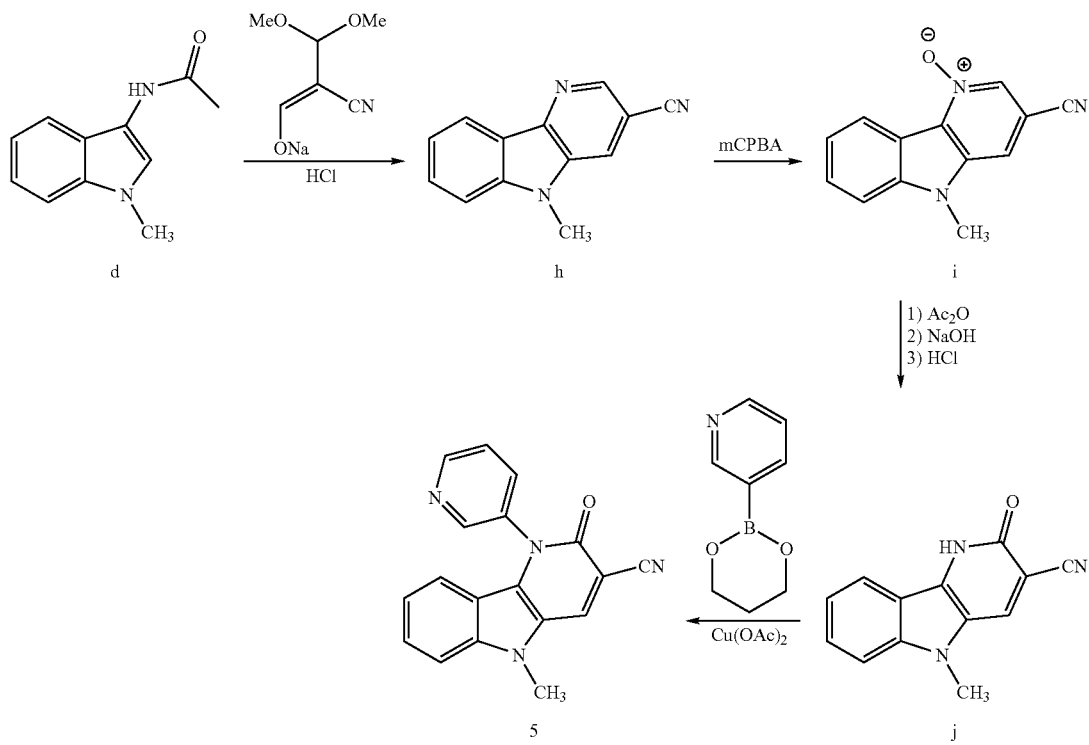

Intermediate d (79.7 mmol, 15.0 g), prepared as in example 1 and 3,3-dimethoxy-2-formyl-propionitrile sodium salt [R. B. G. Dupas, J. Bourguignon, G. Quéguiner *Synthesis* 1987, 1124] (2.0 equiv., 159 mmol, 26.3 g) were mixed in methanol (200 ml) and to the stirred suspension, concentrated hydrochloric acid (50 ml) was added dropwise. The reaction was heated at reflux for 3 h and cooled to room temperature. A yellow precipitate was isolated by filtration and washed with several portions of methanol. The powder, which consists of a hydrochloric acid salt of intermediate h was mixed with dichloromethane (500 ml) and water (200 ml) and potassium carbonate was added to the vigorously stirred mixture, until complete neutralisation (pH>7). The organic layer was separated and evaporated. The crude product h [C. Papamicaël, G. Quéguiner, J. Bourguignon, G. Dupas *Tetrahedron* 2001, 51, 5385] was used as such in the next step.

A mixture of crude compound h and m-chloroperbenzoic acid (1.1 equiv., 88 mmol, 21.7 g of 70% mCPBA) were heated to reflux in chloroform (200 ml) for 3 h. Upon cooling, the reaction product crystallised from the reaction mixture.

by filtration and dried overnight in an open recipient to provide compound j (12.56 g, yield=70% with respect to compound d, purity (LC)>97%).

A mixture of compound j (0.4569 mmol, 0.102 g), copper (II) acetate (1.47 equiv., 0.6717 mmol, 0.122 g), 3-pyridineboronic acid 1,3-propanediol cyclic ester (2.0 equiv., 0.9081 mmol, 0.148 g), triethylamine (2.0 equiv., 0.8993 mmol, 0.091 g) and pyridine (2.0 equiv., 0.8976 mmol, 0.071 g) in dichloromethane (5 ml) was stirred for 60 h at room temperature in a reaction vial provided with a calcium chloride tube. The reaction mixture was filtered over decalite and the decalite was washed with dichloromethane (200 ml). The filtrate was washed with a saturated sodium bicarbonate solution (3×100 ml) and water (100 ml). The organic phase was evaporated under reduced pressure. The yellow-brown residue was dissolved in DMF (0.5 ml). This mixture was poured out into water (5 ml) and stirred for ½ h. at room temperature. After filtration, the precipitate was washed with isopropanol and diisopropylether, affording compound 5 as a yellow-brown solid product (0.020 g, yield=13%, purity (LC)=89%).

Example 5

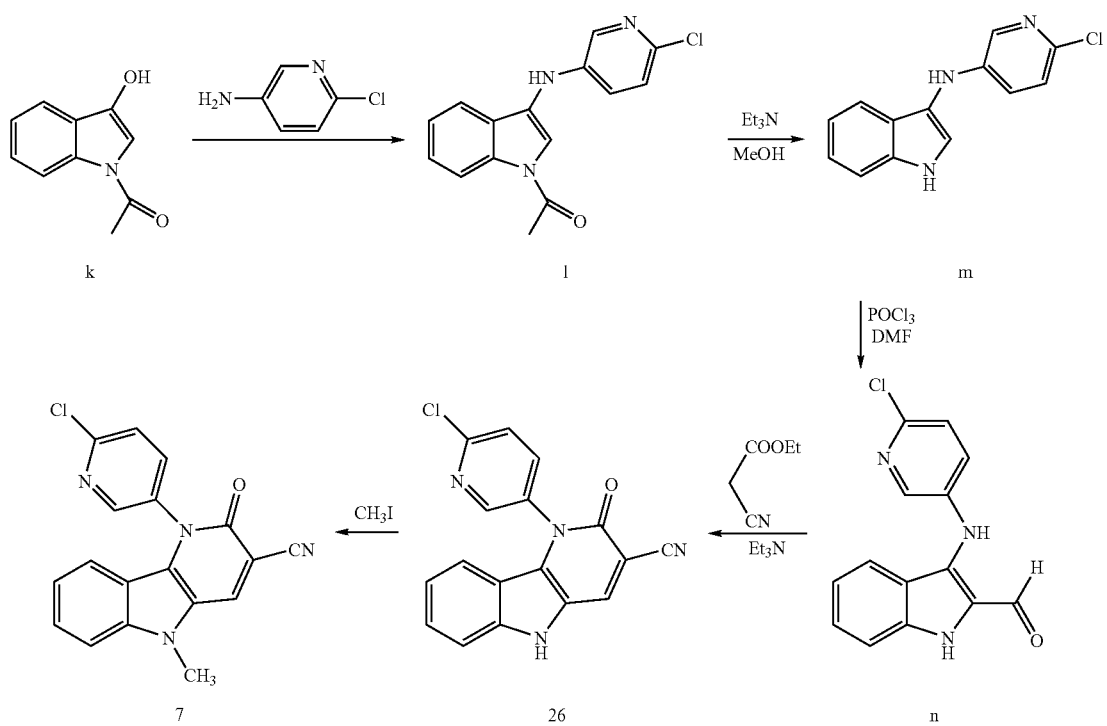

To a mixture of N-acetyl-3-hydroxyindole (k) (0.065 mol, 11.39 g) in toluene (70 ml), was added 5-amino-2-chloropyridine (1.2 equiv., 0.078 mol, 10.00 g) and a pinch of p-toluenesulfonic acid. The mixture was heated at 130° C. for 10 h with azeotropic distillation of water. The reaction mixture was cooled to room temperature, a purple precipitate was filtered off and washed with diisopropyl ether, affording compound 1 (18.12 g, yield=97%).

Compound 1 (0.063 mol, 18.12 g) was mixed with methanol (200 ml) and triethylamine (1.50 equiv., 0.095 mol, 9.63 g) and the mixture was heated at reflux for 3 hours, cooled to room temperature and evaporated under reduced pressure to a dry powder. The crude product m (15.33 g, purity (LC)>80%) was used as such in the next step.

To ice-cooled DMF (70 ml) was added dropwise phosphorus oxychloride (3 equiv., 0.189 mol, 28.93 g) keeping the internal temperature<10° C. and the cooled mixture was stirred for 30 min. Then, a solution of crude compound m (0.063 mol, 15.33 g) in DMF (130 ml) was added dropwise, keeping the reaction temperature<10° C. during the addition. The ice-bath was removed and the reaction mixture was stirred at room temperature for 30 min. The mixture was poured into ice-water (1000 ml). The precipitate was isolated by filtration and washed with water. The compound was mixed with toluene (200 ml) and evaporated under reduced pressure to afford compound n (4.28 g, yield=25%).

To a mixture of compound n (0.008 mol, 2.29 g) in isopropanol (30 ml) was added triethylamine (1.5 equiv., 0.013 mol, 1.28 g) and ethyl cyanoacetate (0.010 mol, 1.14 g). The mixture was heated at reflux for 3 hours, cooled to room temperature, filtered and the residue was successively washed with isopropanol and diisopropyl ether to afford compound 26 (1.09 g, yield=40%, purity (LC)>98%) as a brownish powder.

To a mixture of compound 26 (3.40 mmol, 1.09 g) in DMF (10 ml) was added potassium carbonate (1.25 equiv., 4.25 mmol, 0.59 g) and methyl iodide (1.30 equiv., 5.75 mmol, 0.82 g) and the mixture was heated at 50° C. for 3 hours. The reaction mixture was cooled to room temperature and evaporated under reduced pressure to a dry residue. The residue was mixed with dichloromethane and washed with water. The organic phase was dried (MgSO$_4$), filtered and evaporated under reduced pressure affording compound 7 (1.11 g, yield=98%, purity (LC)>95%).

Example 6

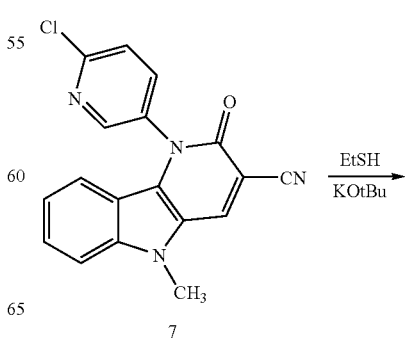

-continued

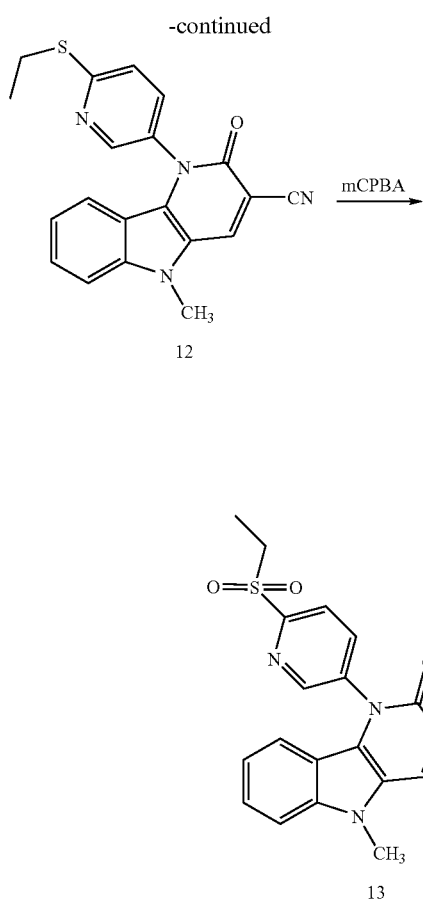

To a mixture of compound 7 (1.0 mmol, 0.34 g) in THF (10 ml) was added potassium tert-butoxide (1.55 equiv., 1.55 mmol, 0.17 g) and ethanethiol (1.60 equiv., 1.60 mmol, 0.99 g) and molecular sieves. The mixture was heated at 70° C. for 8 hours in a sealed vial. To the cooled reaction mixture was added again potassium tert-butoxide (1.55 equiv., 1.55 mmol, 0.17 g) and ethanethiol (1.60 equiv., 1.60 mmol, 0.99 g) and the mixture was heated at 70° C. in a sealed tube for another 5 hours. The cooled reaction mixture was evaporated under reduced pressure. The residue was mixed with dichloromethane and washed with water. The organic phase was dried (MgSO₄), filtered and evaporated under reduced pressure to give a dry residue. Purification using column chromatography (silica gel, eluent: 1% methanol in dichloromethane) gave crude compound 12 (0.18 g, yield=48%, purity (LC)=70%).

To a cooled (0° C.) mixture of compound 12 (0.07 mmol, 0.025 g) in dichloromethane (1 ml) was added 3-chloroperoxybenzoic acid (2.50 equiv., 0.17 mmol, 0.043 g). The mixture was stirred at room temperature for 48 h. The reaction mixture was diluted with dichloromethane (5 ml) and washed with a saturated sodium bicarbonate solution. The organic phase was dried (MgSO₄), filtered and evaporated under reduced pressure to give a dry residue. Purification using column chromatography (Silica gel, eluent: ethyl acetate/heptane: 80/20) afforded compound 13 (4.2 mg, yield=15%, purity (LC)=97%).

Example 7

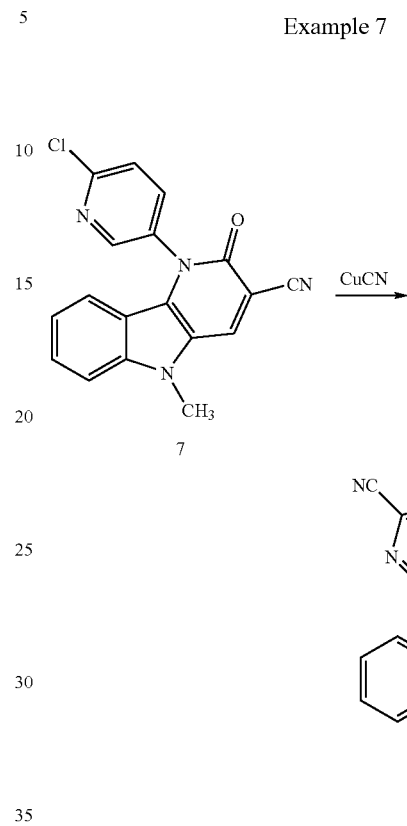

To a mixture of compound 7 (0.45 mmol, 0.15 g) in DMF (2.0 ml) was added copper(I) cyanide (2.00 equiv., 0.90 mmol, 0.080 g). The mixture was heated in a microwave (300W) at 170° C. in a sealed tube for 45 min. The reaction mixture was evaporated under reduced pressure to give a dry residue. The residue was washed successively with a saturated sodium bicarbonate solution and water. The precipitate was evaporated under reduced pressure to give a dry residue. Purification using column chromatography (silica gel, eluent: 1% methanol in dichloromethane) afforded compound 14 as a yellow powder (4.2 mg, yield=2.9%, purity (LC)=80%).

Example 8

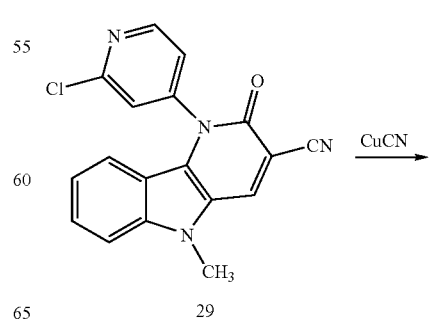

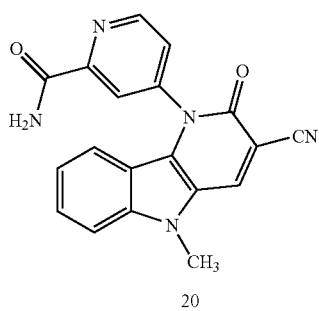

20

To a mixture of compound 29 (0.30 mmol, 0.100 g) in DMF (3.0 ml) was added copper(I) cyanide (3.00 equiv., 0.90 mmol, 0.080 g). The mixture was heated in a microwave (200W) at 170° C. in a sealed tube for 20 minutes. The reaction mixture was poured into a saturated sodium bicarbonate solution. The precipitate was filtered off, washed with water and further purified using preparative reversed phase HPLC to afford compound 20 (4.3 mg, yield=2.5%, purity (LC)=60%).

Example 9

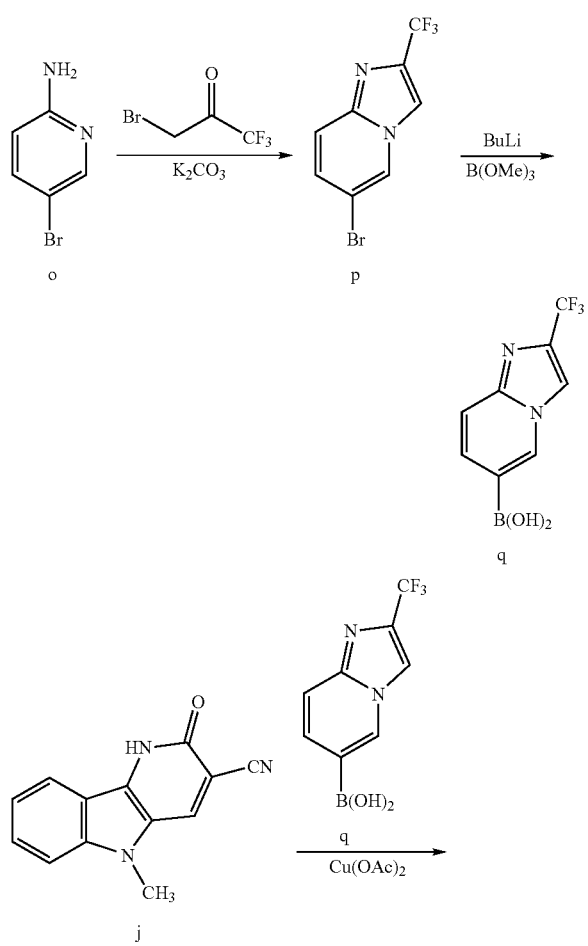

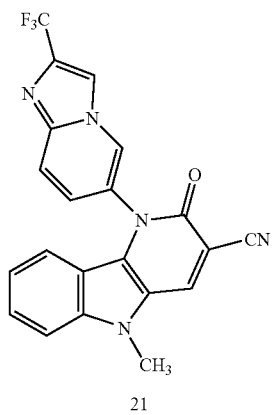

21

To a mixture of 2-amino-5-bromo-pyridine o (11.6 mmol, 2.0 g) in ethanol (50 ml) was added 3-bromo-1,1,1-trifluoroacetone (2.1 equiv., 24.3 mmol, 4.64 g) and potassium carbonate (1.5 equiv., 17.3 mmol, 2.40 g). The mixture was heated at reflux for 24 hours and evaporated under reduced pressure. The residue was partitioned between a diluted aqueous sodium bicarbonate solution (100 ml) and dichloromethane (100 ml). The organic layer was dried ($MgSO_4$) and evaporated under reduced pressure. The residue was triturated with diisopropylether (20 ml) and filtered. The filtrate was evaporated under reduced pressure and the residue was triturated with petroleum ether (20 ml). The solids were isolated by filtration affording 6-bromo-2-trifluoromethyl-imidazo[1,2-a]pyridine p (3.0 g, yield=98%).

To a cooled (−78° C.) solution of 6-bromo-2-trifluoromethyl-imidazo[1,2-a]pyridine p (5.66 mmol, 1.50 g) and trimethyl borate (1.2 equiv., 6.79 mmol, 0.706 g) in diethyl ether (7 ml) under $N_2$-atmosphere was added dropwise butyl-lithium (1.2 equiv., 6.79 mmol, 2.72 ml of a solution 2.5 M BuLi in hexane) over a period of 10 minutes. After 30 min, the solution was warmed to −20° C. and 2N hydrochloric acid (7.5 ml) was added dropwise. The mixture was partitioned between water (50 ml) and diethyl ether (50 ml). The aqueous layer was isolated and the pH of the solution was adjusted to pH=7 by the addition of sodium bicarbonate. The aqueous solution was extracted with ethyl acetate. The combined organic layers were dried ($MgSO_4$) and evaporated under reduced pressure affording 2-trifluoromethyl-imidazo[1,2-a]pyridine-6-boronic acid q (0.23 g, yield=11.4%, purity (LC) =67%).

To a stirred solution of compound j (0.45 mmol, 100 mg) in dichloromethane (3.0 ml) were added powdered molecular sieves (600 mg), copper acetate (1.5 equiv., 0.67 mmol, 122 mg), 2-trifluoromethyl-imidazo[1,2-a]pyridine-6-boronic acid p (2.0 equiv., 0.90 mmol, 206 mg), pyridine (2.0 equiv., 0.90 mmol, 71 mg) and triethylamine (2.0 equiv., 0.90 mmol, 91 mg). Air was allowed to diffuse into the reaction mixture via a $CaCl_2$-tube on top of the flask. The mixture was stirred at room temperature for 5 days and filtered over decalite. The filter was thoroughly washed with a mixture of tetrahydrofuran/dichloromethane (9/1). The filtrate was washed with a saturated sodium bicarbonate solution (2×100 ml) and water (100 ml). The organic layer was evaporated under reduced pressure and the residue was purified using reversed phase preparative HPLC to afford compound 21 (15 mg, yield=8%, purity (LC)=60%).

Example 10

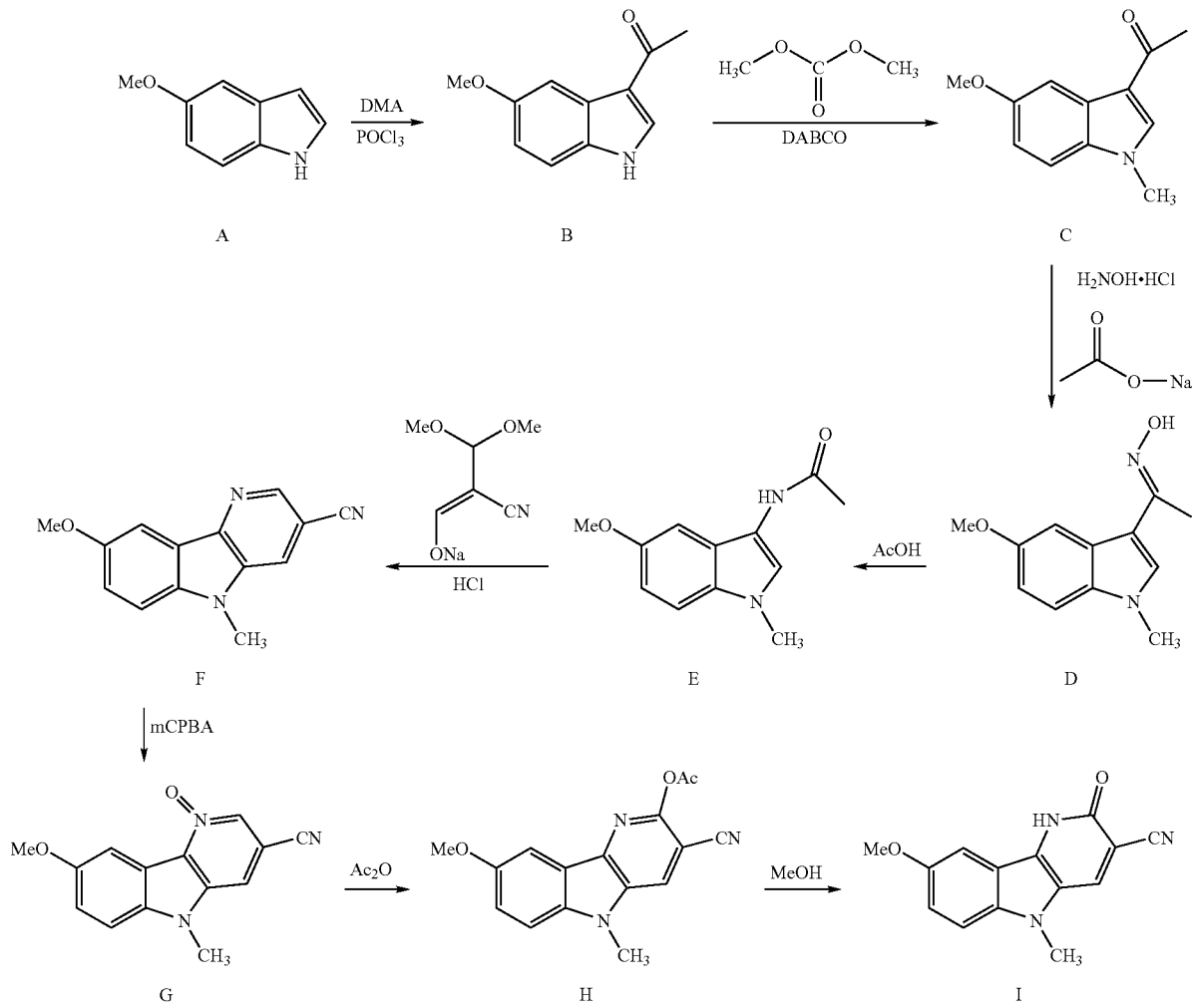

solution was extracted with dichloromethane (2×300 ml), dried (MgSO$_4$) and evaporated under reduced pressure, affording intermediate C (7.64 g, yield=98%).

To a mixture of intermediate C (38 mmol, 7.64 g) in ethanol (70 ml) and water (35 ml) was added sodium acetate (2.40 equiv., 90 mmol, 7.4 g) and hydroxylamine hydrochloride (3.0 equiv., 113 mmol, 7.8 g). The reaction mixture was heated at reflux for 3 hours, cooled to room temperature and most of the ethanol was stripped off under reduced pressure. The remaining aqueous suspension was mixed with a saturated sodium bicarbonate solution to pH=7. The precipitate was filtered off and washed with water. The solid was taken up in toluene and evaporated under reduced pressure to afford 7.7 g of a mixture of intermediate D (91%) and intermediate E (8.5%). Then the mixture was dissolved in acetic acid (30 ml) and heated at reflux for 2 hours. The solvent was evaporated under reduced pressure, and the residue was purified using column chromatography on silica gel (eluent: ethylacetate:dichloromethane 2:8) to afford intermediate E (3.75 g, yield=49%).

To a mixture of intermediate E (19.2 mmol, 4.20 g) and 2-hydroxymethylene 3,3-dimethoxypropionitrile sodium salt$^{ref}$ (1.50 equiv., 28.9 mmol, 4.77 g) in methanol (50 ml), Phosphorus oxychloride (1.30 equiv., 104 mmol, 15.90 g) was added dropwise to dimethylacetamide (30 ml) while the reaction temperature was kept under 20° C. After stirring for ½ h, a solution of 5-methoxyindole A (80 mmol, 11.80 g) in dimethylacetamide (30 ml) was added and reaction mixture was heated at 90° C. for 2 h and subsequently stirred at room temperature for 16 h. The mixture was poured into ice-water (500 ml). The aqueous layer was basified with 50% NaOH (30 ml) until pH =14 and filtered. The precipitate was washed with water and recrystallized from methanol (200 ml), affording intermediate B (7.83 g, yield=52%, purity (LC)>95%).

To a mixture of 3-acetyl-5-methoxyindole B (0.038 mol, 7.2 g) in dry DMF (20 ml), was added diazabicyclo[2.2.2]octane (0.10 equiv., 0.004 mol, 0.43 g) and dimethylcarbonate (2.0 equiv., 0.076 mol, 6.86 g). The reaction mixture was heated at 100° C. for one week and evaporated under reduced pressure. The residue was mixed with water (100 ml) and the pH was adjusted to 3 with 1N hydrochloric acid. The aqueous concentrated hydrochloric acid (15 ml) was added. The reaction mixture was heated under reflux for 4 h. After cooling to room temperature, the precipitate was isolated by filtration, and washed with isopropanol and diisopropyl ether affording intermediate F (5.20 mg, yield=98%, purity (LC)=99%) as its hydrochlorate.

Intermediate F (20.0 mmol, 5.47 g) was mixed with chloroform (1.5 liters) and an aqueous saturated sodium carbonate solution (200 ml) and vigorously stirred for 15 min. The organic layer was isolated and concentrated to a residual volume of 150 ml, 3-chloroperbenzoic acid (1.2 equiv., 24 mmol, 5.92 of 70% mCPBA) was added and the mixture was heated to reflux for 2 h. The reaction mixture was cooled to room temperature, diluted with chloroform to a total volume of 800 ml and washed with an aqueous sodium carbonate solution (2×200 ml). The organic layer was dried (MgSO$_4$), filtered and evaporated to a dry residue. The residue was dissolved in acetic anhydride (60 ml) and heated to reflux for 3 h. The reaction mixture was evaporated under reduced pressure to a dry dark residue. The residue was mixed with methanol (100 ml) and triethylamine (2 ml) and heated under reflux for 4 h. The mixture was allowed to cool to room temperature, the precipitate was filtered off and washed with isopropanol and diisopropylether to afford intermediate 1 (1.92 g, yield=38%, purity (LC)=99%) as a yellow powder.

Example 11

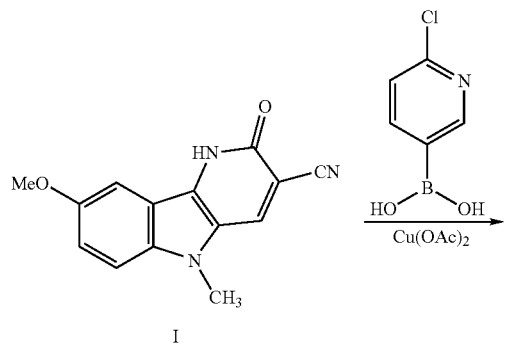

I

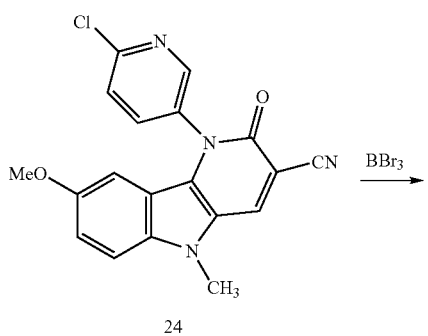

24

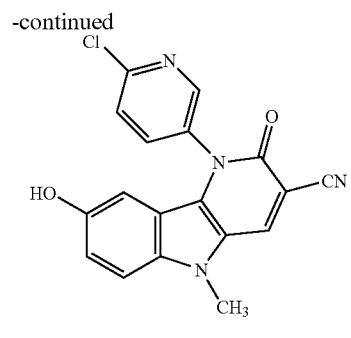

43

To a mixture of intermediate I (0.24 mmol, 100 mg) in dichloromethane (5.0 ml) were added powdered molecular sieves (600 mg), copper acetate (2.0 equiv., 0.48 mmol, 86 mg), 4-chloropyridine boronic acid (2.0 equiv., 0.48 mmol, 75 mg), pyridine (2.0 equiv., 0.48 mmol, 37 mg) and triethylamine (2.0 equiv., 0.48 mmol, 48 mg). Air was allowed to diffuse into the reaction mixture via a CaCl$_2$-tube on top of the flask. The mixture was stirred at room temperature for 8 days. The reaction mixture was filtered over a path of decalite. The filter aid was thoroughly washed with a mixture of tetrahydrofuran/dichloromethane (9/1). The filtrate was washed with a saturated sodium bicarbonate solution (2×100 ml) and water (100 ml). The organic layer was evaporated under reduced pressure and the residue was chromatographed on a silica gel column eluting with a mixture of tetrahydrofuran/dichloromethane (97.5/2.5) affording compound 24 (24 mg, yield=24%, purity (LC)=86%).

To the ice-cooled mixture of compound 24 (0.06 mmol, 22 mg) in dichloromethane (2 ml), under a nitrogen atmosphere, was added boron tribromide (20 equiv., 1.2 mmol, 1.2 ml of a 1M BBr$_3$ solution in dichloromethane). The mixture was stirred at room temperature for 3 hours and then poured into an ice-cold saturated sodium bicarbonate solution (50 ml). The product was partitioned between a diluted sodium bicarbonate solution (50 ml) and dichloromethane (50 ml) and the organic phase was evaporated under reduced pressure. The residue was chromatographed on a silica gel column eluting with a mixture of tetrahydrofuran/dichloromethane (97/3) affording compound 43 (7.2 mg, yield=33%, purity (LC)=90%).

The following table lists examples of compounds of the present invention which compounds are prepared analogous those of the foregoing synthesis schemes.

In the following table the column headed "rf" lists the retention times and the column "(M+H)$^+$" lists the mass of the molecule ions.

Retention times were measured using the following equipment: HPLC-system:

Waters Alliance 2790 (pump+auto sampler), Waters 996 (Photo diode array-detector);

Column: Waters XTerra MS C18 2.5 μm 50×4.6 mm. The following were the measurement parameters:

Temperature: 30° C.

Mobile phase: A: 10 mM HCOONH4+0.1% HCOOH in H$_2$O

B: 0.1% HCOOH in CH$_3$CN

Gradient: 0 min: 15% B, 5 min: 95% B, 7 min: 95% B

Equilibration time: 2 min

Flow: 1.2 ml/min

Injection volume: 3 ul of a 1 mg/ml solution

The molecular ion was determined using the following MS-detector: Waters LCT; ionisation: electrospray in positive or negative mode.

TABLE 2

| Comp. No. | Synthesis Example | R¹ | R² | R³ | R²⁰ | (M + H)⁺ | rf |
|---|---|---|---|---|---|---|---|
| 1 | 2 | H | CH₃ | 3-thienyl | H | 281 | 3.08 |
| 2 | 2 | H | CH₃ | 3-furanyl | H | 265 | 2.90 |
| 3 | 3 | H | CH₃ | 2-methoxy-5-pyridinyl | H | 306 | 2.99 |
| 4 | 2 | H | CH₃ | 2-chloro--5-pyridinyl | H | | |
| 5 | 2 | H | CH₃ | 3-pyridinyl | H | 276 | 3.50 |
| 6 | 2 | H | CH₃ | benzothien-2-yl | H | 331 | 3.83 |
| 7 | 5 | CN | CH₃ | 2-chloro-5-pyridinyl | H | 335 | 3.28 |
| 8 | 4 | CN | CH₃ | 1-methyl-5-methylindol-3-yl | H | 353 | 3.72 |
| 9 | 4 | CN | CH₃ | 3-quinolinyl | H | 351 | 3.32 |
| 10 | 2 | H | CH₃ | 2-bromo-5-pyridinyl | H | 355 | 3.14 |
| 11 | 4 | CN | CH₃ | 5-pyrimidinyl | H | 302 | 2.51 |
| 12 | 6 | CN | CH₃ | 5-methyl-2-(ethylthio)pyridin-yl | H | 361 | 3.87 |
| 13 | 6 | CN | CH₃ | 5-methyl-2-(ethylsulfonyl)pyridinyl | H | 393 | 2.99 |
| 14 | 7 | CN | CH₃ | 2-cyano-5-pyridinyl | H | 326 | 3.72 |
| 15 | 4 | CN | CH₃ | 3-pyridinyl | H | | |
| 16 | 9 | CN | CH₃ | 6-methylimidazo[1,2-a]pyridin-yl | H | 340 | 1.94 |
| 17 | 2 | H | CH₃ | 1-methyl-5-methylindol-3-yl | H | 328 | 3.39 |
| 18 | 2 | H | CH₃ | 5-pyrimidinyl | H | 277 | 2.33 |
| 19 | 5 | CN | H | 2-chloro-4-pyridinyl | H | 321 | 2.95 |
| 20 | 8 | CN | CH₃ | 4-methyl-2-carbamoylpyridin-yl | H | 344 | 2.70 |

TABLE 2-continued

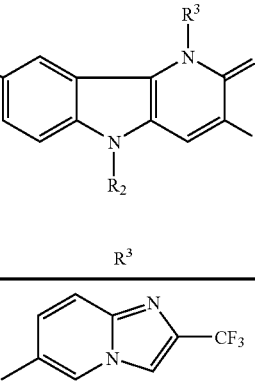

| Comp. No. | Synthesis Example | R¹ | R² | R³ | R²⁰ | (M + H)⁺ | rf |
|---|---|---|---|---|---|---|---|
| 21 | 9 | CN | CH₃ | 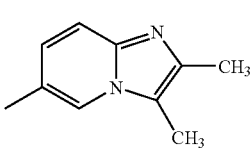 | H | 408 | 3.36 |
| 22 | 9 | CN | CH₃ | 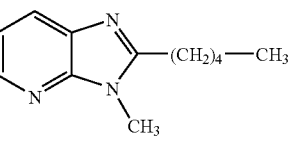 | H | 368 | 2.11 |
| 23 | 9 | CN | CH₃ | 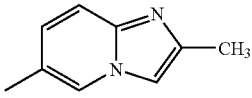 | H | | |
| 24 | 11 | CN | CH₃ | 2-chloro-5-pyridinyl | —OCH₃ | 365 | 3.39 |
| 25 | 11 | CN | CH₃ | 2-methyl-5-pyridinyl | —OCH₃ | 345 | 2.85 |
| 26 | 5 | CN | H | 2-chloro-5-pyridinyl | H | 321 | 2.99 |
| 27 | 2 | H | CH₃ | 3-quinolinyl | H | 326 | 3.10 |
| 28 | 4 | CN | CH₃ | 2-bromo-5-pyridinyl | H | 379 | 3.47 |
| 29 | 5 | CN | CH₃ | 2-chloro-4-pyridinyl | H | 335 | 3.25 |
| 30 | 9 | CN | CH₃ | 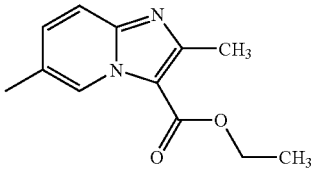 | H | 354 | 1.90 |
| 31 | 9 | CN | CH₃ | 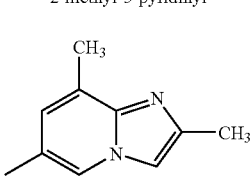 | H | 426 | 3.39 |
| 32 | 4 | CN | CH₃ | 2-methyl-5-pyridinyl | H | 315 | 2.81 |
| 33 | 9 | CN | CH₃ | 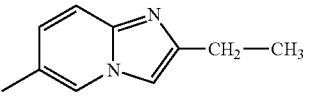 | H | 368 | 2.07 |
| 34 | 4 | CN | CH₃ | 2-chloro-3-methyl-5-pyridinyl | H | 349 | 3.57 |
| 35 | 4 | CN | CH₃ | 2-methoxy-5-pyridinyl | H | 331 | 3.32 |
| 36 | 4 | CN | CH₃ | 2-fluoro-5-pyridinyl | H | 319 | 3.14 |
| 37 | 4 | CN | CH₃ | 2-methoxy-5-pyrimidinyl | H | 332 | 2.92 |
| 38 | 4 | CN | CH₃ | 2-methoxy-5-pyridinyl | H | 331 | 2.88 |
| 39 | 9 | CN | CH₃ |  | H | 368 | 2.14 |

TABLE 2-continued

[Structure: tricyclic pyrido-indole core with substituents R1, R2, R3, R20]

| Comp. No. | Synthesis Example | R¹ | R² | R³ | R²⁰ | (M + H)⁺ | rf |
|---|---|---|---|---|---|---|---|
| 40 | 9 | CN | CH₃ | [7-methyl-imidazo[1,2-a]pyridin-2-yl with CH₃] | H | 354 | 2.70 |
| 41 | 9 | CN | CH₃ | [1,2-dimethyl-6-methyl-imidazo[4,5-b]pyridin-yl] | H | 369 | 2.40 |
| 42 | 11 | CN | CH₃ | 2-bromo-5-pyridinyl | —OCH₃ | 409 | 2.54 |
| 43 | 11 | CN | CH₃ | 2-chloro-5-pyridinyl | —OH | 351 | 2.55 |
| 44 | 11 | CN | CH₃ | 2-methyl-5-pyridinyl | —OH | 331 | 2.15 |
| 45 | 11 | CN | CH₃ | 2-bromo-5-pyridinyl | —OH | 395 | 2.66 |
| 46 | 11 | CN | CH₃ | 2-chloro-3-methyl-5-pyridinyl | —OH | | |

Example 12

In Vitro Inhibition of HIV Reverse Transcriptase

The assay was run using kit TRK 1022 (Amersham Life Sciences) according to the manufacturer's instructions with slight modifications. Compounds were diluted in steps of 1/4 in 100% DMSO and subsequently transferred to Medium A (1/50 dilution; medium A: RPMI 1640+10% FetalClone II+Gentamycin 20 mg/L). 25 μl of compound (in 2% DMSO in Medium A) or 25 μl of 2% DMSO in medium A was added to wells. To each well was added 25.5 μl master mix (master mix: 5 μl primer/template beads, 10 μl assay buffer, 0.5 μl tracer (3H-TTP), 5 μl HIV RT enzyme solution at a final enzyme activity of 15 mU per 50 μl reaction, 5 μl medium A). The plates were sealed, marked as radioactive and incubated during 4 hours at 37° C. Subsequently, 100 μl stop solution was added to each well (except R1). The radioactivity was counted in a TopCount.

Example 13

Cellular Assay

The compounds of the present invention were examined for anti-viral activity in a cellular assay, which was performed according to the following procedure.

HIV- or mock-infected MT4 cells were incubated for five days in the presence of various concentrations of the inhibitor. At the end of the incubation period, the replicating virus in the control cultures has killed all HIV-infected cells in the absence of any inhibitor. Cell viability was determined by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution was monitored at 540 nm. The values correlate directly to the number of living cells remaining in the culture at the completion of the five day incubation. The inhibitory activity of the compound was monitored on the virus-infected cells and was expressed as $EC_{50}$ and $EC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor. Wherever results are reported as e.g. $pEC_{50}$ or $pCC_{50}$ values, the result is expressed as the negative logarithm of the result expressed as $EC_{50}$ or $CC_{50}$ respectively.

The following table lists the $pEC_{50}$ values for a number of compounds of the present invention.

| Comp. No. | pEC₅₀ |
|---|---|
| 6 | 4.9 |
| 7 | 6.1 |
| 9 | 5.6 |
| 10 | 5.7 |
| 11 | 4.7 |
| 12 | 5.3 |
| 14 | 5.0 |
| 17 | 5.2 |
| 19 | 4.8 |
| 20 | 5.3 |
| 21 | 4.9 |
| 26 | 5.6 |
| 27 | 5.2 |
| 28 | 5.5 |
| 32 | 6.0 |
| 33 | 5.8 |
| 34 | 6.1 |
| 35 | 5.5 |

-continued

| Comp. No. | pEC$_{50}$ |
|---|---|
| 36 | 5.1 |
| 37 | 5.6 |
| 43 | 5.4 |

Example 14

Formulations

Capsules

Active ingredient, in casu a compound of formula (I), is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, are dissolved in organic solvents such as ethanol, methanol methylene chloride. Suitably the polymer is dissolved in ethanol. The polymer and compound solutions are mixed and subsequently spray dried. The ratio of compound/polymer is selected from 1/1 to 1/6. Intermediate ranges can be 1/1.5 and 1/3. A suitable ratio can be 1/6. The spray-dried powder, a solid dispersion, is subsequently filled in capsules for administration. The drug load in one capsule ranges between 50 and 100 mg depending on the capsule size used.

Film-Coated Tablets

Preparation of Tablet Core

A mixture of 100 g of a compound of formula (I), 570 g lactose and 200 g starch are mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10,000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

The invention claimed is:

1. A compound of formula (I):

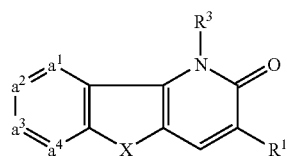

(I)

or pharmaceutically acceptable salts thereof, wherein
$R^1$ is hydrogen or cyano;
X is a bivalent radical $NR_2$;
$R^2$ is:

i) hydrogen, $C_{1-10}$alkyl, $C_{2-10}$alkenyl, $C_{3-7}$cycloalkyl, wherein said $C_{1-10}$alkyl, $C_{2-10}$alkenyl and $C_{3-7}$cycloalkyl, each individually and independently, may be optionally substituted with a substituent selected from the group consisting of cyano, $N(R^{16a}R^{16b})$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $N(R^{16a}R^{16b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-ylcarbonyl, thiomorpholin-1-ylcarbonyl, 1-oxothiomorpholin-1-ylcarbonyl and 1,1-dioxo-thiomorpholin-1-ylcarbonyl; or $R^2$ is ii) aryl substituted with a radical —COOR$^4$; or $R^2$ is iii) $C_{1-10}$alkyl, $C_{2-10}$alkenyl, $C_{3-7}$cycloalkyl, each of said $C_{1-10}$alkyl, $C_{2-10}$alkenyl, $C_{3-7}$cycloalkyl, each individually and independently, being substituted with aryl wherein said aryl is substituted with a radical —COOR$^4$; or $R^2$ is iv) $C_{1-10}$alkyl, $C_{2-10}$alkenyl, $C_{3-7}$cycloalkyl, each individually and independently, substituted with a radical selected from —NR$^{5a}$—C(=NR$^{5b}$)—NR$^{5c}$R$^{5d}$, —NR$^{5a}$—C(=NR$^{5e}$)—R$^{5f}$, —O—NR$^{5a}$—C(=NR$^{5b}$)—NR$^{5c}$R$^{5d}$, —O—NR$^{5a}$—C(=NR$^{5e}$)—R$^{5f}$, -sulfonyl-R$^6$, —NR$^7$R$^8$, —NR$^9$R$^{10}$, a radical

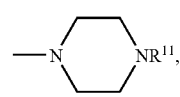
(a-1)

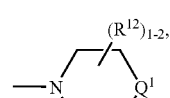
(a-2)

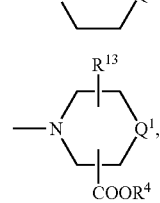
(a-3)

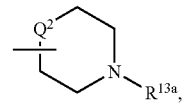
(a-4)

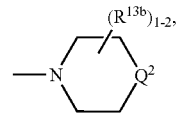
(a-5)

wherein each $Q^1$ independently is a direct bond, —CH$_2$—, or —CH$_2$—CH$_2$—;

each $Q^2$ independently is O, S, SO or SO$_2$;

each $R^4$ independently is hydrogen, $C_{1-4}$alkyl, aryl$C_{1-4}$alkyl;

each $R^{5a}$, $R^{5b}$, $R^{5c}$, $R^{5d}$ independently is hydrogen, $C_{1-4}$alkyl or aryl$C_{1-4}$alkyl;

each $R^{5e}$, $R^{5f}$ independently is hydrogen, $C_{1-4}$alkyl or aryl$C_{1-4}$alkyl, or $R^{5e}$ and $R^{5f}$, taken together may form a bivalent alkanediyl radical of formula —$CH_2$—$CH_2$— or —$CH_2$—$CH_2$—$CH_2$—;

$R^6$ is $C_{1-4}$alkyl, —$N(R^{5a}R^{5b})$, $C_{1-4}$alkyloxy, pyrrolidin-1-yl, piperidin-1-yl, homopiperidin-1-yl, piperazin-1-yl, 4-($C_{1-4}$alkyl)-piperazin-1-yl, morpholin-4-yl-, thiomorpholin-4-yl-, 1-oxothiomorpholin-4-yl and 1,1-dioxo-thiomorpholin-4-yl;

$R^7$ is hydrogen, $C_{1-4}$alkyl, hydroxy$C_{1-4}$alkyl, $C_{1-4}$alkoxy$C_{1-4}$alkyl or $C_{1-4}$alkylcarbonyloxy$C_{1-4}$alkyl;

$R^8$ is hydroxy$C_{1-4}$alkyl, $C_{1-4}$alkoxy$C_{1-4}$alkyl, $C_{1-4}$alkylcarbonyloxy$C_{1-4}$alkyl, aryl or aryl$C_{1-4}$alkyl;

$R^9$ is hydrogen or $C_{1-4}$alkyl;

$R^{10}$ is $Het_1$, $Het_2$ or a radical

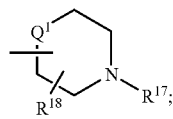

(a-6)

$R^{11}$ is aryl, aryl$C_{1-4}$alkyl, formyl, $C_{1-4}$alkylcarbonyl, arylcarbonyl, aryl$C_{1-4}$alkylcarbonyl, $C_{1-4}$alkyloxycarbonyl, aryl$C_{1-4}$alkyloxycarbonyl, $R^{5a}R^{5b}$N-carbonyl, hydroxy$C_{1-4}$alkyl, $C_{1-4}$alkyloxy$C_{1-4}$alkyl, aryl$C_{1-4}$alkyloxy$C_{1-4}$alkyl, aryloxy$C_{1-4}$alkyl, $Het_2$;

each $R^{12}$ independently is hydroxy, $C_{1-4}$alkyl, aryl$C_{1-4}$alkyl, $C_{1-4}$alkyloxy, aryl$C_{1-4}$alkyloxy, oxo, spiro($C_{2-4}$alkanedioxy), spiro(di$C_{1-4}$alkyloxy), —$NR^{5a}R^{5b}$;

$R^{13}$ is hydrogen, hydroxy, $C_{1-4}$alkyl, $C_{1-4}$alkyloxy, or aryl$C_{1-4}$alkyloxy; or $R^{13a}$ is $C_{1-4}$alkyl, aryl$C_{1-4}$alkyl, $C_{1-4}$alkyloxycarbonyl or aryl$C_{1-4}$alkyloxycarbonyl;

each $R^{13b}$ is hydrogen or $C_{1-4}$alkyl; or $R^2$ is v) a radical of formula:

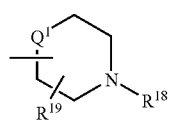

(b-1)

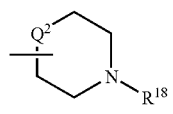

(b-2)

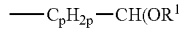 (b-3)
—$C_pH_{2p}$—$CH(OR^{14})$—$C_qH_{2q}$—$R^{15}$;

 (b-4)
—$CH_2$—$CH_2$—(O—$CH_2$—$CH_2$)$_m$—$OR^{14}$;

 (b-5)
—$CH_2$—$CH_2$—(O—$CH_2$—$CH_2$)$_m$—$NR^{17a}R^{17b}$;

wherein in radical (b-3) one of the hydrogen atoms in —$C_pH_{2p}$— and one of the hydrogen atoms in —$CH(OR^{14})$—$C_qH_{2q}$—, that is not part of $R^{14}$, may be replaced by a direct bond or a $C_{1-4}$alkanediyl group;

p is 1, 2 or 3;
q is 0, 1, 2 or 3;
m is 1 to 10;
each $R^{14}$ independently is hydrogen, $C_{1-4}$alkyl, aryl$C_{1-4}$alkyl, aryl, $C_{1-4}$alkylcarbonyl, —$SO_3H$, —$PO_3H_2$;

$R^{15}$ is a substituent selected from the group consisting of cyano, $NR^{16a}R^{16b}$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxy-carbonyl, $C_{1-4}$alkylcarbonyl, $N(R^{16a}R^{16b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-yl-carbonyl, thiomorpholin-1-yl-carbonyl, 1-oxothiomorpholin-1-ylcarbonyl and 1,1-dioxo-thiomorpholin-1-ylcarbonyl; and wherein $R^{15}$ may additionally be aryl substituted with a radical —$COOR^4$; or a radical selected from —$NR^{5a}$—$C(=NR^{5b})$—$NR^{5c}R^{5d}$, —$NR^{5a}$—$C(=NR^{5e})$—$R^{5f}$, —O—$NR^{5a}$—$C(=NR^{5b})$—$NR^{5c}R^{5d}$, —O—$NR^{5a}$—$C(=NR^{5e})$—$R^{5f}$, -sulfonyl-$R^6$, —$NR^7R^8$, —$NR^9R^{10}$, a radical (a-1), (a-2), (a-3); wherein $R^4$, $R^{5a}$, $R^{5b}$, $R^{5c}$, $R^{5d}$, $R^6$, $R^7$, $R^8$, $R^9$, $R^{10}$, and the radicals (a-1), (a-2), (a-3) independently are as defined above;

$R^{16a}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

$R^{16b}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

each $R^{17}$ independently is hydrogen, $C_{1-4}$alkyl or aryl$C_{1-4}$alkyl;

$R^{18}$ is hydrogen, hydroxy, $C_{1-4}$alkyl or a radical —$COOR^4$;

-$a^1=a^2$-$a^3=a^4$- represents a bivalent radical of formula

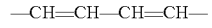 (c-1)
—CH=CH—CH=CH— wherein one, two, three or four of the hydrogen atoms in (c-1) may be replaced by a radical $C_{1-6}$alkyl, $C_{1-4}$alkoxy, halo, hydroxy, $(R^{5g})(R^{5h})$N—($C_{1-4}$alkanediyl)-O—, $(R^7)(R^8)$N—($C_{1-4}$alkanediyl)-O—, $(R^8)(R^9)$N—($C_{1-4}$alkanediyl)-O—, trifluoromethyl, cyano, a radical —$COOR^4$, $(R^{5a})(R^{5b})$N-carbonyl, $(R^{5a})(R^{5b})$N-sulfonyl, pyrrolidinylsulfonyl, piperidinylsulfonyl, homopiperidinylsulfonyl, formyl, $C_{1-6}$alkylcarbonyl, nitro, hydroxy$C_{1-6}$alkyl, $C_{1-4}$alkoxy$C_{1-6}$alkyl, $(R^4OOC)$—$C_{1-6}$alkyl, a radical —$N(R^{5a})(R^{5b})$, —$N(R^7)(R^8)$, —$N(R^9)(R^{10})$, a radical

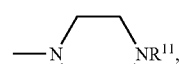 (a-1)

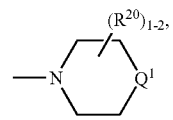 (a-7)

morpholinyl, thiomorpholinyl, 1-oxothiomorpholinyl, 1,1-dioxo-thiomorpholinyl, $(R^{5g})(R^{5h})N$—$(C_{1-4}$alkanediyl)-N$(R^{5c})$—, $(R^7)(R^8)N$—$(C_{1-4}$alkanediyl)-N $(R^{5c})$—, $(R^9)(R^{10})N$—$(C_{1-4}$alkanediyl)-N$(R^{5c})$—, $C_{1-6}$alkylcarbonylamino, $C_{1-6}$alkyloxycarbonylamino, trifluoroacetylamino, $C_{1-6}$alkylsulfonylamino, $(R^{5a})$ $(R^{5b})$N—$C_{1-4}$alkyl; aryl; Het$_1$ or Het$_2$;

$R^{20}$ is hydrogen, hydroxy, $C_{1-4}$alkyl, aryl$C_{1-4}$alkyl, $C_{1-4}$alkyloxy, aryl$C_{1-4}$alkyloxy, oxo, spiro($C_{2-4}$alkylenedioxy), spiro(di$C_{1-4}$alkyloxy), —$NR^{5g}R^{5h}$;

each $R^{5g}$ or $R^{5h}$ independently is hydrogen, $C_{1-4}$alkyl or aryl$C_{1-4}$alkyl, or $R^{5g}$ and $R^{5h}$ together with the nitrogen to which they attached form a pyrrolidinyl, piperidinyl, homopiperidinyl, morfolinyl, piperazinyl or 4-$C_{1-4}$alkylpiperazinyl radical; wherein each of said pyrrolidinyl, piperidinyl, homopiperidinyl, morfolinyl, piperazinyl or 4-$C_{1-4}$alkylpiperazinyl radical may optionally be substituted with hydroxy or oxo; or wherein one or more of the hydrogen atoms in (c-2), (c-3), (c-4) or (c-5) may be replaced with a radical selected from halo and $C_{1-6}$alkyl;

$R^3$ is Pyridinyl optionally be substituted with one, two, three, four or five substituents each independently selected from halo, cyano, nitro, $C_{1-6}$alkyl, hydroxy$C_{1-6}$alkyl, $C_{1-4}$alkoxy$C_{1-6}$alkyl, $(R^{5a})(R^{5b})N$—$C_{1-4}$alkyl, polyhalo$C_{1-6}$alkyl, $C_{3-7}$cycloalkyl, aryl$C_{1-6}$alkyl, formyl, $C_{1-6}$alkylcarbonyl, a radical —COOR$^4$, $(R^{5a})(R^{5b})$N-carbonyl, $(R^{5a})(R^{5b})$N-sulfonyl, hydroxy, $C_{1-6}$alkyloxy, aryl$C_{1-6}$alkyloxy, polyhalo$C_{1-6}$alkyloxy, formyloxy, $C_{1-6}$alkylcarbonyloxy, aryloxy, $(R^{5a})(R^{5b})$N-, formylamino, $C_{1-6}$alkylcarbonylamino, $C_{1-6}$alkyloxycarbonylamino $C_{1-6}$alkylsulfonylamino, mercapto, $C_{1-6}$alkylthio, arylthio, aryl$C_{1-6}$alkylthio, $C_{1-6}$alkylsulfinyl, $C_{1-6}$alkylsulfonyl, aryl, —CH (=N—O—$R^{5a}$), —C(=NH)—NH—$R^{5a}$;

aryl is phenyl optionally substituted with one or more substituents each individually selected from the group consisting of $C_{1-6}$alkyl, $C_{1-4}$alkoxy, halo, hydroxy, amino, trifluoromethyl, cyano, nitro, hydroxy$C_{1-6}$alkyl, cyano$C_{1-6}$alkyl, mono- or di($C_{1-4}$alkyl)amino, amino$C_{1-4}$alkyl, mono- or di($C_{1-4}$alkyl)amino$C_{1-4}$alkyl;

Het$_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl) amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$ alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl;

Het$_2$ is pyridyl, pyrimidinyl, pyrazinyl, pyridazinyl or triazinyl, wherein any ring carbon atom of each of said 6-membered nitrogen containing aromatic rings may optionally be substituted with a substituent selected from the group consisting of $C_{1-4}$alkyl.

2. A compound according to claim 1 wherein $R^3$ is optionally substituted with one, two, or three substituents each independently selected from halo, cyano, nitro, $C_{1-6}$alkyl, $CF_3$, —COOR$^4$, $(R^{5a})(R^{5b})$N-carbonyl, hydroxy, $C_{1-6}$alkyloxy, $(R^{5a})(R^{5b})N$—, $C_{1-6}$alkylthio, and $C_{1-6}$alkylsulfonyl.

3. A compound according to claim 1 wherein $R^3$ is optionally substituted with one or two substituents selected from halo, cyano, $C_{1-6}$alkyl, $CF_3$, —COOR$^4$, $(R^{5a})(R^{5b})$N-carbonyl, $C_{1-6}$alkyloxy, $C_{1-6}$alkylthio, $C_{1-6}$alkylsulfonyl.

4. A compound according to claim 1 wherein $R^1$ is cyano.

5. A compound according to claim 1 wherein:

X is NR$^2$ wherein R$^2$ is $C_{1-10}$alkyl being substituted with aryl, wherein said aryl is substituted with a radical —COOR$^4$;

X is NR$^2$ wherein R$^2$ is $C_{1-10}$alkyl substituted with a radical selected from —NR$^{5a}$—C(=NR$^{5b}$)—NR$^{5c}$R$^{5d}$, —O—NR$^{5a}$—C(=NR$^{5b}$)—NR$^{5c}$R$^{5d}$, -sulfonyl-R$^6$, —NR$^7$R$^8$, —NR$^9$R$^{10}$, a radical (a-1), (a-2), (a-3), (a-4) and (a-5);

X is NR$^2$ wherein R$^2$ is a radical (b-1), wherein R$^{19}$ is hydrogen or —COOR$^4$ and wherein Q$^1$ in radical (b-1) is a direct bond or —CH$_2$—;

X is NR$^2$ wherein R$^2$ is a radical (b-2), wherein Q$^2$ is O;

X is NR$^2$ wherein R$^2$ is a radical (b-3) wherein q is 1, 2 or 3;

X is NR$^2$ wherein R$^2$ is a radical (b-4) wherein m is 1-6; or

X is NR$^2$ wherein R$^2$ is a radical (b-5) wherein m is 1-5or,

X is NR$^2$, wherein R$^2$ is hydrogen, $C_{1-6}$alkyl, which may be optionally substituted with cyano, N(R$^{16a}$R$^{16b}$), pyrrolidinyl, piperidinyl, homopiperidinyl, piperazinyl, 4-($C_{1-4}$alkyl)-piperazinyl, morpholinyl, thiomorpholinyl, aryl, hydroxycarbonyl, $C_{1-4}$alkylcarbonyl.

6. A compound according to claim 1 wherein X is NR$^2$ wherein R$^2$ is a radical wherein q is 1, 2 or 3.

7. A compound according to claim 1 wherein X is NR$^2$ wherein R$^2$ is a radical, R$^{15}$ is NR$^{16a}$R$^{16b}$, pyrrolidinyl, piperidinyl, or 4-morpholinyl.

8. A compound according to claim 1 wherein

X is NR$^2$, wherein R$^2$ is $C_{1-6}$alkyl, which may be optionally substituted with N(R$^{16a}$R$^{16b}$), pyrrolidinyl, piperidinyl.

9. A compound according to claim 1 wherein

R$^3$ is optionally substituted with one or two substituents selected from halo, cyano, $C_{1-6}$alkyl, $CF_3$, —COOR$^4$, $(R^{5a})(R^{5b})$N-carbonyl, hydroxy, $C_{1-6}$alkyloxy, $C_{1-6}$alkylthio, and $C_{1-6}$alkylsulfonyl.

10. A compound according to claim 1 wherein

R$^3$ is optionally substituted with one or two substituents selected from halo, cyano, $C_{1-6}$alkyl, $CF_3$, —COOR$^4$, $(R^{5a})(R^{5b})$N-carbonyl, $C_{1-6}$alkyloxy, $C_{1-6}$alkylthio, and $C_{1-6}$alkylsulfonyl.

11. A compound according to claim 1 wherein one, two or three of the hydrogen atoms may be replaced by $C_{1-6}$alkyl, $C_{1-4}$alkoxy, halo, hydroxy, $(R^{5g})(R^{5h})N$—$(C_{1-4}$alkanediyl)-O—, a radical —COOR$^4$, $(R^{5a})(R^{5b})$N-sulfonyl, —N(R$^{5a}$) (R$^{5b}$), —N(R$^7$)(R$^8$), a radical (a-1), a radical (a-7), morpholinyl, $(R^{5g})(R^{5h})N$—$(C_{1-4}$alkanediyl)-N(R$^{5c}$)—, $C_{1-6}$alkyloxycarbonylamino, trifluoroacetylamino, and $(R^{5a})$ $(R^{5b})$N—$C_{1-4}$alkyl.

12. A compound according to claim 1 wherein

-a$^1$=a$^2$-a$^3$=a$^4$- represents a bivalent radical of formula (c-1); wherein one of the hydrogen atoms is replaced by hydroxy, or $(R^{5g})(R^{5h})N$—$(C_{1-4}$alkanediyl)-N(R$^{5c}$)—.

13. A compound according to claim 1 wherein $a^1=a^2-a^3=a^4-$ represents an unsubstituted radical (c-1).

14. A compound according to claim 1 wherein the compound of formula (I) is selected from:
   8-Methoxy-5-methyl-1-(6-methyl-pyridin-3-yl)-2-oxo-2,5-dihydro-1H-pyrido[3,2-b]indole-3-carbonitrile,
   1-(6-Chloro-5-pyridin-3-yl)-5-methyl-2-oxo-2,5-dihydro-1H-pyrido[3,2-b]indole-3-carbonitrile, and
   1-(6-Chloro-pyridin-3-yl)-hydroxy-5-methyl-2-oxo-2,5-dihydro-1H-pyrido[3,2-b]indole-3-carbonitrile.

15. A compound selected from: and
   1-(6-Chloropyridin-3-yl)-5-methyl-2-oxo-2,5-dihydro-1H-pyrido[3,2-b]indole-3-carbonitrile,
   5-Methyl-1-(6-methyl-pyridin-3-yl)-2-oxo-2,5-dihydro-1H-pyrido[3,2-b]indole-3-carbonitrile.

16. A pharmaceutical composition, comprising an effective amount of at least one compound of formula (I) as defined in claim 1 and a pharmaceutically tolerable excipient.

17. A pharmaceutical composition, comprising an effective amount of at Least one compound of formula (I) as defined in claim 1 and a pharmaceutically tolerable excipient.

18. A pharmaceutical composition, comprising an effective amount of at Least one compound of formula (I) as defined in claim 15 and a pharmaceutically tolerable excipient.

* * * * *